(12) United States Patent
Shluzas et al.

(10) Patent No.: US 7,226,451 B2
(45) Date of Patent: Jun. 5, 2007

(54) MINIMALLY INVASIVE ACCESS DEVICE AND METHOD

(76) Inventors: Alan E. Shluzas, 84 Acorn St., Millis, MA (US) 02054; Gary Lowery, 4136 E. Hancock Dr., Phoenix, AZ (US) 85028

( * ) Notice: Subject to any disclaimer, the term of this patent is extended or adjusted under 35 U.S.C. 154(b) by 412 days.

(21) Appl. No.: 10/678,744

(22) Filed: Oct. 2, 2003

(65) Prior Publication Data

US 2005/0075540 A1 Apr. 7, 2005

Related U.S. Application Data

(60) Provisional application No. 60/497,822, filed on Aug. 26, 2003, provisional application No. 60/497,763, filed on Aug. 26, 2003.

(51) Int. Cl.
*A61F 5/00* (2006.01)
(52) U.S. Cl. .................. 606/86; 604/104; 606/108; 600/219
(58) Field of Classification Search .............. 604/104, 604/106; 606/108, 86; 600/219, 220
See application file for complete search history.

(56) References Cited

U.S. PATENT DOCUMENTS

| | | |
|---|---|---|
| 151,228 A | 5/1874 | Knaffl |
| 530,728 A | 12/1894 | Sherbrook |
| 1,170,324 A | 2/1916 | Pomerene |
| 2,083,573 A | 6/1937 | Morgan |
| 2,313,164 A | 3/1943 | Nelson |
| 2,594,086 A | 4/1952 | Smith |
| 2,623,517 A | 12/1952 | Barlow et al. |
| 3,044,461 A | 7/1962 | Murdock |
| 3,070,088 A | 12/1962 | Brahos |
| 3,503,398 A | 3/1970 | Fogarty et al. |
| 3,509,873 A | 5/1970 | Karlin et al. |
| 3,749,088 A | 7/1973 | Kohlmann |
| 3,789,852 A | 2/1974 | Kim et al. |
| 3,841,317 A | 10/1974 | Awais |

(Continued)

FOREIGN PATENT DOCUMENTS

EP 0807415 A 11/1997

(Continued)

OTHER PUBLICATIONS

Partial International Search dated Jan. 27, 2005 for International Application No. PCT/US2004/027761, filed Aug. 26, 2004.

(Continued)

*Primary Examiner*—Eduardo C. Robert
*Assistant Examiner*—James L. Swiger
(74) *Attorney, Agent, or Firm*—Knobbe Martens Olson & Bear LLP

(57) ABSTRACT

A device that provides access to a surgical location within a patient has an elongate body that has a proximal end, a distal end, and an inner surface. The inner surface defines a passage that extends through the elongate body. The elongate body is capable of having a configuration when inserted within the patient wherein the cross-sectional area of the passage at a first location is greater than the cross-sectional area of said passage at a second location. The first location is distal to the second location. The passage is capable of having a generally oval shaped cross section between the second location and the proximal end.

51 Claims, 58 Drawing Sheets

U.S. PATENT DOCUMENTS

| | | |
|---|---|---|
| 3,965,890 A | 6/1976 | Gauthier ..................... 128/20 |
| 3,998,217 A | 12/1976 | Trumbull et al. |
| 4,010,741 A | 3/1977 | Gauthier |
| 4,130,113 A | 12/1978 | Graham |
| 4,155,355 A | 5/1979 | Yamamoto |
| 4,254,763 A | 3/1981 | McCready et al. |
| 4,421,107 A | 12/1983 | Estes et al. |
| 4,449,532 A | 5/1984 | Storz |
| 4,451,256 A | 5/1984 | Weikl et al. |
| 4,545,374 A | 10/1985 | Jacobson |
| 4,601,713 A | 7/1986 | Fuqua |
| 4,716,901 A | 1/1988 | Jackson |
| 4,784,118 A | 11/1988 | Fantone et al. |
| 4,817,587 A | 4/1989 | Janese |
| 4,863,133 A | 9/1989 | Bonnell |
| 4,899,729 A | 2/1990 | Gill et al. |
| 4,921,478 A | 5/1990 | Solano et al. |
| 4,984,564 A | 1/1991 | Yuen |
| 5,139,511 A | 8/1992 | Gill et al. |
| 5,163,949 A | 11/1992 | Bonutti |
| 5,190,561 A | 3/1993 | Graber |
| 5,196,023 A | 3/1993 | Martin |
| 5,197,971 A | 3/1993 | Bonutti |
| 5,231,974 A | 8/1993 | Giglio et al. .................. 128/20 |
| 5,295,477 A | 3/1994 | Janfaza |
| 5,295,994 A | 3/1994 | Bonutti |
| 5,312,417 A | 5/1994 | Wilk |
| 5,313,962 A | 5/1994 | Obenchain |
| 5,345,927 A | 9/1994 | Bonutti |
| 5,354,302 A | 10/1994 | Ko |
| 5,370,647 A | 12/1994 | Graber et al. |
| 5,370,659 A | 12/1994 | Sakashita |
| 5,400,774 A | 3/1995 | Villalta et al. |
| 5,417,203 A | 5/1995 | Tovey et al. |
| 5,439,464 A | 8/1995 | Shapiro |
| 5,443,479 A | 8/1995 | Bressi, Jr. |
| 5,454,365 A | 10/1995 | Bonutti |
| 5,490,819 A | 2/1996 | Nicholas et al. |
| 5,503,617 A | 4/1996 | Jako |
| 5,505,690 A | 4/1996 | Patton et al. |
| 5,529,571 A | 6/1996 | Daniel |
| 5,601,590 A | 2/1997 | Bonutti et al. |
| 5,667,481 A | 9/1997 | Villalta et al. |
| 5,667,520 A | 9/1997 | Bonutti et al. |
| 5,681,265 A | 10/1997 | Maeda et al. |
| 5,688,223 A | 11/1997 | Rosendahl |
| 5,688,224 A | 11/1997 | Forkey et al. |
| 5,690,606 A | 11/1997 | Slotman |
| 5,707,359 A | 1/1998 | Bufalini |
| 5,718,664 A | 2/1998 | Peck et al. |
| 5,728,046 A | 3/1998 | Mayer et al. |
| 5,762,629 A | 6/1998 | Kambin |
| 5,782,919 A | 7/1998 | Zdeblick et al. |
| 5,792,044 A | 8/1998 | Foley et al. |
| 5,795,289 A | 8/1998 | Wyttenbach |
| 5,795,291 A | 8/1998 | Koros et al. .................. 600/232 |
| 5,813,978 A | 9/1998 | Jako |
| 5,827,319 A | 10/1998 | Carlson et al. |
| 5,851,214 A | 12/1998 | Larsen et al. |
| 5,868,668 A | 2/1999 | Weiss |
| 5,902,231 A | 5/1999 | Foley et al. |
| 5,944,658 A | 8/1999 | Koros et al. .................. 600/232 |
| 5,954,635 A | 9/1999 | Foley et al. |
| 5,961,499 A | 10/1999 | Bonutti et al. |
| 5,976,161 A | 11/1999 | Kirsch et al. |
| 5,997,508 A | 12/1999 | Lunn |
| 6,024,697 A | 2/2000 | Pisarik |
| 6,036,638 A | 3/2000 | Nwawka |
| 6,083,154 A | 7/2000 | Liu et al. |
| 6,096,046 A | 8/2000 | Weiss |
| 6,120,437 A | 9/2000 | Yoon et al. |
| 6,126,671 A | 10/2000 | Richards et al. |
| 6,139,493 A | 10/2000 | Koros et al. .................. 600/215 |
| 6,152,871 A | 11/2000 | Foley et al. |
| 6,162,236 A | 12/2000 | Osada |
| 6,171,299 B1 | 1/2001 | Bonutti |
| 6,176,823 B1 | 1/2001 | Foley et al. |
| 6,187,000 B1* | 2/2001 | Davison et al. ................. 606/1 |
| 6,206,826 B1 | 3/2001 | Mathews et al. |
| 6,312,443 B1 | 11/2001 | Stone |
| 6,338,730 B1 | 1/2002 | Bonutti et al. |
| 6,354,995 B1 | 3/2002 | Hoftman et al. ............ 600/219 |
| 6,361,488 B1 | 3/2002 | Davison et al. ............. 600/102 |
| 6,364,832 B1 | 4/2002 | Propp |
| 6,371,968 B1 | 4/2002 | Kogasaka et al. |
| 6,383,195 B1 | 5/2002 | Richard |
| 6,398,721 B1 | 6/2002 | Nakamura et al. |
| 6,432,048 B1 | 8/2002 | Francois |
| 6,434,416 B1 | 8/2002 | Mizoguchi et al. |
| 6,464,634 B1 | 10/2002 | Fraser |
| 6,490,083 B1 | 12/2002 | McManus |
| 6,494,893 B2 | 12/2002 | Dubrul et al. |
| 6,497,654 B1 | 12/2002 | Leonard et al. |
| 6,508,759 B1 | 1/2003 | Taylor et al. |
| 6,520,907 B1 | 2/2003 | Foley et al. |
| 6,524,320 B2 | 2/2003 | DiPoto |
| 6,530,880 B2 | 3/2003 | Pagliuca ..................... 600/102 |
| 6,530,926 B1 | 3/2003 | Davison ...................... 606/61 |
| 6,596,008 B1 | 7/2003 | Kambin |
| 6,610,009 B2 | 8/2003 | Person |
| 6,616,605 B2 | 9/2003 | Wright et al. |
| 6,652,553 B2 | 11/2003 | Davison et al. ............. 606/190 |
| 6,712,795 B1 | 3/2004 | Cohen |
| 6,800,084 B2 | 10/2004 | Davison et al. |
| 6,945,933 B2 | 9/2005 | Branch et al. |
| 7,001,397 B2 | 2/2006 | Davison et al. |
| 7,014,608 B2 | 3/2006 | Larson et al. |
| 7,056,321 B2 | 6/2006 | Pagliuca et al. |
| 7,108,705 B2 | 9/2006 | Davison et al. |
| 2002/0002360 A1 | 1/2002 | Orth et al. |
| 2002/0022764 A1 | 2/2002 | Smith et al. |
| 2003/0009130 A1 | 1/2003 | Stecker et al. |
| 2003/0014068 A1 | 1/2003 | Bonutti |
| 2003/0073998 A1 | 4/2003 | Unger et al. |
| 2003/0083688 A1* | 5/2003 | Simonson ..................... 606/191 |
| 2003/0083689 A1 | 5/2003 | Simonson ..................... 606/191 |
| 2003/0097045 A1 | 5/2003 | Kashyap |
| 2003/0163030 A1 | 8/2003 | Arriaga |
| 2003/0187431 A1 | 10/2003 | Simonson ..................... 606/53 |
| 2003/0191371 A1 | 10/2003 | Smith et al. |
| 2003/0195550 A1 | 10/2003 | Davison et al. |
| 2003/0195551 A1 | 10/2003 | Davison et al. |
| 2003/0199885 A1 | 10/2003 | Davison et al. |
| 2003/0199915 A1 | 10/2003 | Shimm |
| 2004/0098016 A1 | 5/2004 | Bonutti |
| 2004/0176665 A1 | 9/2004 | Branch et al. |
| 2004/0181231 A1 | 9/2004 | Emstad et al. |
| 2004/0230100 A1 | 11/2004 | Shluzas |
| 2005/0137461 A1 | 6/2005 | Marchek et al. |
| 2005/0159650 A1 | 7/2005 | Raymond et al. |
| 2005/0159651 A1 | 7/2005 | Raymond et al. |

FOREIGN PATENT DOCUMENTS

| | | |
|---|---|---|
| EP | 0807415 A2 | 11/1997 |
| WO | WO 95/22285 | 8/1995 |
| WO | WO 01/54560 A2 | 2/2001 |
| WO | WO 2002/09801 | 2/2002 |
| WO | WO 2004/012617 A2 | 2/2004 |

OTHER PUBLICATIONS

Co-pending U.S. Appl. No. 10/440,231, filed May 16, 2003, titled Cannula for receiving surgical instruments, and assigned to the assignee of this application.

Co-pending U.S. Appl. No. 10/441,319, filed May 16, 2003, titled Cannula for receiving surgical instruments, and assigned to the assignee of this application.
Co-pending U.S. Appl. No. 10/440,002, filed May 16, 2003, titled Cannula for receiving surgical instruments, and assigned to the assignee of this application.
Co-pending U.S. Appl. No. 10/440,278, filed May 16, 2003, titled Cannula for receiving surgical instruments, and assigned to the assignee of this application.
Co-pending U.S. Appl. No. 10/439,979, filed May 16, 2003, titled Cannula for receiving surgical instruments, and assigned to the assignee of this application.
Co-pending U.S. Appl. No. 10/439,385, filed May 16, 2003, titled Cannula for receiving surgical instruments, and assigned to the assignee of this application.
Co-pending U.S. Appl. No. 10/435,730, filed May 9, 2003, titled Method for performing a surgical procedure and a cannula for use in performing the surgical procedure, and assigned to the assignee of this application.
Co-pending U.S. Appl. No. 10/713,820, filed Nov. 14, 2003, titled Cannula for receiving surgical instruments, and assigned to the assignee of this application.
Co-pending U.S. Appl. No. 10/686,063, filed Oct. 15, 2003, titled Cannula for receiving surgical instruments, and assigned to the assignee of this application.
Co-pending U.S. Appl. No. 10/686,154, filed Oct. 15, 2003, titled Method of securing vertebrae, and assigned to the assignee of this application.
Co-pending U.S. Appl. No. 10/658,736, filed Sep. 9, 2003, titled Methods and apparatuses for treating the spine through an access device, and assigned to the assignee of this application.
Co-pending U.S. Appl. No. 09/772,605, filed Jan. 31, 2001, titled Method for performing a surgical procedure and a cannula for use in performing the surgical procedure, and assigned to the assignee of this application.
Response to Office Action, mailed Feb. 2, 2004, for U.S. Appl. No. 09/772,605, filed Jan. 31, 2001.
Ditsworth, David A., M.D., *Surg Neurol*, 49; 588-598, 1998 "Endoscopic Transforaminal Lumbar Discectomy and Reconfiguration: A Postero-lateral Approach into the Spinal Canal".
Endius Marketing Bulletin, 2002, Atavi Atraumatic Spine Fusion System "How do I decompress using Atavi System?"
Endius Marketing Bulletin, 2002, Atavi Atraumatic Spine Fusion System "Minimally Invasive Update on Danek".

Foley, Kevin T., M.D., Gupta, Sanjay K., M.D., Justis, Jeff R., B.S., Sherman, Michael C., M.S., *Neurosurg Focus*, 10: 1-8, 2001 "Percutaneous pedicle screw fixation of the lumbar spine".
Guiot, Bernard H., M.D., Khoo, Larry T., M.D., Fessler, Richard G., M.D., Ph.D., *SPINE*, 27, 4: 432-438, 2002 "A Minimally Invasive Technique for Decompression of the Lumbar Spine".
Kambin, Parviz, Publisher Unknown, Chapter 77, 1055-1066, Date Unknown "Arthroscopic Lumbar Interbody Fusion".
Kambin, Parviz, The Adult Spine: Principles and Practice, 2$^{nd}$ edition; Lippincott-Raven, 2037-2046, 1997 "Arthroscopic Lumbar Intervertebral Fusion".
Kambin, Parviz, The Mount Sinai Journal of Medicine, 58, 2: 159-164, 1991 "Arthroscopic Microdiskectomy".
Kambin, Parviz, Op rative Arthroscopy, Second Edition, 89:1215-1225, 1996 "Arthroscopic Techniques for Spinal Surgery".
Kambin, Parviz, Publisher Unknown, Chapter 9:117-121, Date Unknown "Posterolateral Percutaneous Lumbar Interbody Fusion".
Kambin, Parviz, *Advances in Operative Orthopaedics*, 3:147-171, 1995 "The Role of Minimally Invasive Surgery in Spinal Disorders".
Medtronic Sofamor Danek, *METRx MicroEndoscopic Discectomy*, 1999 "An Evolution in Minimally Invasive Spine Surgery".
Medtronic Sofamor Danek, *METRx MicroDiscectomy System*, 2000 "The Next Step in Minimally Invasive Discectomy Utilizing The Operating Microscope".
Medtronic Sofmor Danek, *METRx Microdiscectomy Surgical Technique*, 2001 as described by: Donald L. Hilton, Jr., M.D., F.A.C.S. and Sylvain Palmer, M.D., F.A.C.S.
Medtronic Sofamor Danek, *Orthopedics Today*, 1-20, 2002 "Minimal Access Spinal Technologies".
Stauber, Martin H., M.D., Bassett, George S., M.D., *SPINE*, 19, 1: 57-61, 1994 "Pedicle Screw Placement With Intraosseous Endoscopy".
Invitation to Pay Additional Fees with Partial International Search Report, PCT/US2004/027761 dated Jan. 27, 2005.
International Search Report with Written Opinion, PCT/US2004/027761 dated Apr. 12, 2004.
Caspar, Wolfhard, M.D., "The Caspar Microsurgical Discetomy and Comparison with a Conventional Standard Lumbar Disc Procedure" Neurosurgery, Jan. 1991, pags. 78-87, vol. 28, No. 1.

* cited by examiner

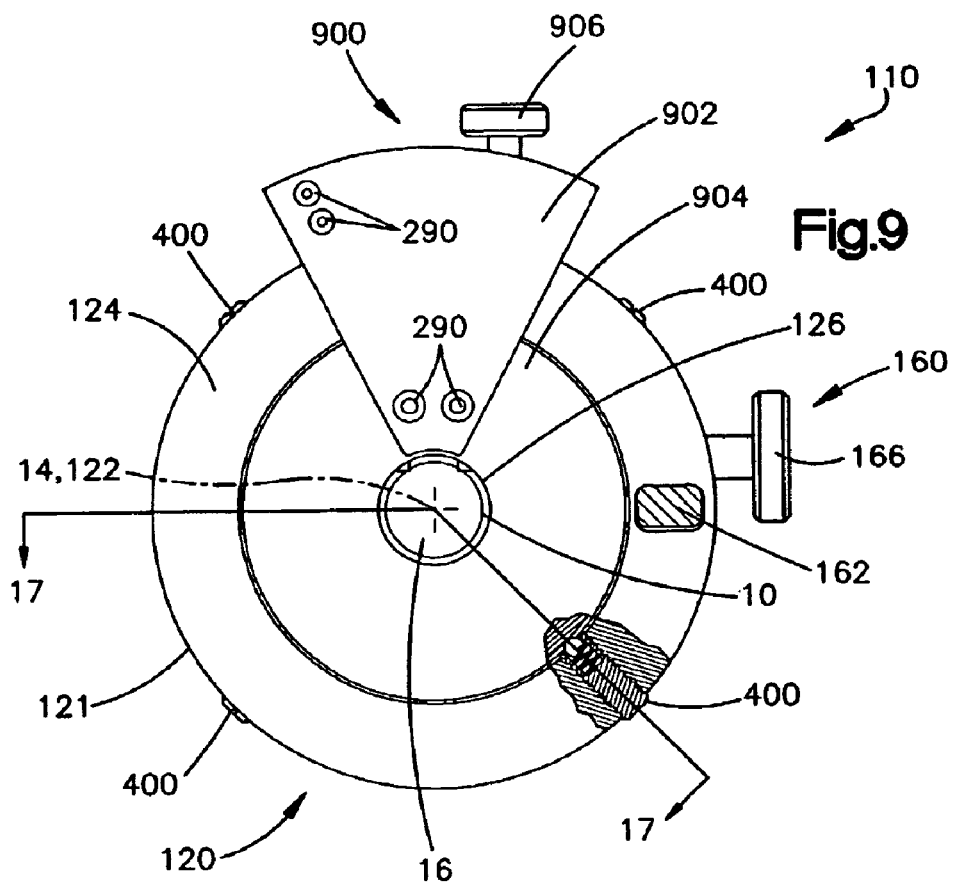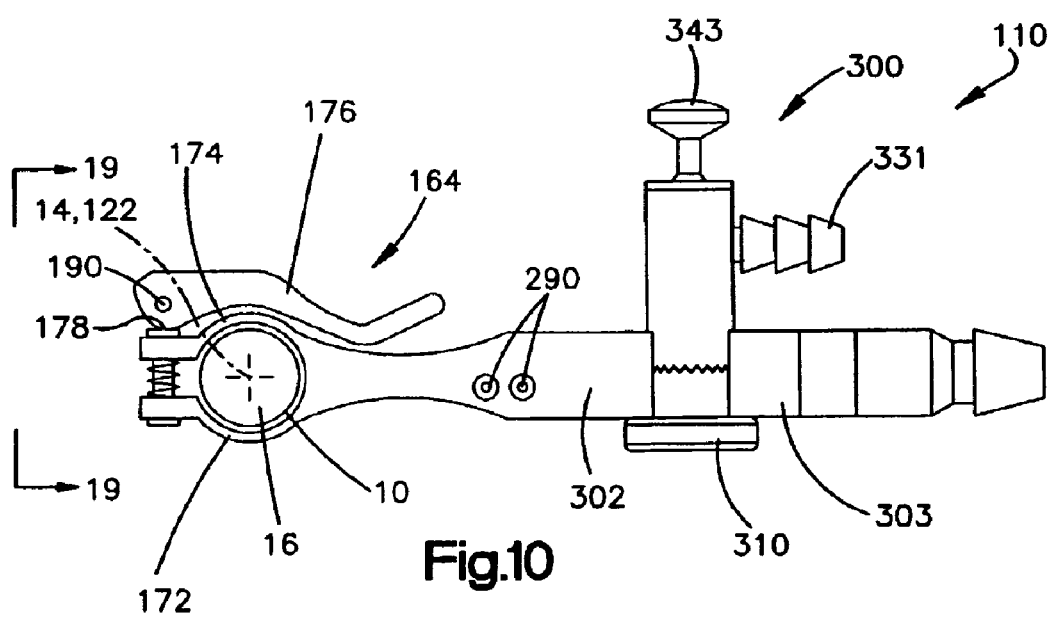

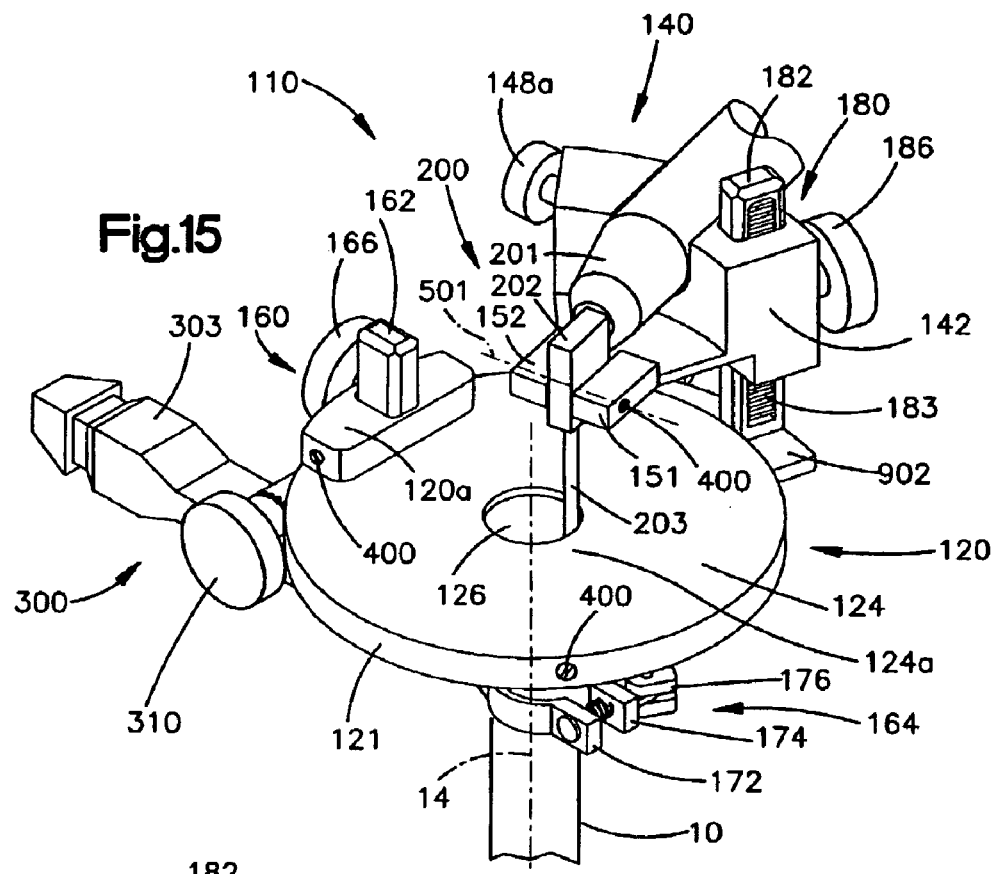
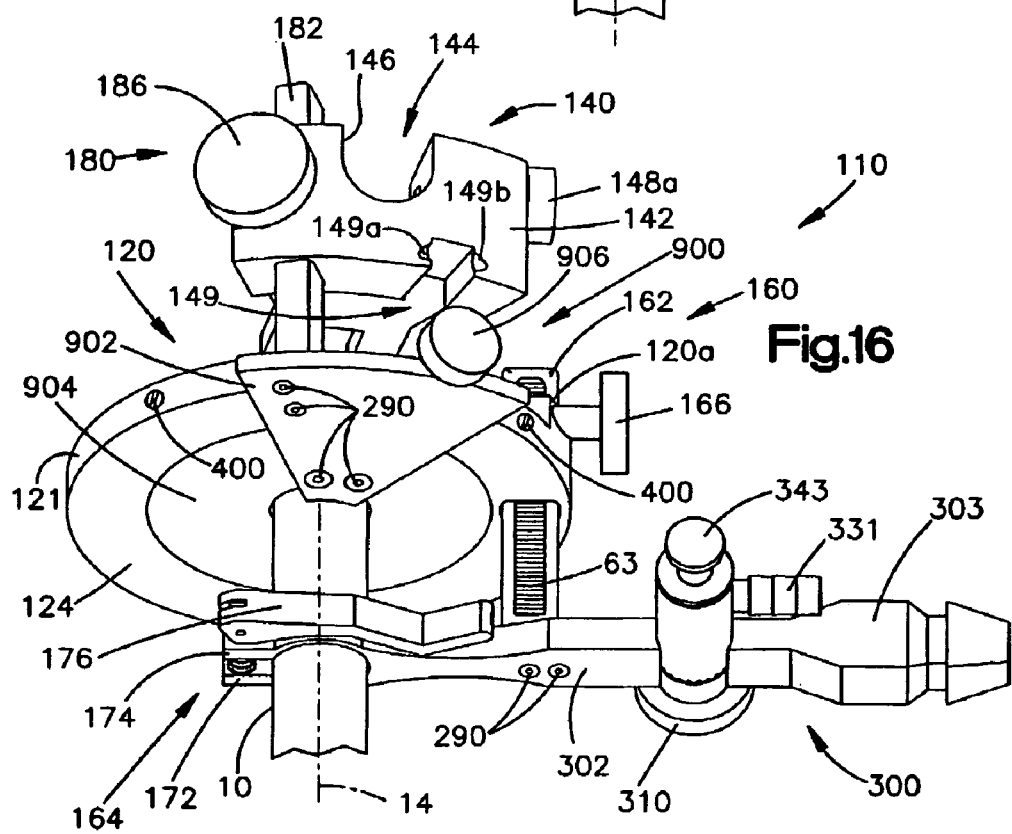

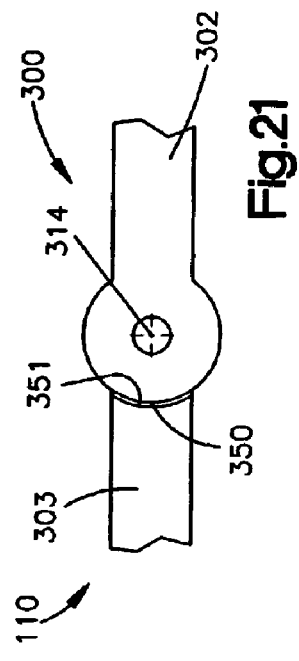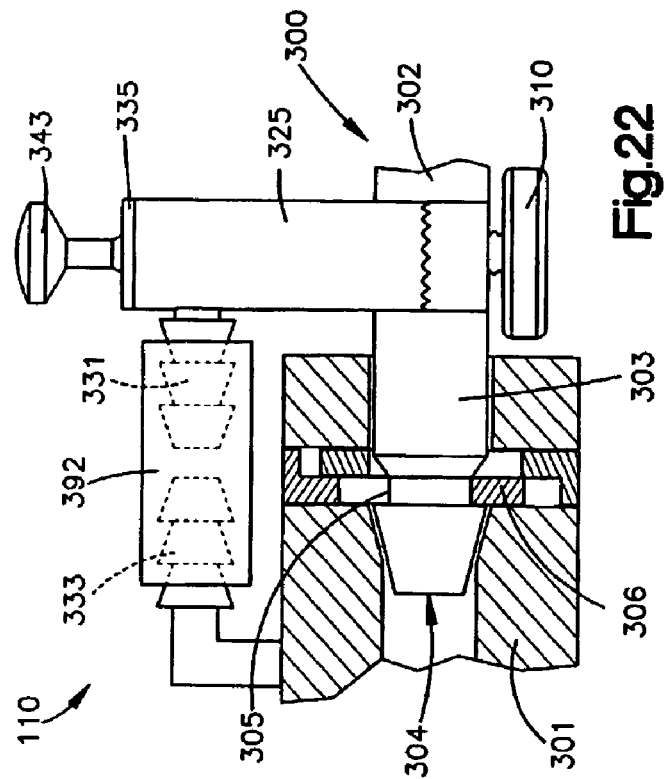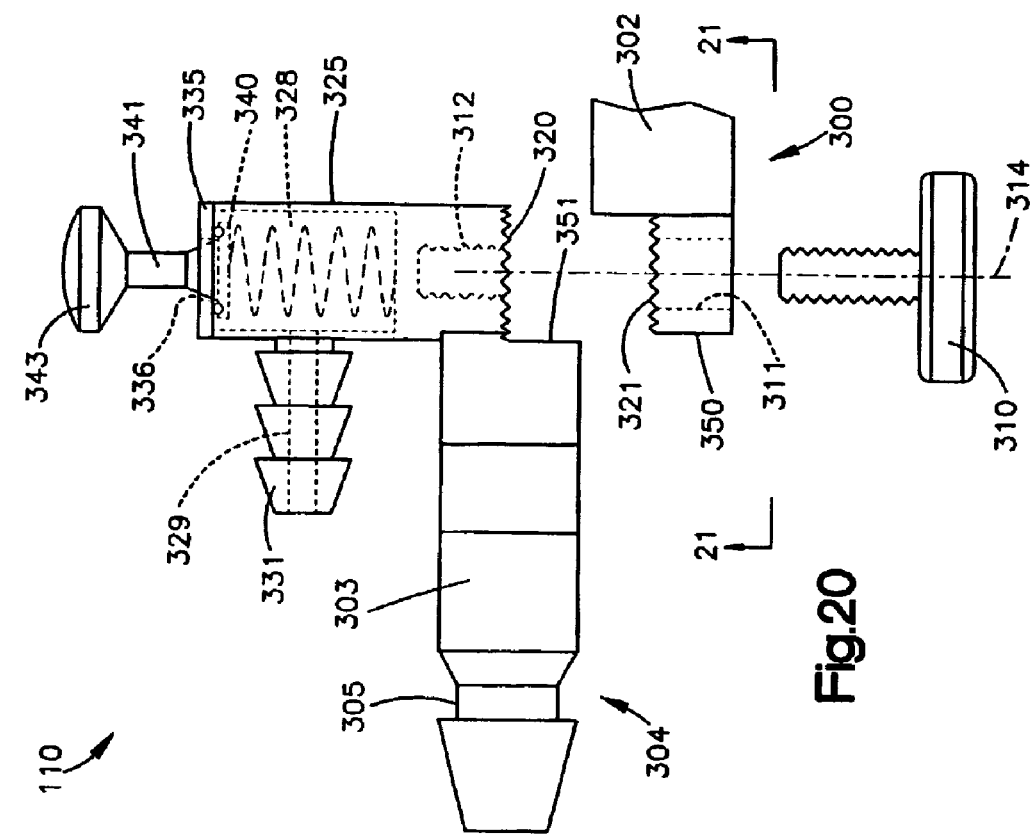

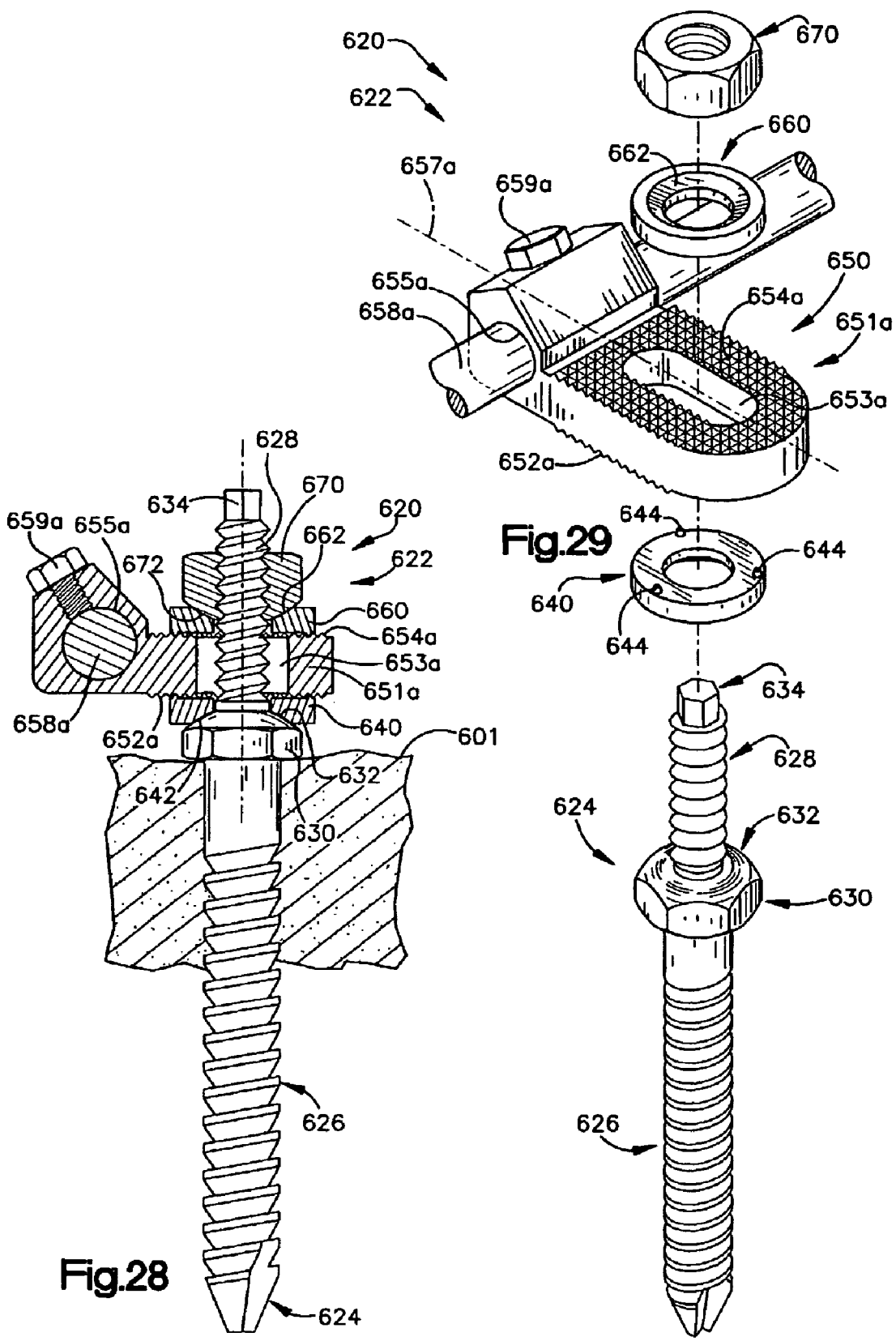

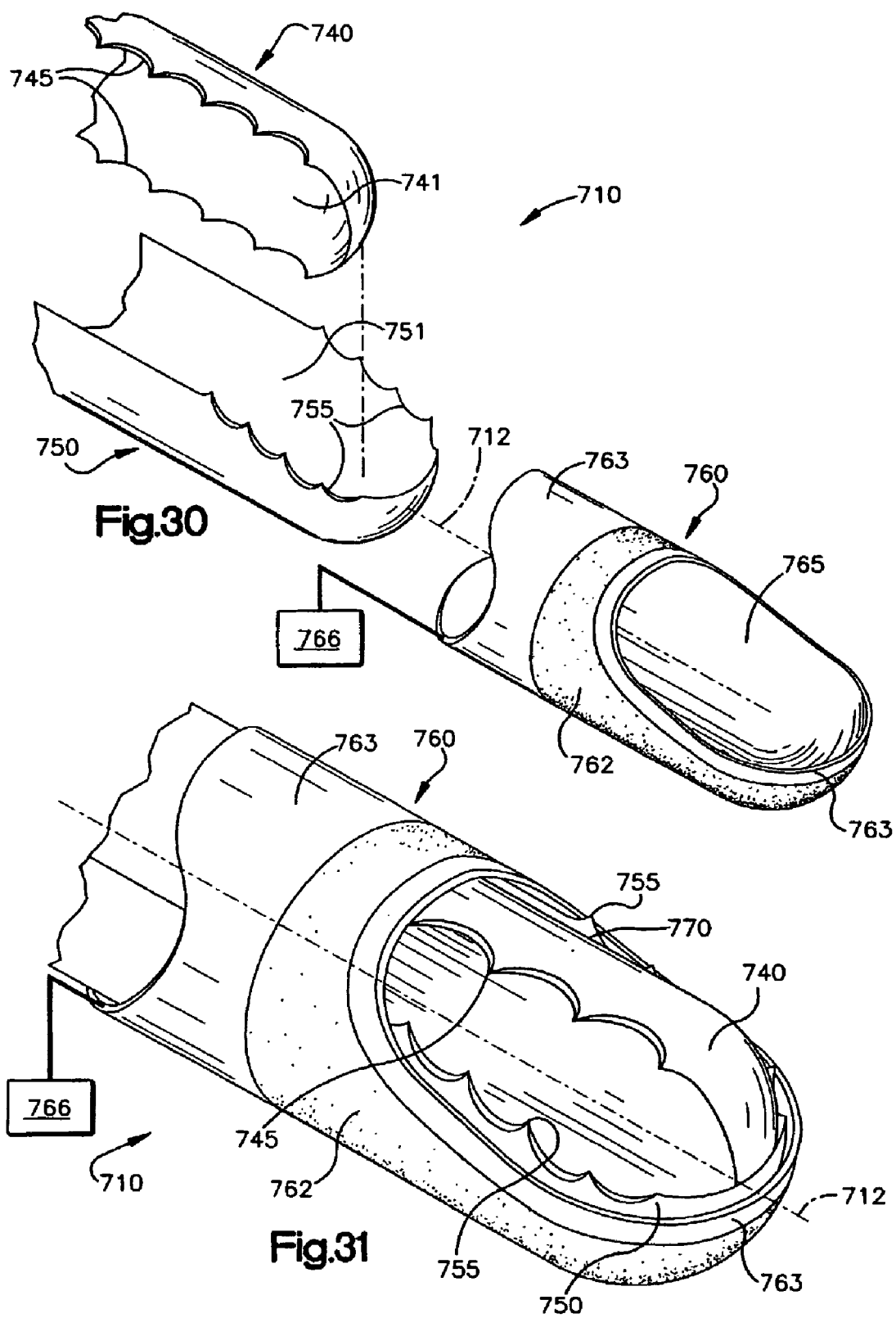

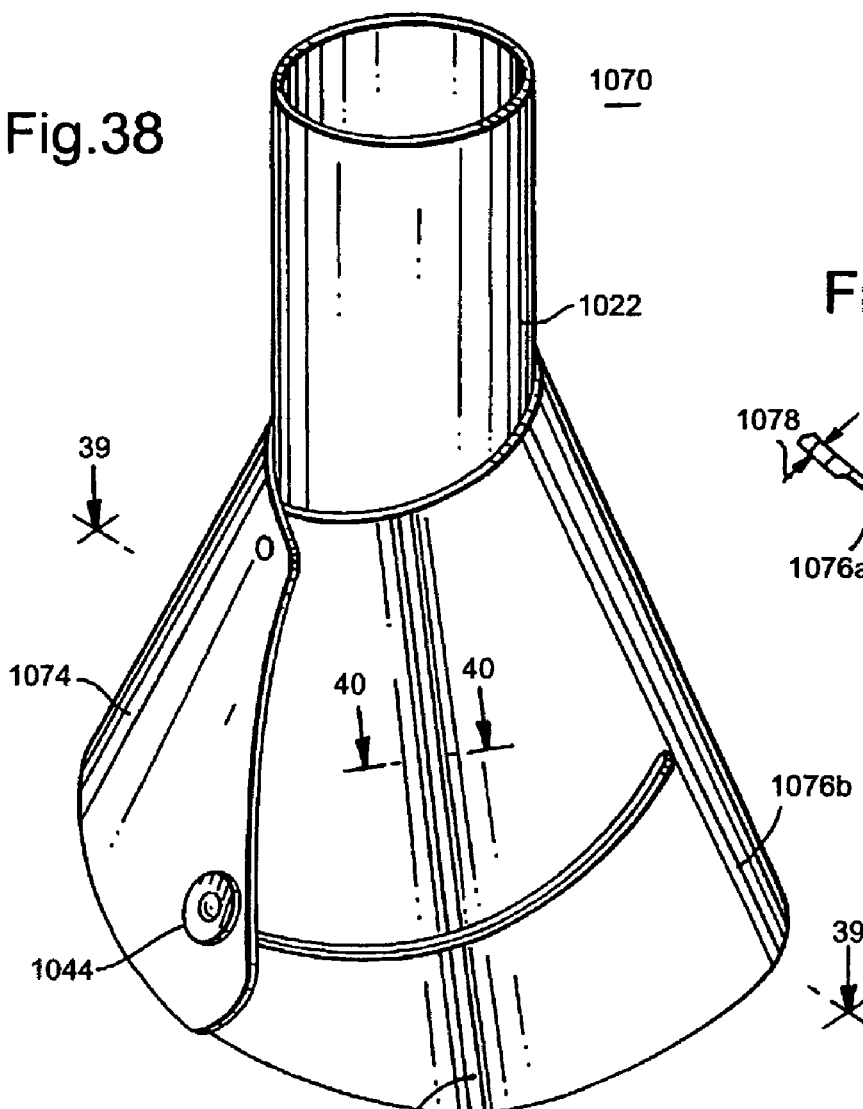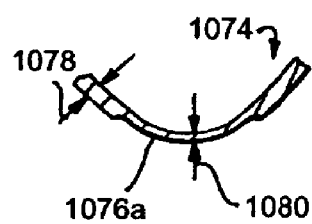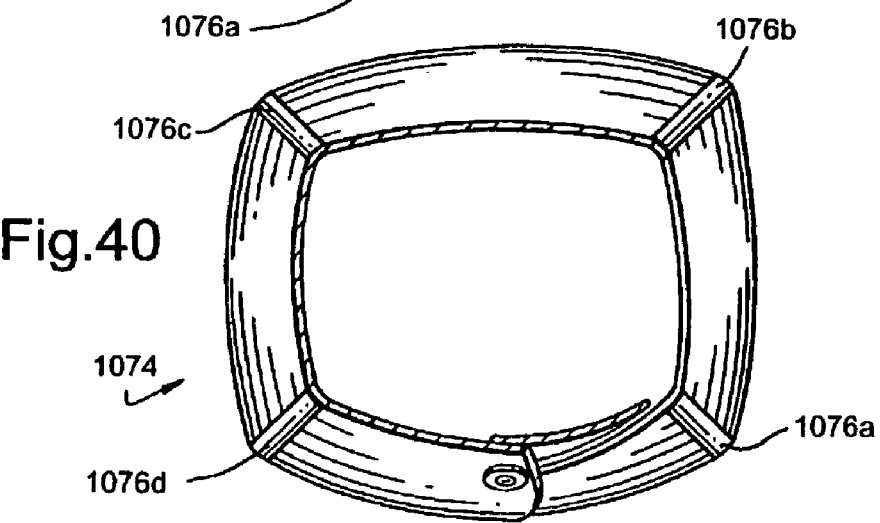

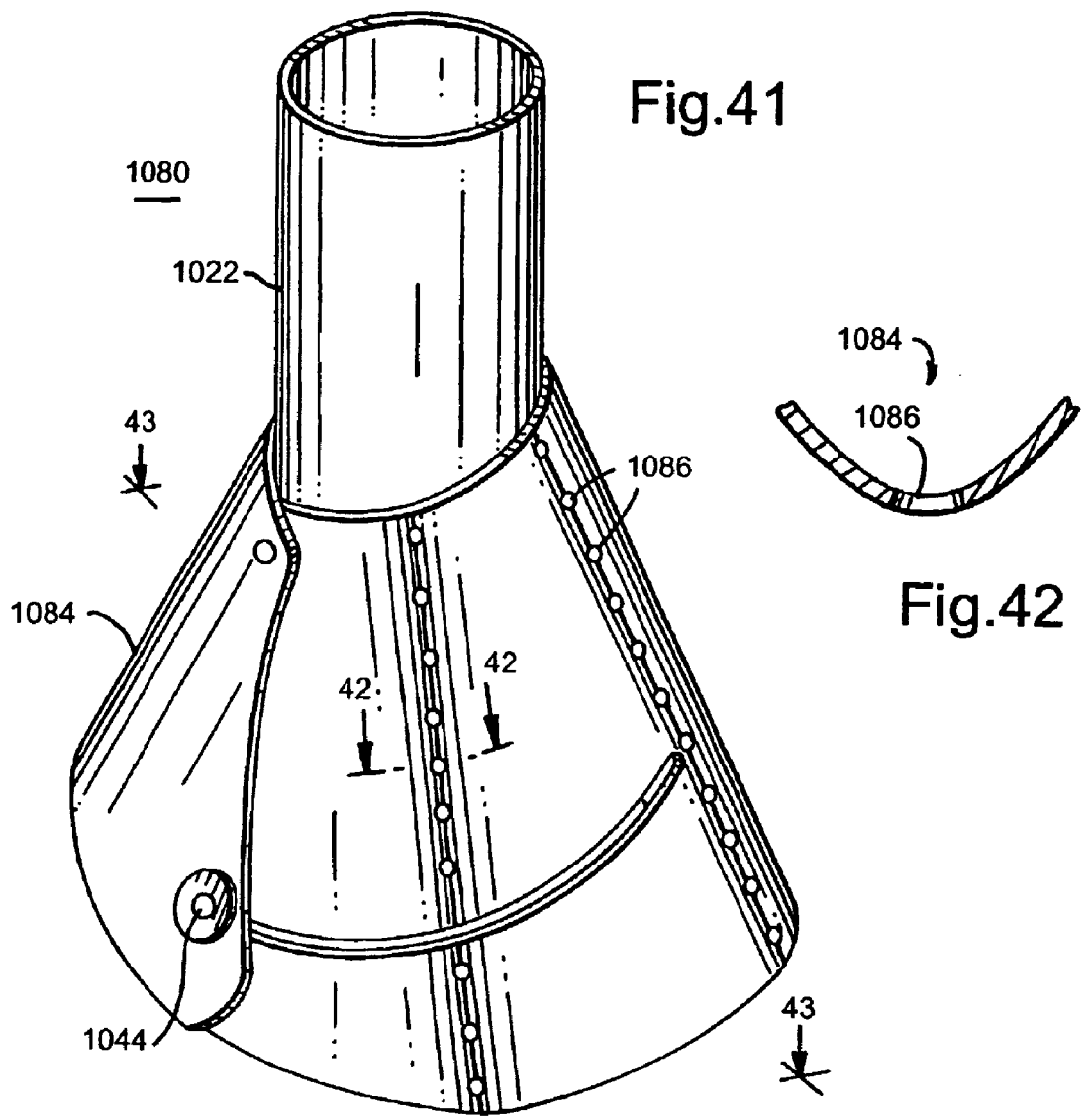
Fig.41
Fig.42
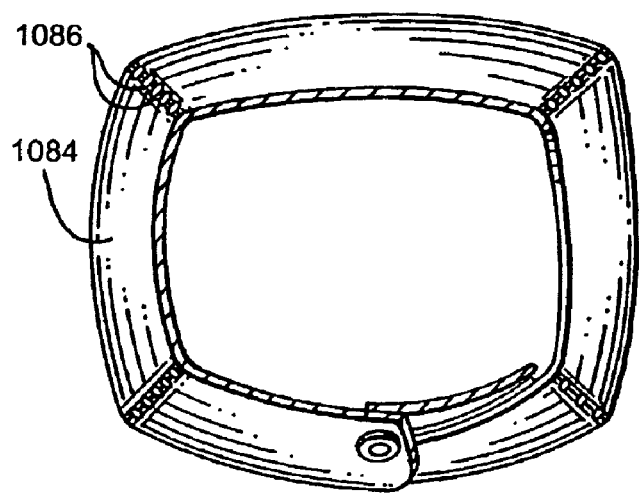
Fig.43

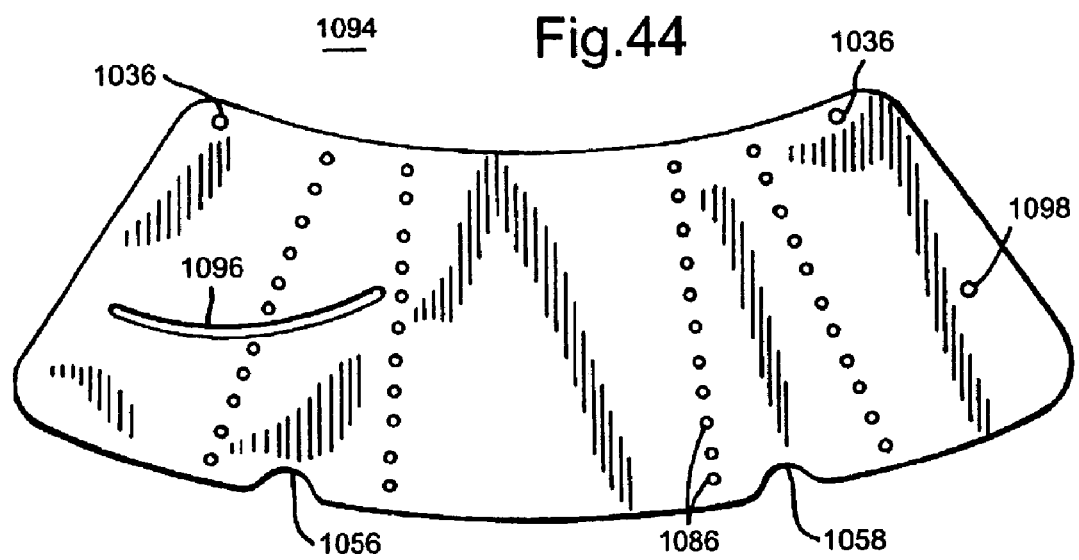
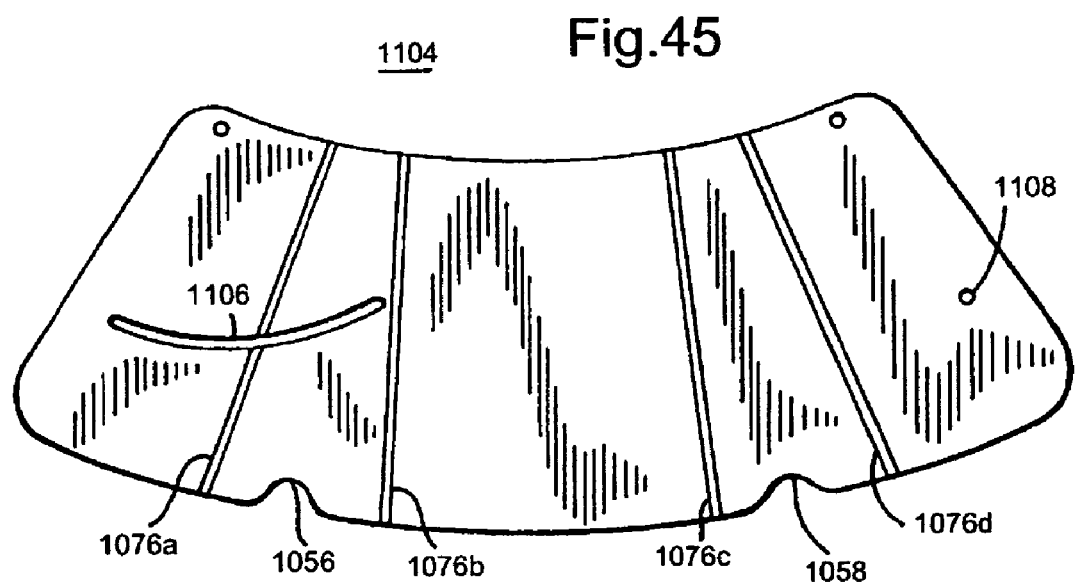

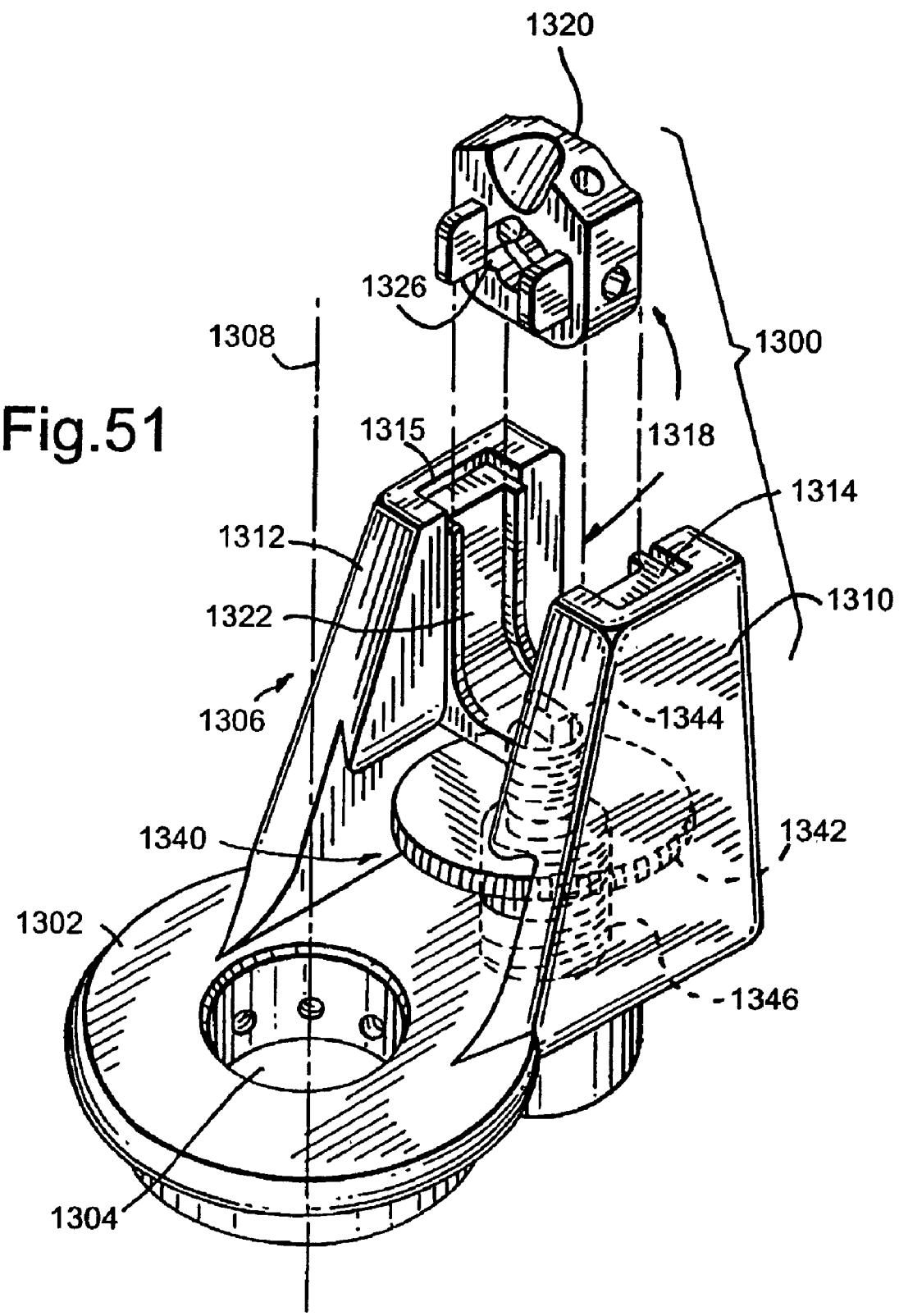

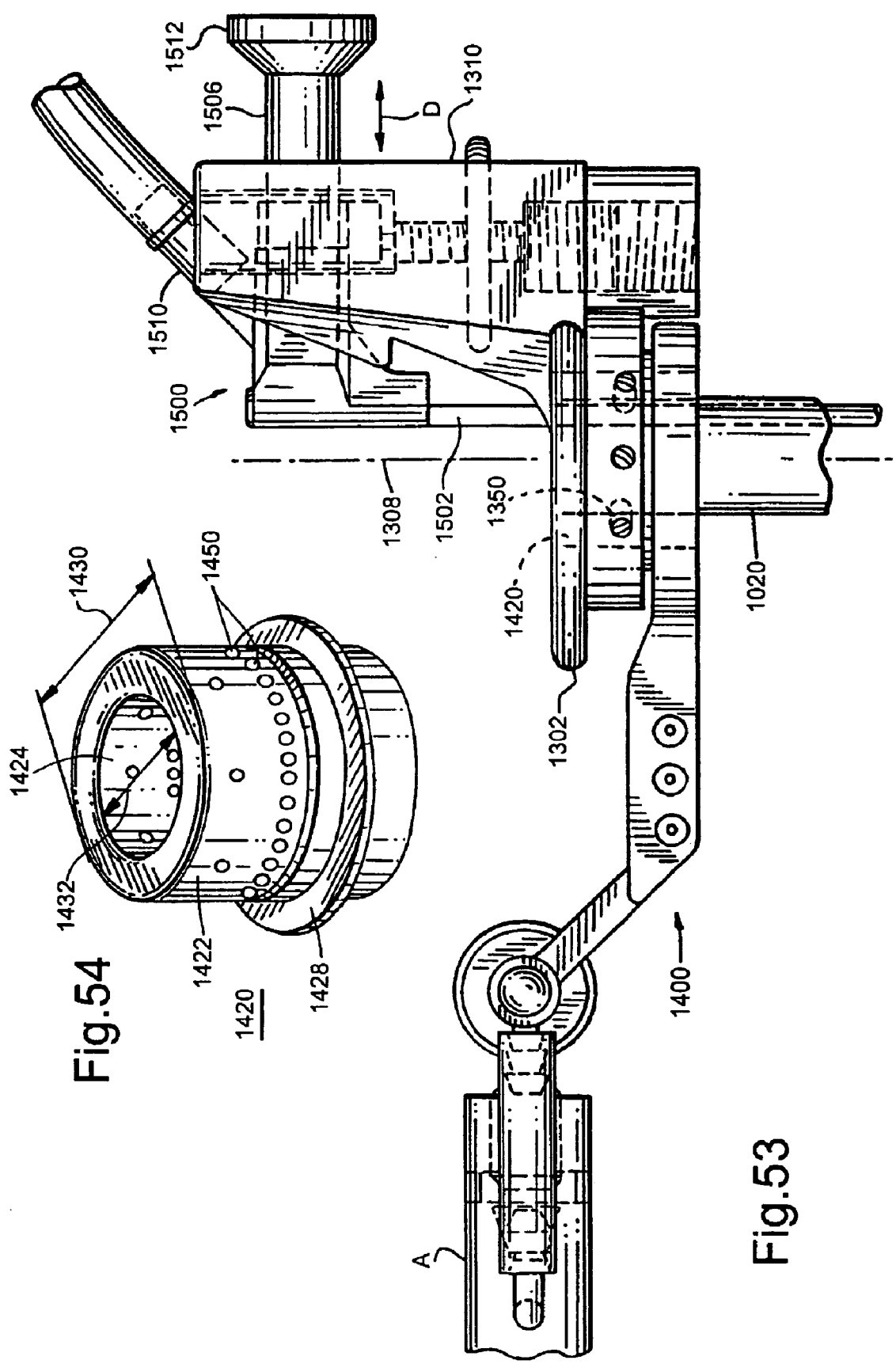

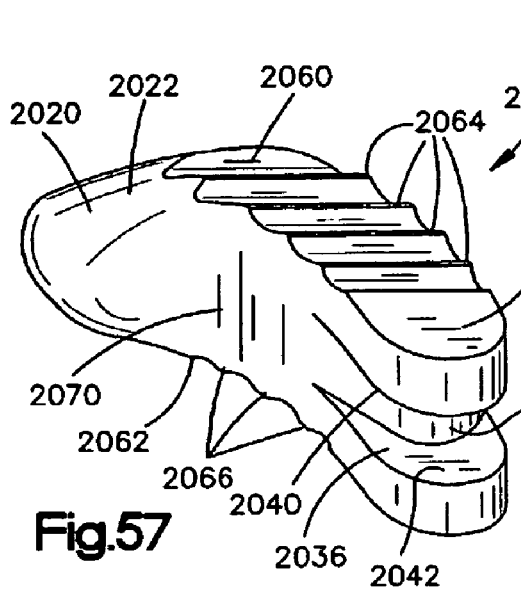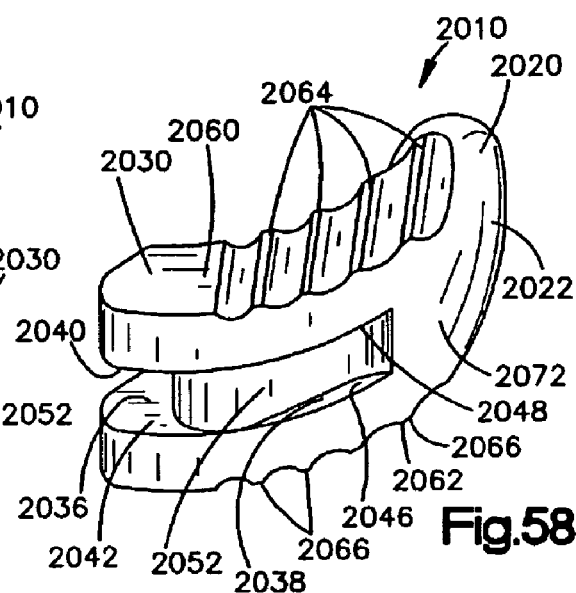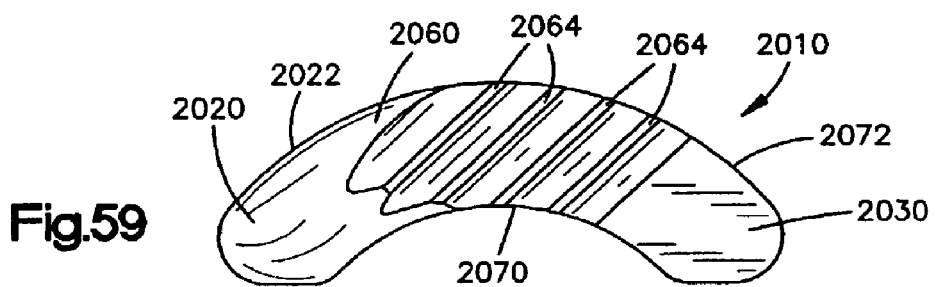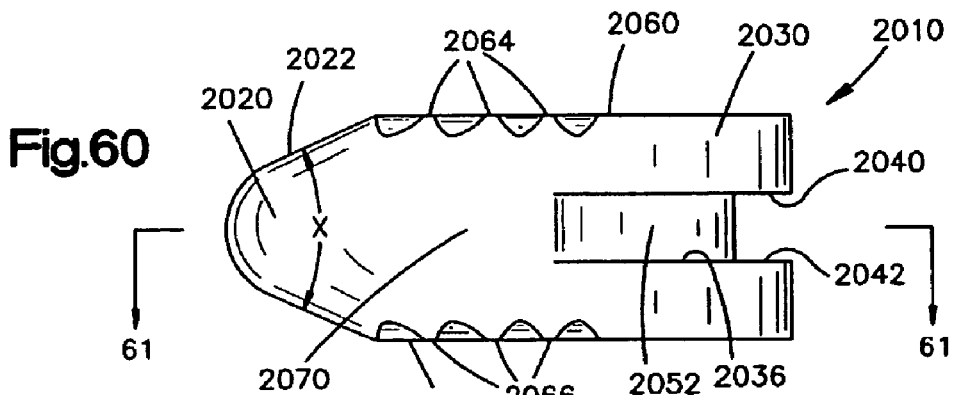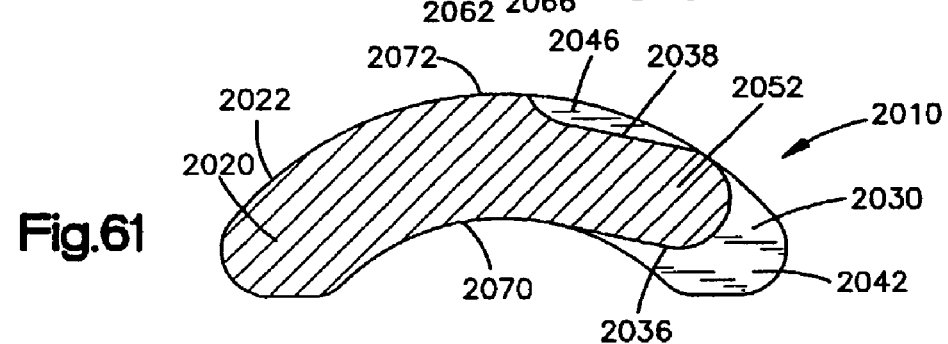

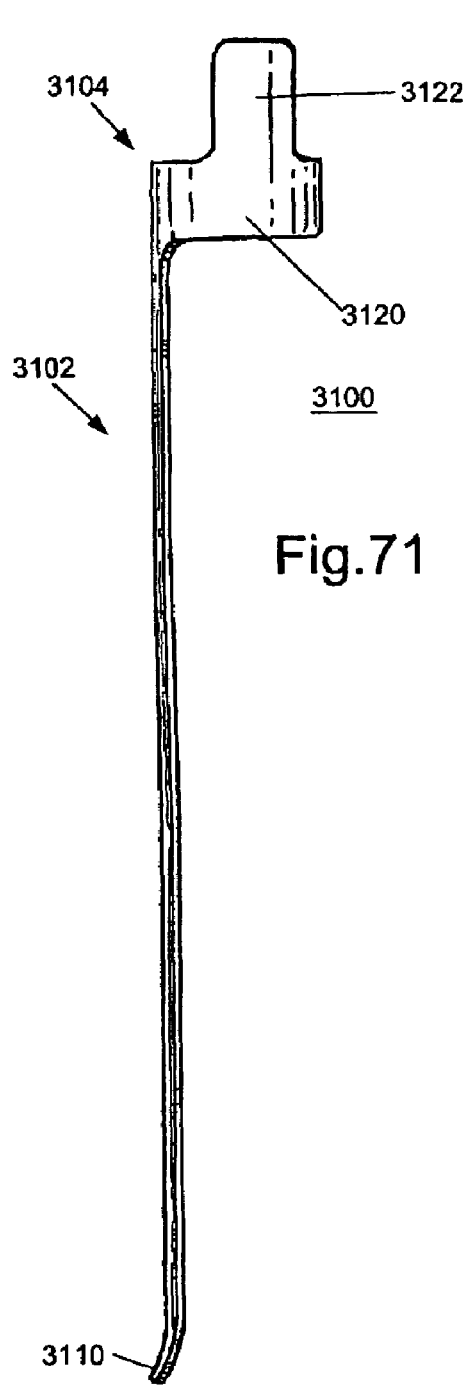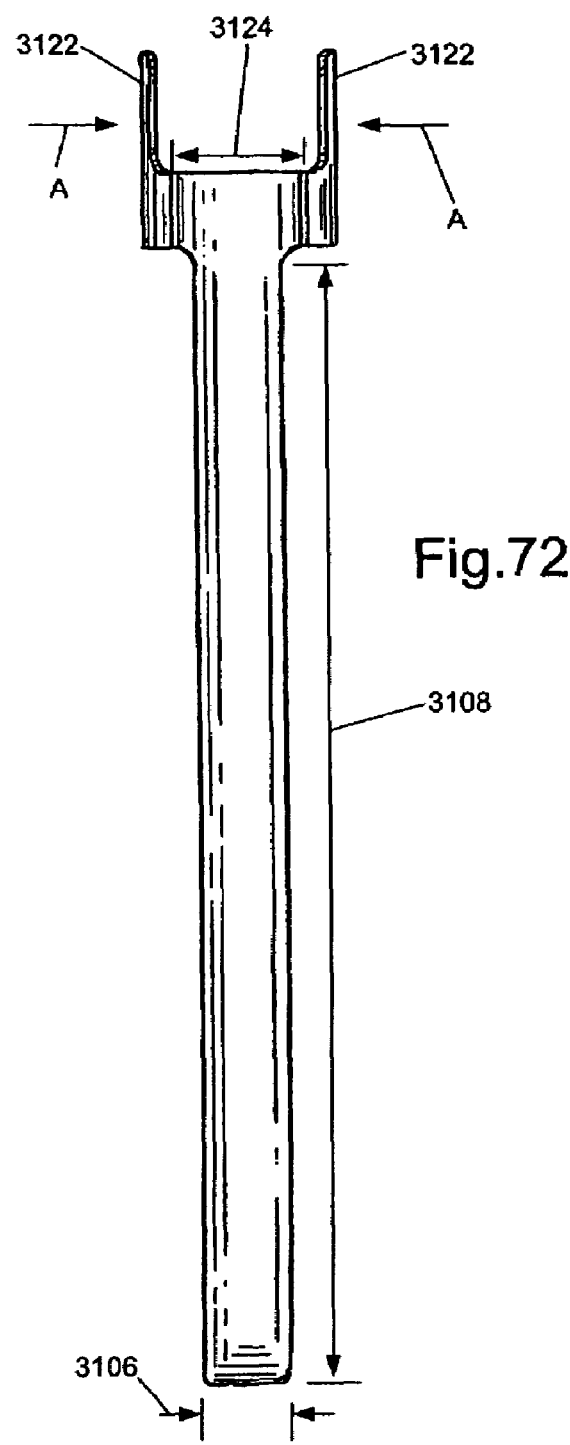
Fig.71
Fig.72

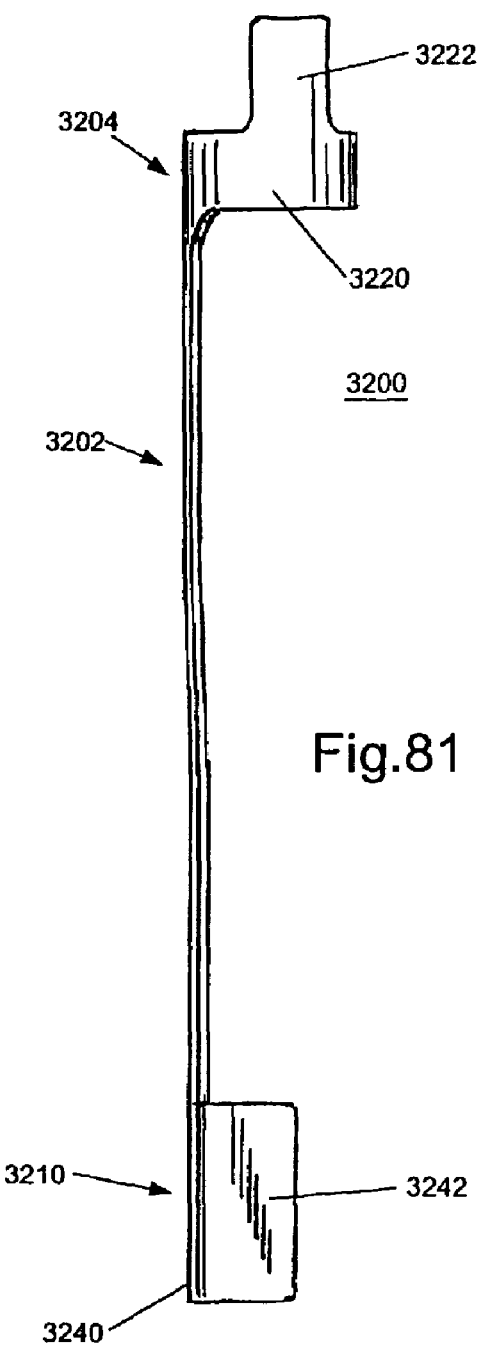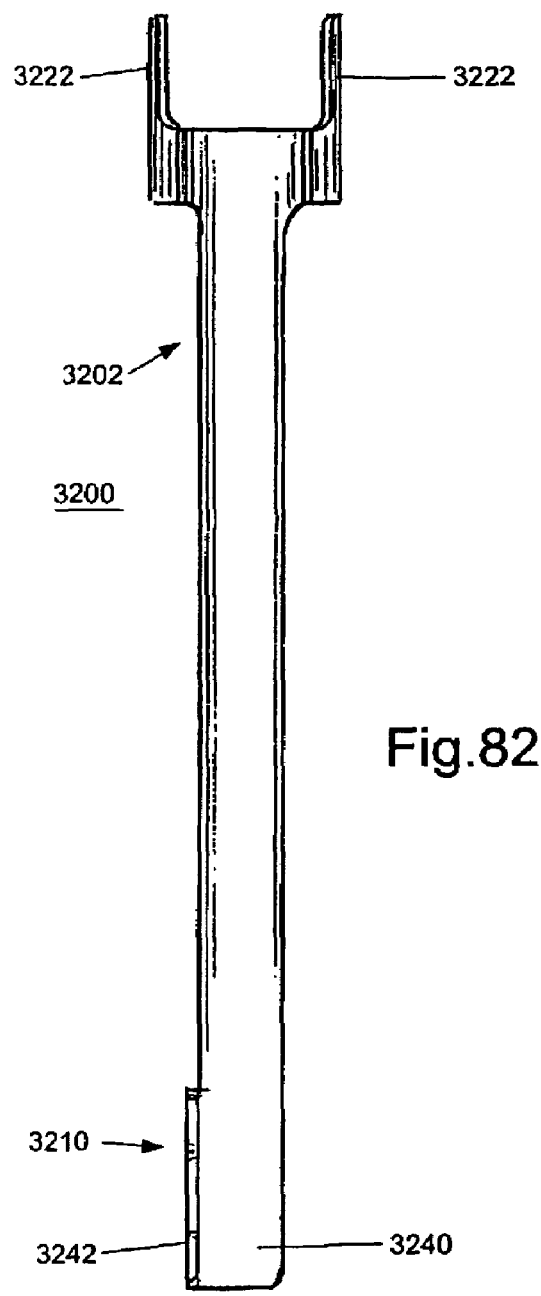

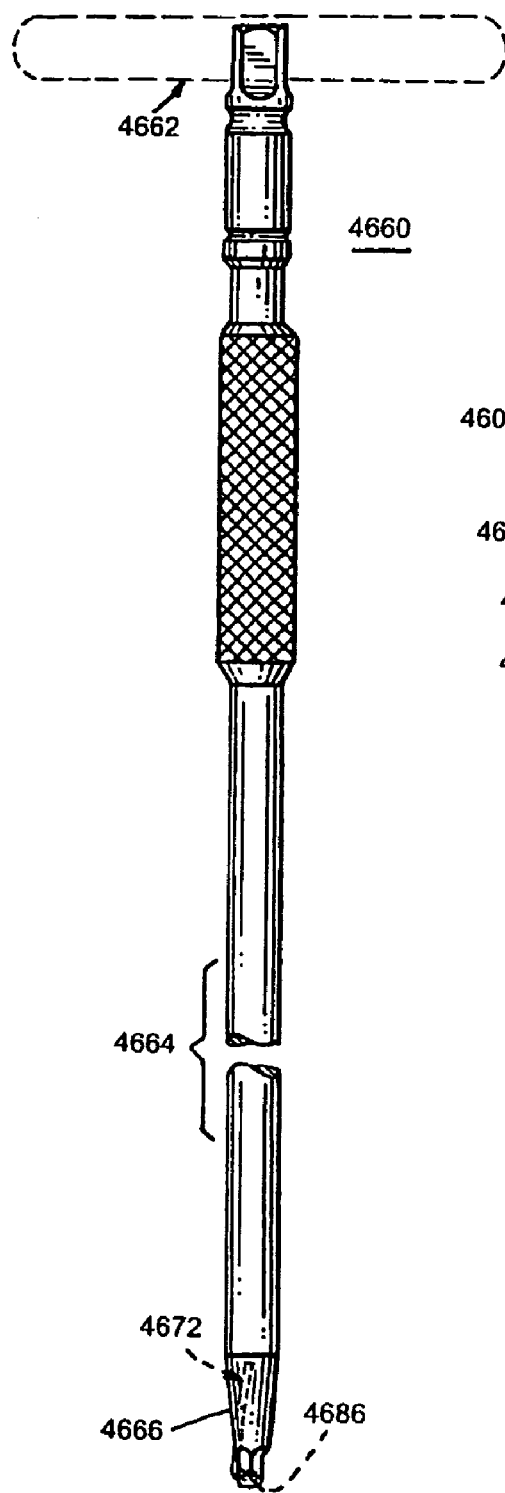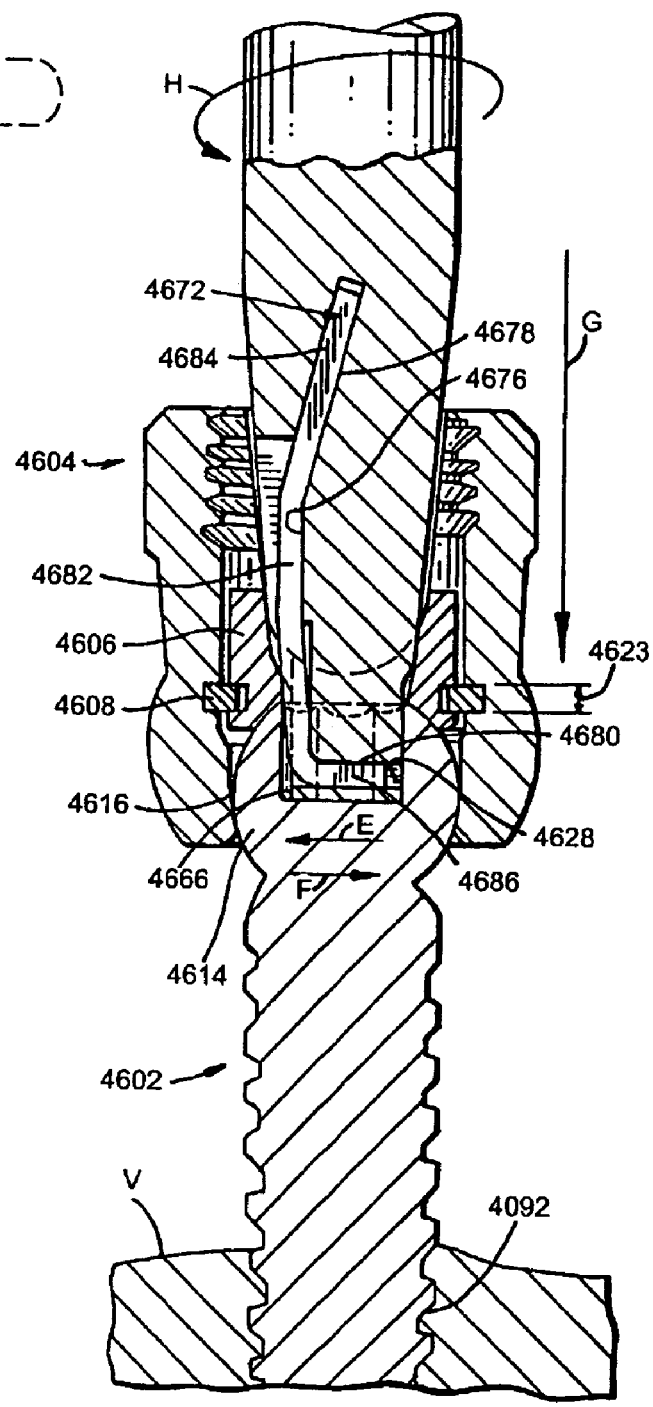

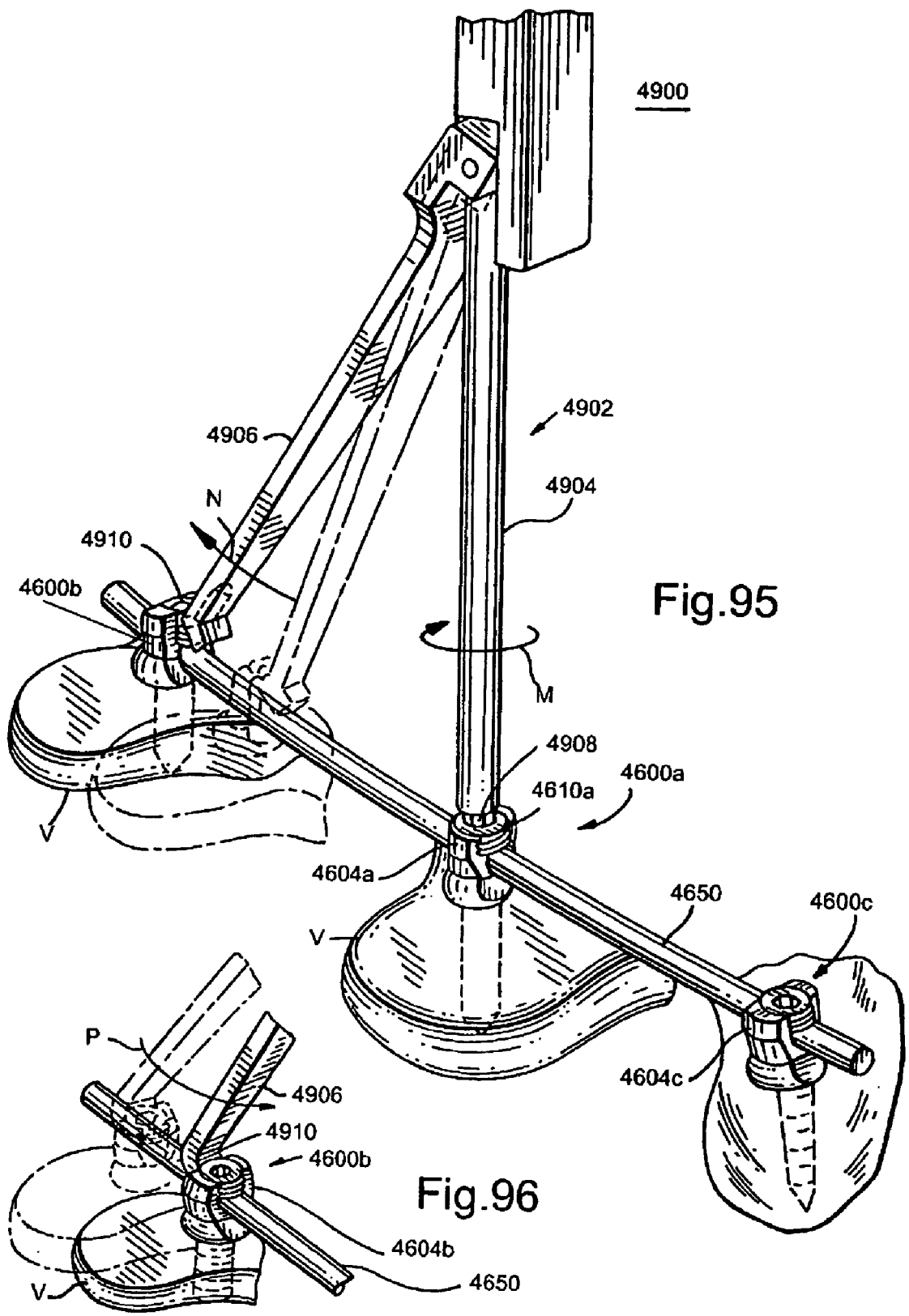

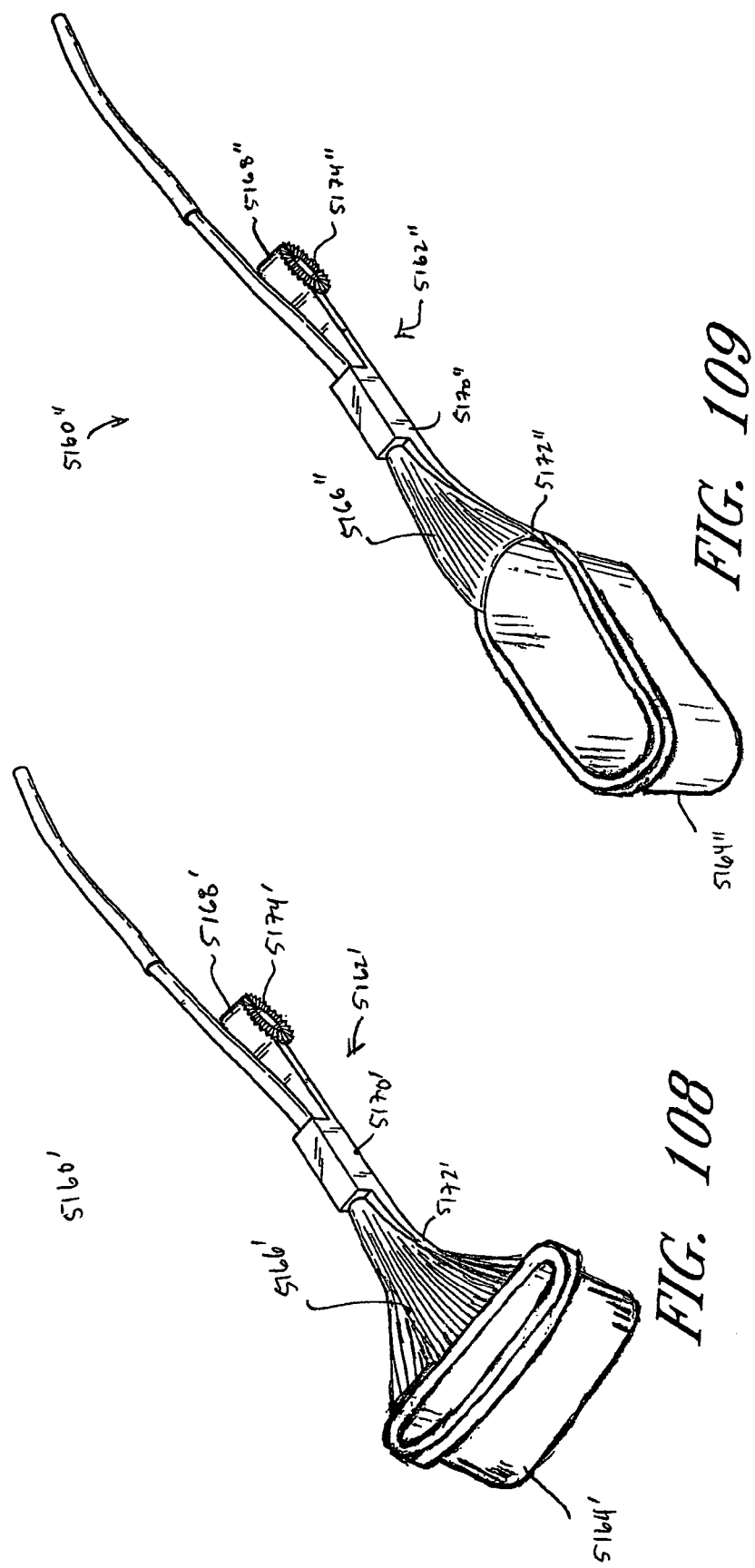

MINIMALLY INVASIVE ACCESS DEVICE AND METHOD

RELATED APPLICATIONS

The present application is based on and claims priority to U.S. Provisional Patent Applications No. 60/497,822 filed Aug. 26, 2003 and 60/497,763 filed Aug. 26, 2003.

BACKGROUND OF THE INVENTION

1. Field of the Invention
2. Description of the Related Art

Spinal surgery presents significant difficulties to the physician attempting to reduce chronic back pain or correct spinal deformities without introducing additional trauma due to the surgical procedure itself. In order to access the vertebrae to perform spinal procedures, the physician is typically required to make large incisions and cut or strip muscle tissue surrounding the spine. In addition, care must be taken not to injure nerve tissue in the area. Consequently, traditional surgical procedures of this type carry high risks of scarring, pain, significant blood loss, and extended recovery times.

Apparatuses for performing minimally invasive techniques have been proposed to reduce the trauma of posterior spinal surgery by reducing the size of the incision and the degree of muscle stripping in order to access the vertebrae. One such apparatus provides a constant diameter cannula which is made narrow in order to provide a small entry profile. As a result, the cannula provides minimal space for the physician to observe the body structures and manipulate surgical instruments in order to perform the required procedures. A narrow cannula is typically inconvenient if not insufficient to perform many spinal procedures, some of which require visualization of two or more vertebrae and introduction of various components and tools for applying such components.

Also, such a cannula is ineffective in procedures where the surgical site is an elongate site, extending between two adjacent vertebrae. While a certain length is needed to span the distance between the vertebrae, a corresponding width is not required in order to insert components for treatment and tools. Accordingly, either more adjacent tissue must be exposed than needed or a second cannula must be inserted. In either case, the benefits of a minimally invasive procedure are lessened.

SUMMARY OF THE INVENTION

In one embodiment a device for retracting tissue provides access to a spinal location within a patient. The device has an elongate body that has a proximal end and a distal end. The elongate body has a length between the proximal and distal ends such that the distal end can be positioned inside the patient adjacent the spinal location. The elongate body has a generally oval shaped proximal portion and an expandable distal portion. A passage extends through the elongate body between the proximal and distal ends. The passage is defined by a smooth metal inner surface extending substantially entirely around the perimeter of the passage between the proximal and distal ends. The elongate body is expandable between a first configuration sized for insertion into the patient and a second configuration wherein the cross-sectional area of the passage at the distal end is greater than the cross-sectional area of the passage at the proximal end.

In another embodiment, a device provides access to a surgical location within a patient. The device has an elongate body that has a proximal end, a distal end, and an inner surface. The inner surface defines a passage that extends through the elongate body. Surgical instruments can be inserted through the passage to the surgical location. The elongate body is capable of having a configuration when located within the patient wherein the cross-sectional area of the passage at a first location is greater than the cross-sectional area of the passage at a second location. The first location is distal to the second location. The passage is capable of having an oblong shaped cross section between the second location and the proximal end.

In another embodiment, a device provides access to a surgical location within a patient. The device has an elongate body that has a proximal end, a distal end, and an inner surface. The inner surface defines a passage that extends through the elongate body. Surgical instruments can be inserted through the passage to the surgical location. The elongate body is expandable from a first configuration to a second configuration when located within the patient. In the second configuration the cross-sectional area of the passage at a first location is greater than the cross-sectional area of the passage at a second location. The first location is distal to the second location. The passage is capable of having a generally oval shaped cross section between the second location and the proximal end.

In another embodiment, a device provides access to a surgical location within a patient. The device has an elongate body that has a proximal end, a distal end, and an inner surface. The inner surface defines a passage that extends through the elongate body. Surgical instruments can be inserted through the passage to the surgical location. The elongate body is capable of having a configuration when inserted within the patient wherein the cross-sectional area of the passage at a first location is greater than the cross-sectional area of the passage at a second location. The first location is distal to the second location. The passage is capable of having a cross section between the second location and the proximal end. The cross section is defined by first and second generally parallel opposing side portions and first and second generally arcuate opposing side portions.

In another embodiment, a method for accessing a surgical location within a patient comprises providing a device that has an elongate body. The elongate body has a proximal end, a distal end, and an inner surface. The inner surface defines a passage extending through the elongate body. Surgical instruments can be inserted through the passage to the surgical location. The passage is capable of having an oblong shaped cross section between the second location and the proximal end. The elongate body has an expanded configuration. The elongate body is configured for insertion into the patient. The device is inserted into the patient to the surgical location. The device is expanded to the expanded configuration.

In another embodiment, a device provides access to a surgical location within a patient. The device has an elongate body that has a proximal end, a distal end, and an inner surface. The inner surface defines a passage that extends through the elongate body. Surgical instruments can be inserted through the passage to the surgical location. The elongate body is capable of having a configuration when located within the patient wherein the cross-sectional area of the passage at a first location is greater than the cross-sectional area of the passage at a second location. The first location is distal to the second location. A lighting element is coupled with the elongate body to provide light to the surgical location.

BRIEF DESCRIPTION OF THE DRAWINGS

The foregoing and other features of the present invention will become more apparent to one skilled in the art upon consideration of the following description of the invention and the accompanying drawings in which:

FIG. 9 is a schematic view taken along line 9-9 in FIG. 6 showing part of the support apparatus of FIG. 6;

FIG. 10 is a schematic view taken along line 10-10 in FIG. 6 with parts removed;

FIG. 15 is a perspective view of the support apparatus of FIG. 6 looking at the support apparatus from an angle different than FIG. 13;

FIG. 16 is a perspective view of the support apparatus of FIG. 6 looking at the support apparatus from an angle different than FIGS. 14 and 15;

FIG. 20 is a view further illustrating parts shown in FIG. 10;

FIG. 21 is a view taken approximately along line 21-21 of FIG. 20;

FIG. 22 is a schematic view showing the support apparatus with an associated known mechanical arm;

FIG. 28 is a schematic view taken along line 28-28 of FIG. 27;

FIG. 29 is an exploded schematic view of part of the assembly of FIG. 27;

FIG. 30 is an exploded view of part of a cutting tool according to another embodiment;

FIG. 31 is an assembled view of part of the cutting tool of FIG. 30;

FIG. 38 is a perspective view of a cannula or expandable conduit in an enlarged configuration according to another embodiment.

FIG. 39 is an enlarged sectional view of the expandable conduit of FIG. 38 taken along lines 39-39 of FIG. 38;

FIG. 40 is a sectional view of the expandable conduit of FIG. 38 taken along lines 40-40 of FIG. 38;

FIG. 41 is a perspective view of a cannula or expandable conduit in an enlarged configuration according to another embodiment;

FIG. 42 is an enlarged sectional view of the expandable conduit of FIG. 41 taken along lines 42-42 of FIG. 41;

FIG. 43 is a sectional view of the expandable conduit of FIG. 41 taken along lines 43-43 of FIG. 41;

FIG. 44 is a view of a portion of a cannula or expandable conduit according to another embodiment;

FIG. 45 is a view of a portion of a cannula or expandable conduit according to another embodiment;

FIG. 51 is a perspective view with parts separated of further apparatus according to another embodiment;

FIG. 53 is a side view of the apparatus of FIG. 51 illustrated with other apparatus;

FIG. 54 is an enlarged perspective view of a component of the apparatus of FIG. 51;

FIG. 57 is a perspective view of a spinal implant or fusion device constructed according to another embodiment showing a first side surface of the spinal implant;

FIG. 58 is a perspective view of the spinal implant of FIG. 57 showing a second side surface of the spinal implant;

FIG. 59 is a plan view of the spinal implant of FIG. 57 showing an upper surface of the spinal implant;

FIG. 60 is a side view of the spinal implant of FIG. 57 showing the first side surface;

FIG. 61 is a cross-sectional view of the spinal implant taken along the line 61-61 in FIG. 60;

FIG. 71 is a side view of an apparatus according to another embodiment;

FIG. 72 is a front view of the apparatus of FIG. 71;

FIG. 81 is a side view, similar to FIG. 71, of another apparatus;

FIG. 82 is a front view, similar to FIG. 74, of the embodiment of FIG. 81;

FIG. 87 is a perspective view of a surgical instrument according to another embodiment;

FIG. 88 is an enlarged sectional view of the apparatus of FIGS. 85-87, illustrating a further stage of the procedure;

FIG. 95 is an enlarged view in partial section illustrating another stage in the procedure in according to another embodiment;

FIG. 96 is a reduced scale view in partial section illustrating yet another stage in the procedure according to another embodiment;

FIG. 108 is a perspective view of another embodiment of a lighting element; and

FIG. 109 is a perspective view of another embodiment of a lighting element.

DETAILED DESCRIPTION OF THE PREFERRED EMBODIMENT

Figure 1:
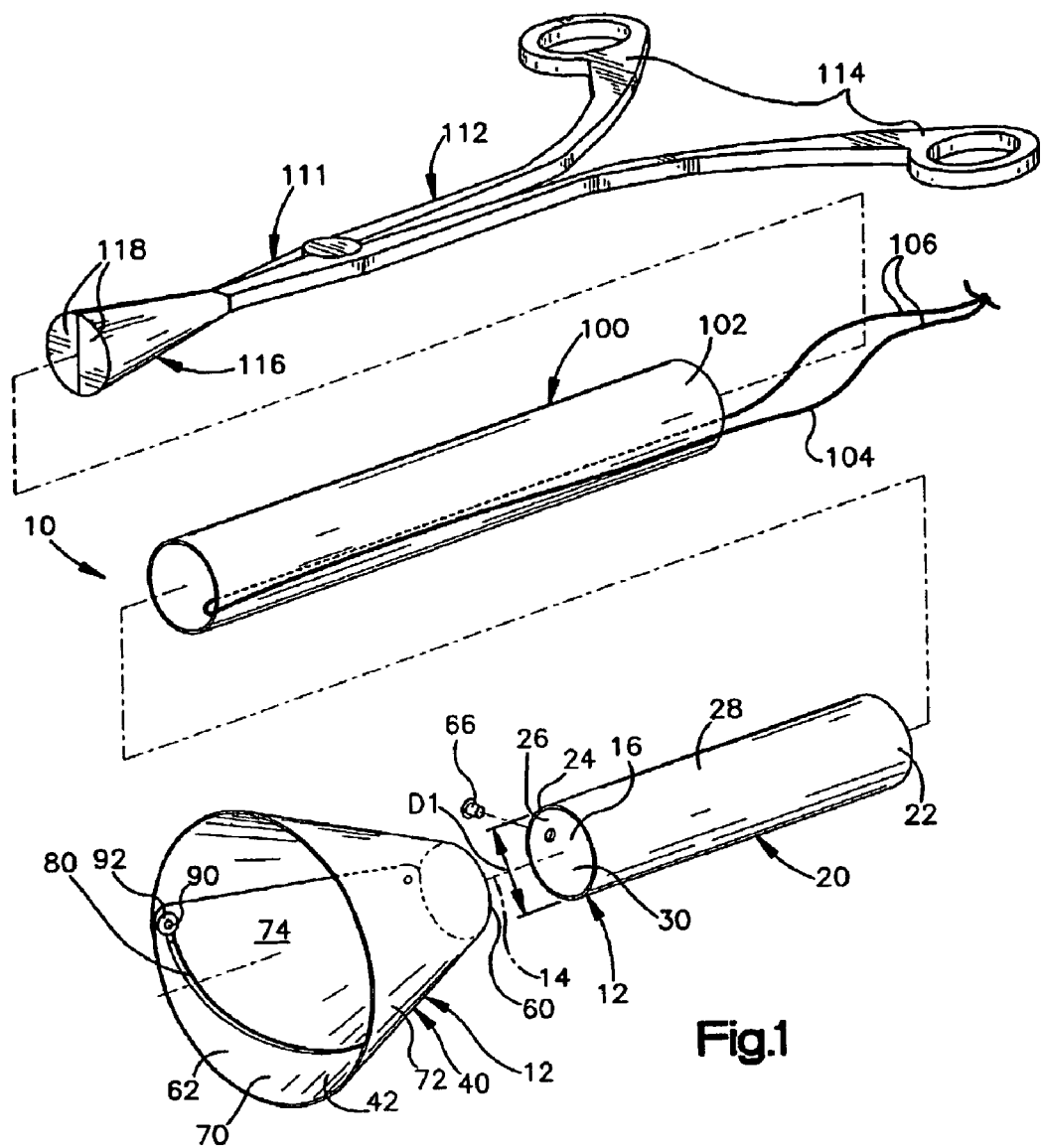
FIG. 1 is an exploded perspective view of a surgical cannula according to one embodiment of the present invention, the cannula being shown in an expanded condition.

The application is directed to surgical systems that may include a device for providing minimally invasive access at a surgical site and a variety of tools that can be used to perform various procedures at the surgical site. Also disclosed herein are a number of components, e.g., implants, that may be applied to the spine at various spinal locations in connection with such procedures. Various embodiments of access devices and related components that are particularly advantageous in procedures that are convenient to perform at an elongate surgical site are discussed below in connection FIGS. 97-109. However, a variety of advantageous combinations may be provided whereby features of these embodiments are combined with features of other embodiments described hereinbelow.

One embodiment of a surgical system described hereinbelow is particularly well suited for performing various methods for fixing the vertebrae of a patient at a surgical site. As discussed more fully below, such a surgical system generally includes an access device, such as an expandable cannula or conduit, an adjustable support for the access device, a variety of surgical instruments, a viewing device, a lighting element, a spinal implant or fusion device, and a vertebral fixation assembly. Many of these components, e.g., the instruments, viewing device, spinal implants, and fixation assembly components, are configured to be inserted through the access device to the surgical site.

FIGS. 1-5 illustrate one suitable expandable cannula or conduit 10 constructed for use in a method according to one embodiment. The cannula 10 is a tubular structure 12 centered on an axis 14. The tubular structure 12 defines a passage 16 through the cannula 10. Surgical instruments are inserted into the body during surgery through the passage 16.

The tubular structure 12 comprises a first tubular portion 20 and a second tubular portion 40 attached to the first tubular portion. The first tubular portion 20 is preferably made of a length of stainless steel tubing, but could alternatively be made of another suitable material. The first tubular portion 20 has a proximal end 22 and a distal end 24. Parallel cylindrical inner and outer surfaces 26 and 28, respectively, extend between the ends 22, 24 of the first tubular portion 20. The inner surface 26 defines a first passage portion 30 of the passage 16 through the cannula 10. The first passage portion 30 has a diameter D1 that is preferably in the range from 10 mm to 30 mm.

The second tubular portion 40 of the tubular structure 12 is attached to the distal end 24 of the first tubular portion 20. The second tubular portion 40 is preferably made from stainless steel, but could alternatively be made from another suitable material.

Figure 4:
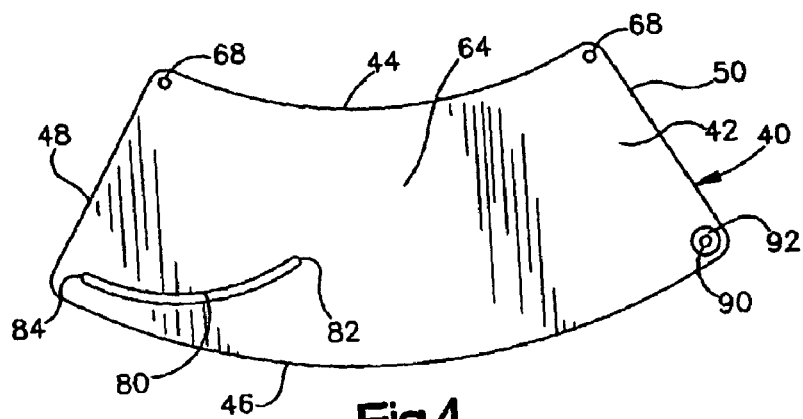
FIG. 4 is a rollout view of a part of the cannula of FIG. 1.
Figure 3:
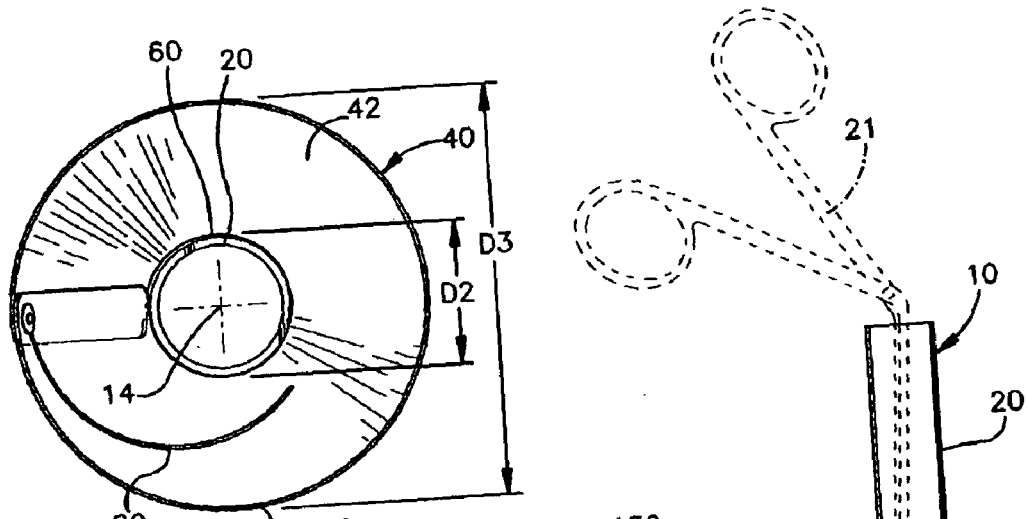
FIG. 3 is a schematic end view showing the cannula of FIG. 1 in the expanded condition.
Figure 5:
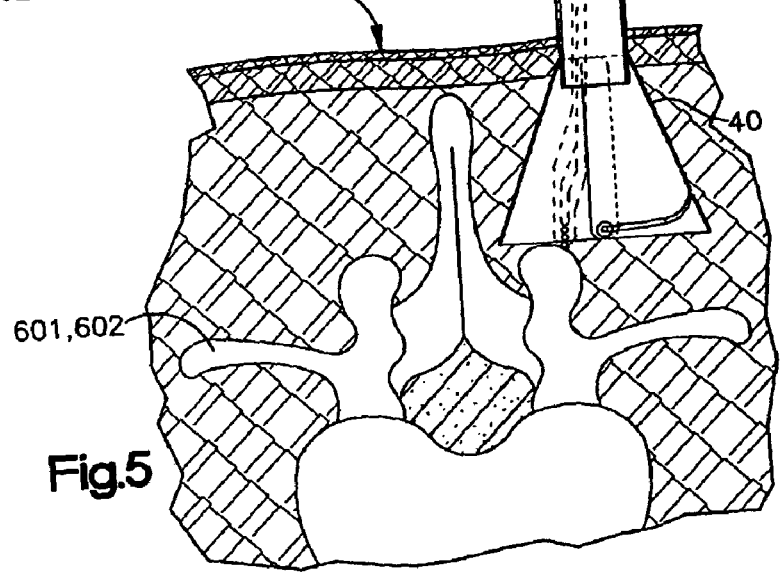
FIG. 5 is a schematic sectional view of the cannula of FIG. 1 during a surgical procedure.
Figure 6:
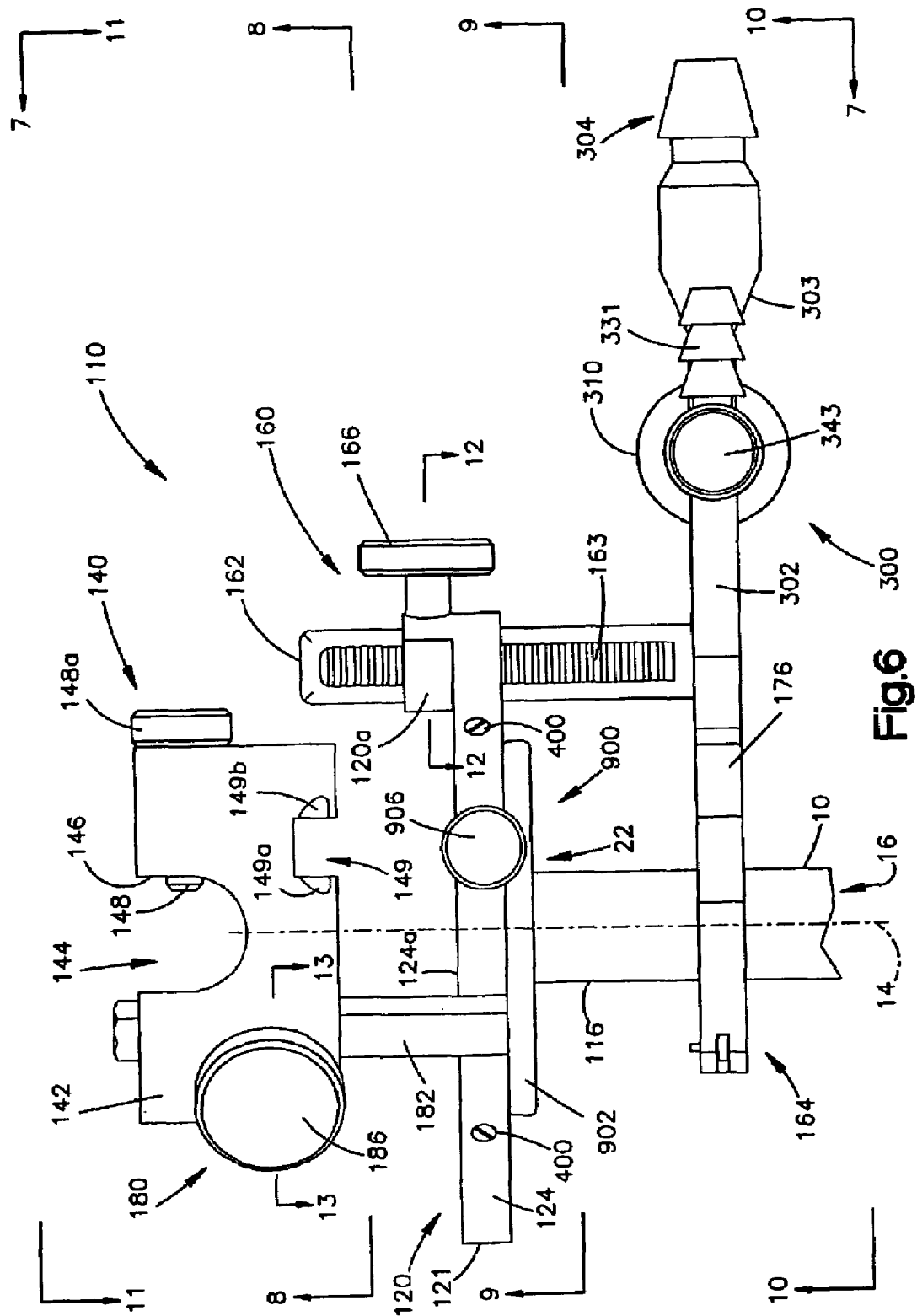
FIG. 6 is a schematic view of a support apparatus constructed according to another embodiment.
Figure 7:
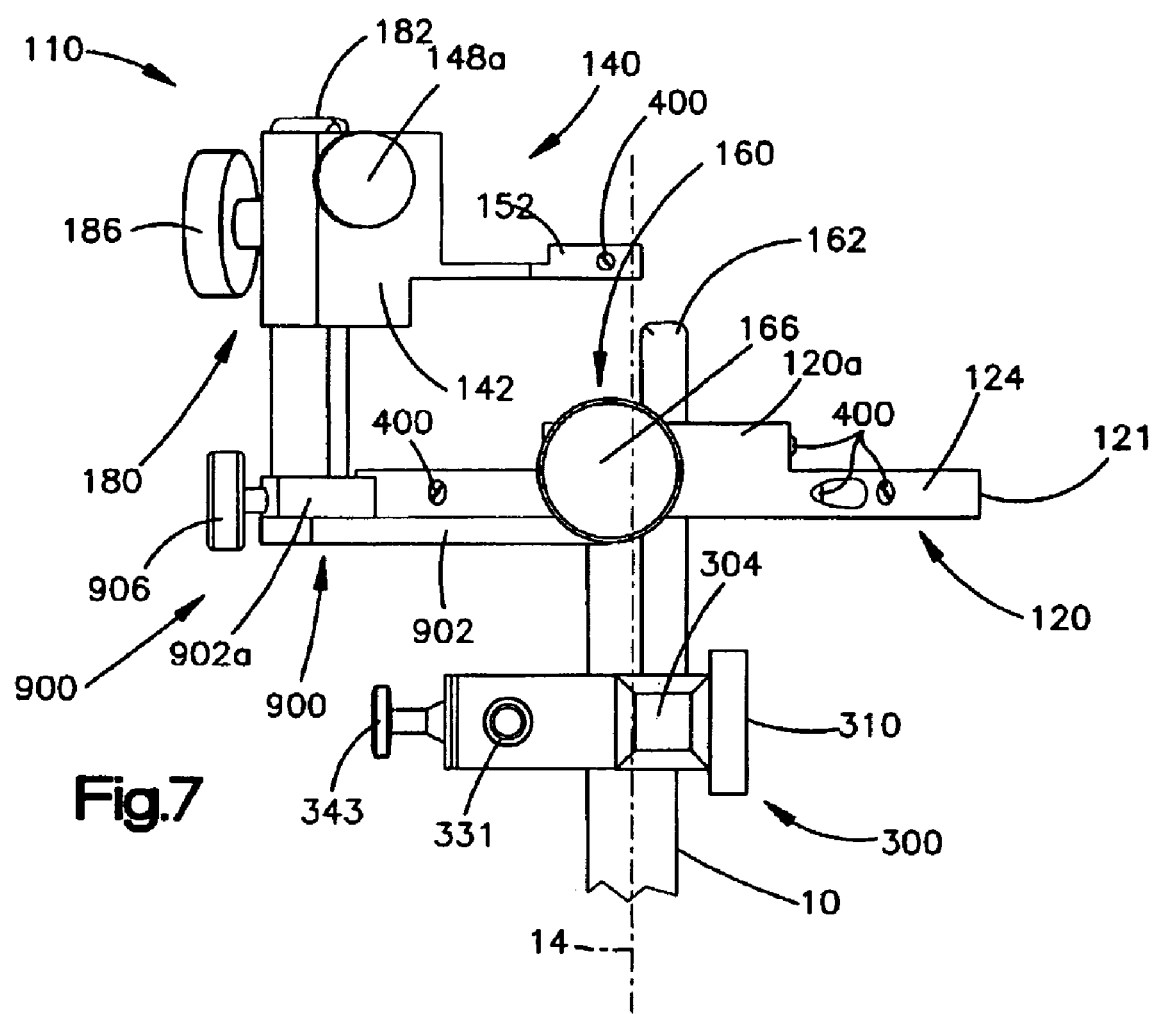
FIG. 7 is a schematic view taken along line 7-7 in FIG. 6.
Figure 8:
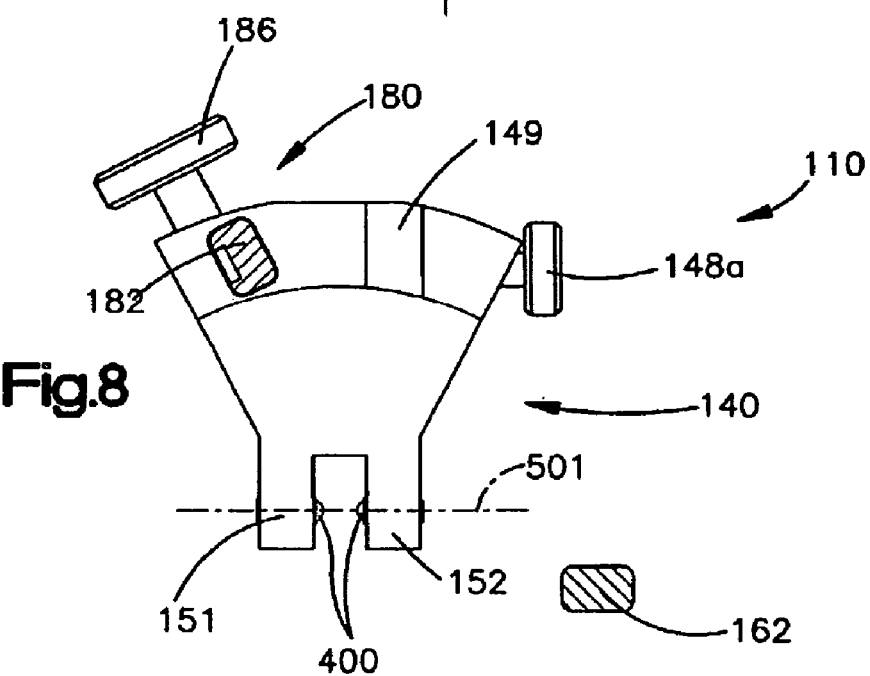
FIG. 8 is a schematic view taken along line 8-8 in FIG. 6 showing part of the support of FIG. 6.
Figure 11:
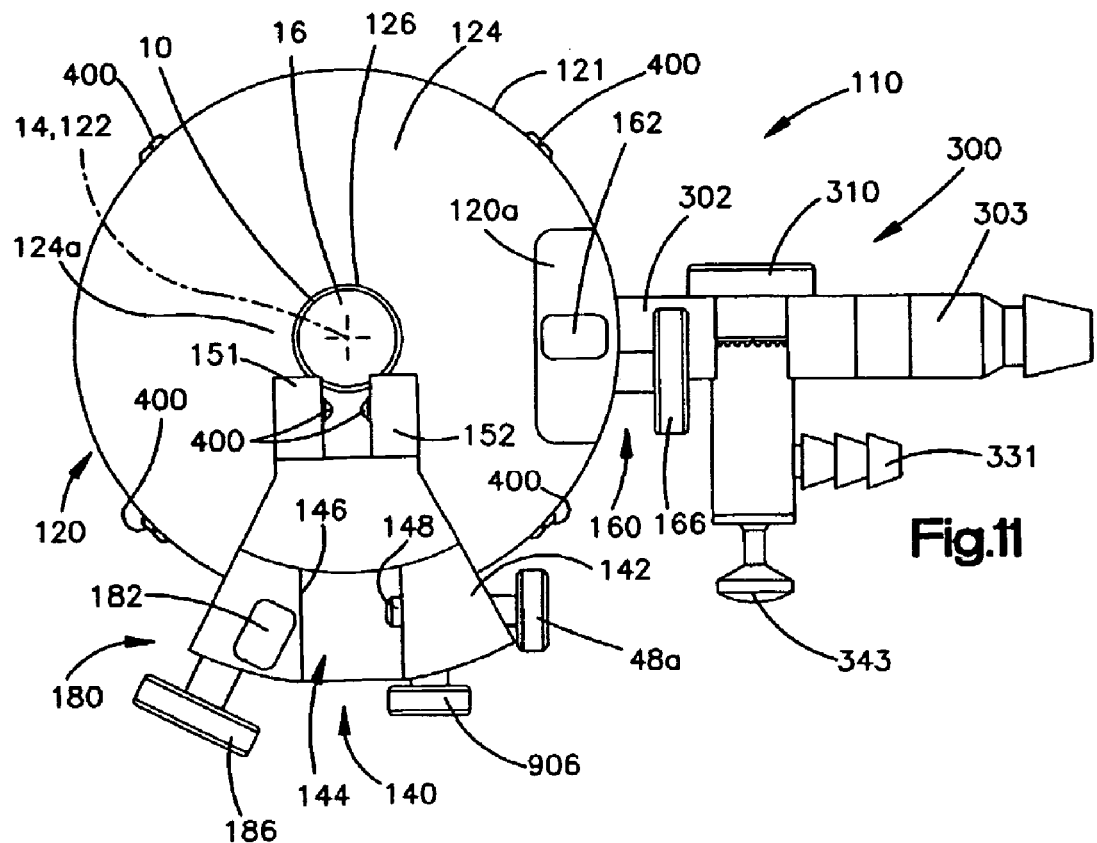
FIG. 11 is a schematic view taken along line 11-11 in FIG. 6.
Figure 14:
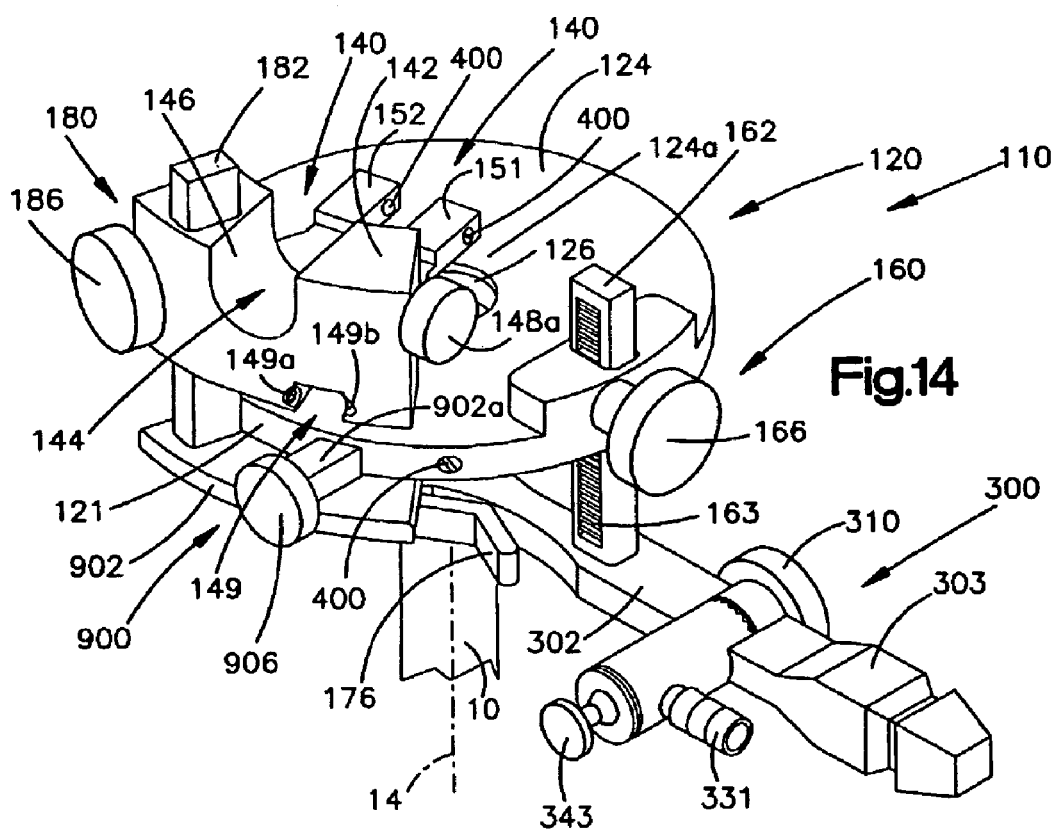
FIG. 14 is a perspective view of the support apparatus of FIG. 6.

As best seen in the rollout view of FIG. 4, the second tubular portion 40 comprises an arcuate segment 42 of sheet stock. The arcuate segment 42 includes first and second arcuate edges 44 and 46, respectively, and first and second planar edges 48 and 50, respectively. The first and second planar edges 48 and 50 are rolled in an overlapping manner to form the tubular configuration of the second tubular portion 40.

When the second tubular portion 40 has been rolled into its tubular configuration, the first and second arcuate edges 44 and 46 define oppositely disposed first and second ends 60 and 62 (FIGS. 1 and 2), respectively, of the second tubular portion. The first and second ends 60 and 62 are connected by a central portion 64. The first end 60 of the second tubular portion 40 is attached to the distal end 24 of the first tubular portion 20 by a single fastener, such as a rivet 66. The rivet 66 extends through two aligned apertures 68 (FIG. 4) at the first end 60 of the second tubular portion 40. The first end 60 of the second tubular portion 40 is pivotable about the rivet 66.

The second tubular portion 40 includes parallel inner and outer surfaces 70 and 72 (FIGS. 1 and 2), respectively, extending between the first and second ends 60 and 62. The inner surface 70 defines a second passage portion 74 of the passage 16 through the cannula 10 that extends as a continuation of the first passage portion 30 in the first tubular portion 20.

An arcuate slot 80 is formed in the second tubular portion 40 and extends between the inner and outer surfaces 70 and 72 of the second tubular portion. The arcuate slot 80 extends along a curvilinear path in the central portion 64 of the second tubular portion 40 toward the second end 60 of the second tubular portion. The arcuate slot 80 has a first terminal end 82 located in the central portion 64 of the second tubular portion 40. A second terminal end 84 of the arcuate slot 80 is located adjacent the intersection of the second arcuate edge 46 and the first planar edge 48 of the arcuate segment 42.

A guide pin 90 is attached to the inner surface 70 of the second tubular portion 40 adjacent the intersection of the second arcuate edge 46 and the second planar edge 50. In the tubular configuration of the second tubular portion 40, the guide pin 90 is located in the arcuate slot 80 and is movable along the curvilinear path of the arcuate slot. A washer 92 is secured to an inner end of the guide pin 90 to retain the guide pin in the arcuate slot 80.

Figure 2:
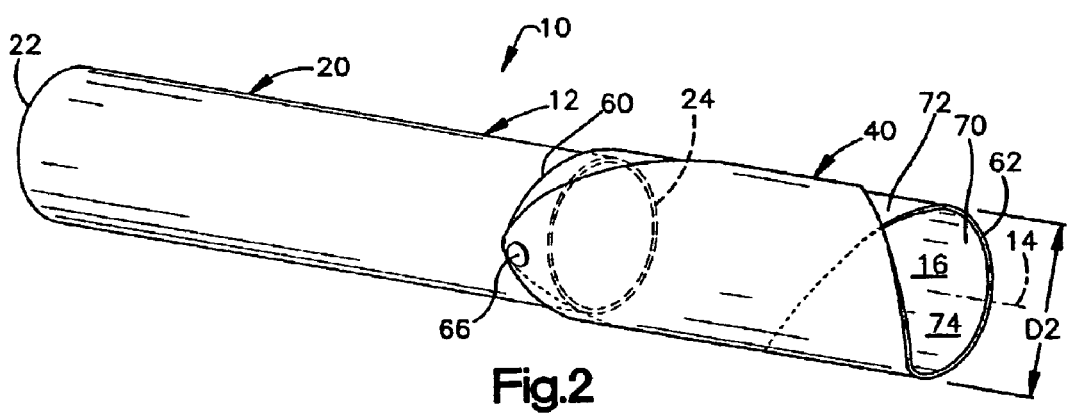
FIG. 2 is a perspective view of the cannula of FIG. 1 with parts removed for clarity, the cannula being shown in a contracted condition.

The second tubular portion 40 of the tubular structure 12 is expandable from a contracted condition shown in FIG. 2 to an expanded condition shown in FIG. 1. In the contracted condition, the guide pin 90 is located in the first terminal end 82 of the arcuate slot 80 in the second tubular portion 40 and the second passage portion 74 defined by the second tubular portion is cylindrical in shape. The second passage 74 has a generally constant diameter D2 (FIGS. 2 and 3) that is approximately equal to the diameter D1 of the first tubular portion 20. Thus, the cross-sectional area of the second passage portion 74 at the second end 62 of the second tubular portion 40, which is function of the diameter D2, is approximately the same as the cross-sectional area at the first end 60 of the second tubular portion and is approximately the same as the cross-sectional area of the first passage portion 30 in the first tubular portion 20.

In the expanded condition, the guide pin 90 is located in the second terminal end 84 of the arcuate slot 80 in the second tubular portion 40 and the second tubular portion has a conical configuration. At the second end 62 of the second tubular portion 40, the second passage portion 74 has a diameter D3 (FIG. 3) that is larger than the diameter D2 of the second passage portion at the first end 60. Preferably, the diameter D3 of the second passage portion 74 at the second end 62 of the second tubular portion is 40% to 80% greater than the diameter D1 of the second passage portion at the first end 60. Thus, in the expanded condition, the cross-sectional area of the second passage portion 74 at the second end 62 of the second tubular portion 40, which is function of the diameter D3, is 16% to 64% greater than the cross-sectional area of the second passage portion at the first end 60 of the second tubular portion. In the expanded condition, the cross-sectional area of the second passage portion 74 at the second end 62 of the second tubular portion 40 is large enough to overlie a major portion of at least two adjacent vertebrae.

The cannula 10 includes an outer layer 100 (FIG. 1) for maintaining the second tubular portion 40 of the cannula in the contracted condition. It is contemplated that other suitable means for maintaining the second tubular portion 40 in the contracted condition could be employed. In accordance with a preferred embodiment of the present invention, the outer layer 100 comprises a section of plastic tubing 102 which is heat shrunk over both the first and second tubular portions 20 and 40 to hold the second tubular portion in the contracted condition.

In addition, a loop of polyester string 104 for tearing the heat shrunk tubing 102 is wrapped around the heat shrunk tubing so that it extends both underneath and on top of the tubing. An outer end 106 of the string 104 extends beyond the tubing 102.

FIG. 1 shows an actuatable device 111 for expanding the second tubular portion 40 from the contracted condition to the expanded condition. In accordance with a preferred embodiment, the actuatable device 111 comprises a manually operated expansion tool 112. The expansion tool 112 resembles a common pair of scissors and has a pair of legs 114 pivotally connected to one another. The expansion tool 112 includes a frustoconical end section 116 formed by a pair of frustoconical halves 118. Each of the frustoconical halves 118 extends from a respective one of the legs 114 of the expansion tool 112. It is contemplated that other suitable means for expanding the second tubular portion 40 toward the expanded condition could be employed, such as an inflatable balloon (not shown).

During an endoscopic surgical procedure, the cannula 10 is inserted into the body of a patient in the contracted condition. The outer end 106 of the string 104 is then manually pulled on by the surgeon. Pulling on the string 104 tears the heat shrunk tubing 102 most of the way along the heat shrunk tubing, which frees the second tubular portion 40 for expansion. The heat shrunk tubing 102, in its torn condition, remains attached or secured to the first tubular portion 20.

Next, the expansion tool 112 is inserted into the passage 16 in the cannula 10 until the frustoconical end section 114 is located at the second end 62 of the second tubular portion 40. The legs 114 of the expansion tool 112 are manually separated, causing the frustoconical halves 118 to separate also. As the halves 118 separate, a radially outward directed force is exerted on the inner surface 70 of the second tubular portion 40 by the halves 118, causing the second tubular portion to expand toward the expanded condition. Under the force of the expanding expansion tool 112, the guide pin 90 slides from the first terminal end 82 of the arcuate slot 80 to the second terminal end 84 of the arcuate slot to permit the expansion of the second tubular portion 40. The expansion tool 112 can be rotated about the axis 14 to ensure that the second tubular portion 40 of the cannula 10 is completely expanded to the expanded condition. The expansion tool 112 is then collapsed and removed so that one or more surgical instruments (indicated schematically at 21 in FIG. 5) and a viewing element can be received through the cannula 10 and inserted into a patient's body 130. The expandable second tubular portion 40 of the cannula 10 provides a significantly larger working area for the surgeon inside the body 130 within the confines of the cannula.

The expanded tubular portion 40 can dilate and locally retract and separate spinalis muscle and soft tissues from the vertebrae thereby creating an endoscopic operating field at the surgical site. This endoscopic operating field within the spinal muscles differs from arthroscopic, laparoscopic, or cystoscopic working spaces in that there is no physiologic space or defined tissue plane that can be insufflated with air or distended with fluid.

FIGS. 6-23 illustrate one suitable support apparatus for use in a method according to one embodiment. The support apparatus 110 includes a first support 120, a second support 140, a first adjustment mechanism 160, a second adjustment mechanism 180, and a third adjustment mechanism 900.

As viewed in FIGS. 9 and 15, the first support 120 is associated with the cannula 10 and has a circular perimeter 121. The perimeter 121 has a center 122 located on the axis 14. The first support 120 comprises a circular platform, or disk 124, which has a circular opening 126 in the central area of the disk 124 for receiving the proximal end 22 of the cannula 10. The circular opening 126 has a center located on the axis 14. The proximal end 22 of the cannula 10 can be easily inserted into and removed from the opening 126. The disk 124 has a projection portion 120a, which is located adjacent the perimeter 121 of the disk 124. The disk 124 has an upper circular surface area 124a, which surrounds the opening 126.

As viewed in FIG. 15, the second support 140 supports a viewing device 200 including a camera head 201 and an endoscope 202 with a rod and lens assembly 203, herein referred to as a viewing element, extending down through the passage 16 of the cannula 10. With reference to FIGS. 15 and 16, the second support 140 includes a body 142 having an opening 144 through which the viewing device 200 extends and a clamp 146 for clamping the viewing device 200 to the body 142 in the opening 144. The clamp 146 includes a threaded set screw 148 for securing the viewing device 200 to the body 142. The set screw 148 has a manually rotatable knob 148a and a stem threaded into the body 142. When rotated, the screw 148 moves axially relative to the body 142 to clamp or release the viewing device 200 depending on the direction of rotation of the screw 148.

The body 142 of the second support 140 further includes two extension arms 151, 152 (FIG. 8) for supporting the endoscope 202. Each extension arm 151, 152 includes a threaded bore for receiving a resilient detent member, or ball plunger 400.

Figure 17:
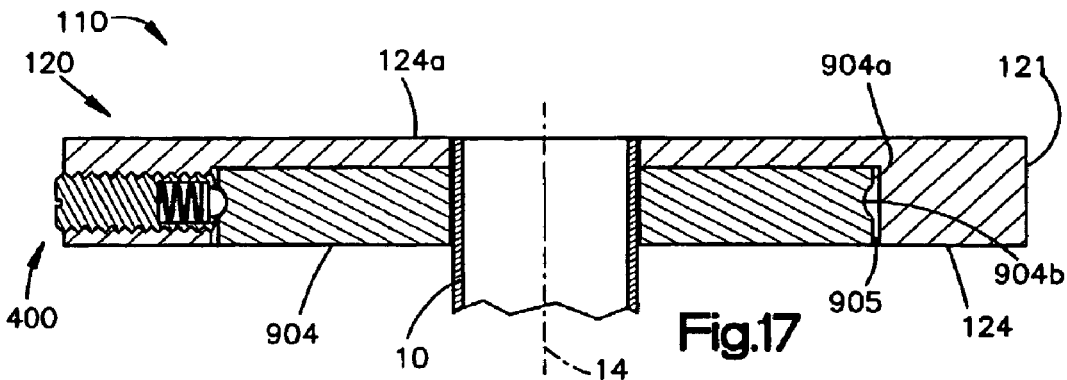
FIG. 17 is a sectional view taken approximately along line 17-17 of FIG. 9.
Figure 18:
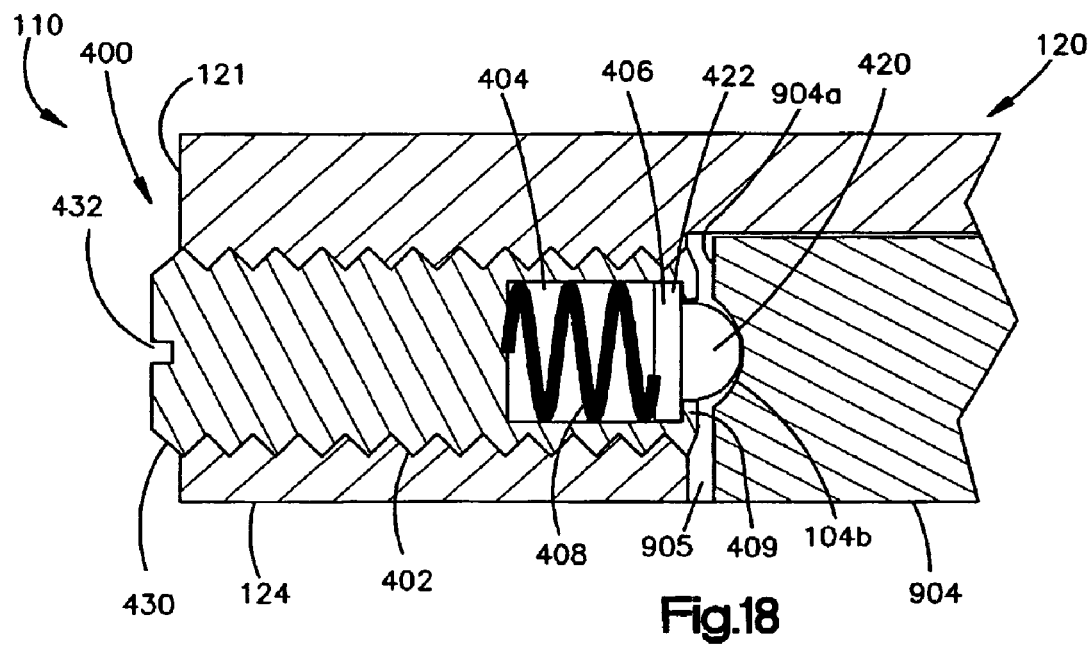
FIG. 18 is an enlarged view of a part of FIG. 17.

As viewed in FIGS. 17 and 18, a ball plunger 400 is illustrated at another location in the support apparatus 110. Each ball plunger 400, including those in the extension arms 151, 152, has an externally threaded tubular body 402 with a cylindrical cavity 404 located therein. The cavity 404 houses a projection 406 and a coiled spring 408. The projections 406 of the two ball plungers 400 of the extension arms 151, 152 are spherical detent members 420 in the form of balls (not shown). The spring 408 urges each projection 406 against a lip portion 409 of the body 402. The lip portion 409 is located at one end of the cavity 404. As shown in FIG. 18, the other ball plungers 400 of the apparatus 10 have projections 406 with hemispherical extensions 420 and shoulder portions 422.

As viewed in FIG. 15, the endoscope 202 has corresponding hemispherical recesses (not shown) for receiving the spherical detent members (balls) of the ball plungers 400 which are located in extension arms 151, 152. The springs 408 will compress in each ball plunger 400 in each extension arm 151, 152 and the spherical detent members will move inward of each cavity 404 and then spring back into the hemispherical recesses in the endoscope 202, as the endoscope 202 is inserted between the extension arms 151, 152. The entire viewing device 200 will thus be secured between the extension arms 151, 152, but may be removed by overcoming the force of the spherical detent members of each ball plunger 400 in the extension arms 151, 152.

The ball plunger 400 further includes a head portion 430 with a slot 432 for engaging a tool, such as a screwdriver. The ball plunger 400 may be threadedly adjusted within the threaded bore of either extension arm 151, 152 to alter the distance that the spherical detent member 420 projects away from the extension arms 151, 152 (toward each other). This distance, along with the stiffness of each spring 408, will determine the holding force by which the endoscope 202 is secured between the extension arms 151, 152.

The first adjustment mechanism 160 provides for relative axial adjustment of the cannula 10 and the first support 120 along the axis 14. The first adjustment mechanism 160 includes a first toothed rack member 162, a cannula gripper mechanism 164 fixedly connected to the first rack member 162, a first manually adjustable, rotatable knob 166 rotatably carried by the projection portion 120a of the first support 120, and a first gear member 165 (FIG. 12) rotatable by the first knob 166 and in meshing engagement with the teeth 163 of the first rack member 162. The first support 120 and, in particular, the projection portion 120*a*, rotatably carries the first gear member 165 (FIG. 12).

Figure 12:
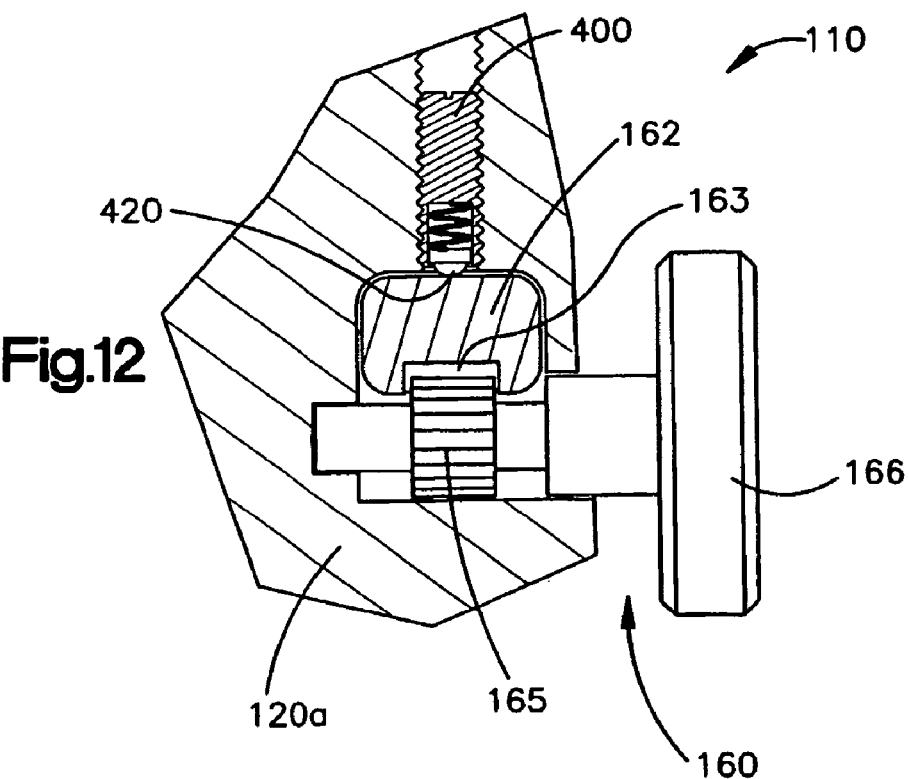
FIG. 12 is a schematic view taken along line 12-12 in FIG. 6 showing part of the support apparatus of FIG. 6.

The first rack member 162 is secured to slide axially within the first support 120 and the projection portion 120*a* by two ball plungers 400 (FIG. 12). One ball plunger 400 is tangentially threaded into a tapered, threaded bore (FIG. 7) in the perimeter 121 of the first support 120 and the other is tangentially threaded into a threaded bore in the projection portion 120*a*. The hemispherical extensions 420 thus frictionally engage a smooth portion (without teeth 163) of the first rack member 162 and bias the first rack member 162 against the first support 120 and the projection portion 120*a*. This biasing also maintains the engagement of the first rack member 162 and the first gear member 165 (FIG. 12).

Figure 19:
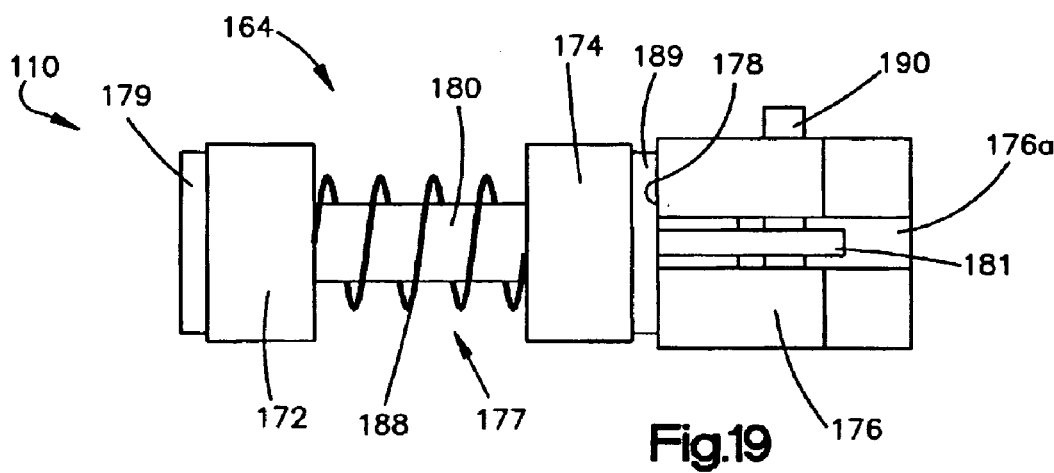
FIG. 19 is a schematic view taken along line 19-19 in FIG. 10 with parts removed.

As viewed in FIGS. 10 and 19, the cannula gripper mechanism 164 includes two gripper arms 172, 174 for clamping against the outer surface of the cannula 10, and a gripper actuating lever 176 for moving the arms 172, 174 into engagement with the outer surface of the cannula 10 and for releasing the arms 172, 174 from engagement with the cannula 10.

As viewed in FIG. 19, the cannula gripper mechanism 164 further includes a support pin 177, a coiled spring 188, a washer 189 with a bore (not shown), and a lock pin 190. The support pin 177 has a head 179, a shaft 180, and an elongate, or flat, end 181 that can mate with the bore in the washer 189. Other suitable structures could be used.

During assembly, the coiled spring 188 is interposed between the arms 172, 174. The flat end 181 of the support pin 177 is inserted through a circular bore in the first clamp arm 172, through the coil of the spring 188, through a circular bore in the second arm 174, and through the bore in the washer 189. The flat end 181 of the support pin 177 is then inserted into a slot 176*a* in the lever 176. The lock pin 190 is inserted through a bore in the lever 176 and through a bore in the flat end 181 of the support pin 177 thereby securing the mechanism 164 together and allowing the lever 176 to rotate about the lock pin 190. A camming surface 178 on the lever 176 adjacent the washer 189 forces the arms 172, 174 together to grip the cannula 10 as the lever 176 is rotated clockwise (as viewed in FIG. 10). Counterclockwise rotation of the lever 176 allows the spring 188 to force the arms 172, 174 apart and releases the cannula 10 from the gripper mechanism 164.

When the gripper mechanism 164 is either gripping the cannula 10 or released from the cannula 10 and the knob 166 is rotated, the disk 124 and parts attached to the disk 124 will move along the axis 14 of the cannula 10 relative to the cannula 10. After the support apparatus 110 is initially lined up with the cannula 10, the viewing device 200 may be positioned on the support apparatus 110 and adjusted along the axis 14 by rotation of knob 166.

The second adjustment mechanism 180 provides axial adjustment of the first and second supports 120, 140 relative to each other along the axis 14. The second adjustment mechanism 180 includes a second toothed rack member 182 connected to the first support 120, a second manually adjustable, rotatable knob 186 rotatably carried by the body 142 of the second support 140, and a second toothed gear member 185 (FIG. 13) rotatable by the second knob 186 and in meshing engagement with the teeth 183 of the second rack member 182. The second support 140, and in particular, the body 142, rotatably carries the second gear member 185 (FIG. 13).

The body 142 of the second support 140 may have a notch 149 which can fit around part 902*a* of the third adjustment mechanism 900 and allow the lower surface of the body 142 to completely abut the disk 124 as the body 142 is brought into an axial position adjacent the disk 124.

Figure 13:
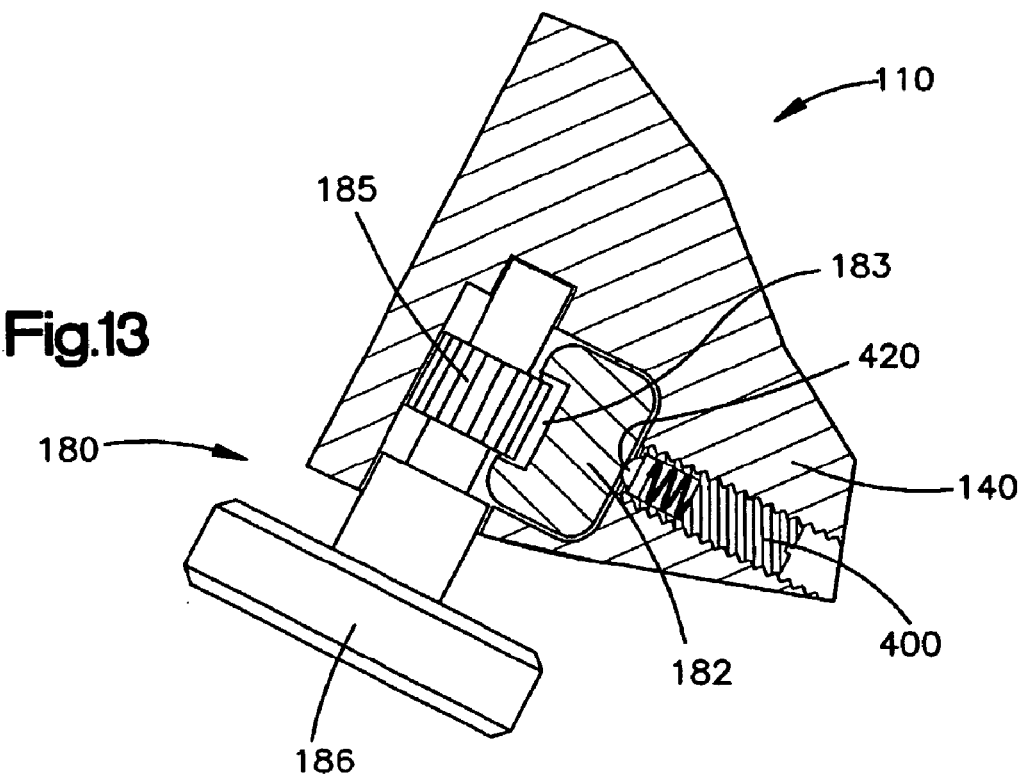
FIG. 13 is a schematic view taken along line 13-13 in FIG. 6 showing part of the support apparatus of FIG. 6.

The second rack member 182 is secured to slide axially within the second support 140 by a ball plunger 400 (FIG. 13). The ball plunger 400 is tangentially threaded into a threaded bore in the side of the notch 149 of the second support 140. The hemispherical extension 420 thus frictionally engages a smooth portion (without teeth 183) of the second rack member 182 and biases the second rack member 182 against the second support 140. The biasing also maintains the engagement of the second rack member 182 and the second gear member 185. Both sides of the notch 149 have tapered portions 149*a*, 149*b* for facilitating insertion of the ball plunger 400 into the threaded bore of the notch 149 of the second support 140. Rotation of the knob 186 causes the body 142 and the viewing device 200 attached thereto to move relative to the cannula 10 and disk 124 along the axis 14.

The third adjustment mechanism 900 provides arcuate, circumferential adjustment of the second support 140 about the axis 14 relative to the first support 120. The third adjustment mechanism 900 includes a wedge-shaped support member 902 (FIG. 9) fixedly connecting the second rack member 182 to a ring member 904 that is rotatably supported by the first support 120 and rotatable about the axis 14 relative to the first support 120 (FIG. 17).

The third adjustment mechanism 900 further includes a third manually adjustable, rotatable knob 906 that is part of a set screw. The set screw is rotatably threaded into a projection portion 902*a* of the support member 902 and is engageable with the circular perimeter 121 of the disk 124 of the first support 120 to lock the support member 902 in an arcuate position relative to the first support 120 and the axis 14.

As viewed in FIGS. 17 and 18, the ring member 904 is supported within a cylindrical, open ended recess 905 of the first support 120. The recess 905 is concentric about the axis 14. The perimeter 904*a* of the ring member 904 has a groove 904*b* for engaging a plurality of ball plungers 400 (preferably four equally spaced apart) in the first support 120. Each of these ball plungers 400 is similar in construction. Each ball plunger 400 is threaded radially into the perimeter 121 of the first support 120 to provide a hemispherical extension 420 extending into the recess 905 of the first support 120.

The ring member 904 thus is biasingly supported within the recess 905 of the first support 120 and can rotatably slide within the recess 905 about the axis 14. The ball plungers 400 operatively support the ring member 904 in the recess 905 of the first support 120. The ring member 904, along with the second support 140 and the second and third adjustment mechanisms 180, 900, can be easily removed from the recess 905 for cleaning, maintenance, etc. of the parts by overcoming the force applied by the ball plungers 400 to the ring member 904. When the knob 906 is rotated to disengage the perimeter 121 of disk 124, the body 142 and parts connected thereto can be manually rotated about the axis 14. This causes the viewing device 200 to rotate about the axis 14 of the cannula 10 and enables the surgeon to view different parts of the surgical sight as desired.

As viewed in FIG. 16, the fixed connections of the first rack member 162 to a support arm 300, the second rack member 182 to the wedge-shaped support member 902, and the support member 902 to the ring member 904 may be made by one or more suitable metal fasteners 290, such as rivets or bolts. The entire support apparatus 110 can be constructed from metal or any other suitable material having sufficient mechanical strength and durability. Certain parts may be made from materials permitting X-rays and other techniques for viewing the surgical sight (i.e., radiolucent parts). Other parts may also be made from non-magnetic materials to reduce electromagnetic interference (i.e., electromagnetic insulating parts).

With reference to FIGS. 10 and 22, the gripper's arms 172, 174 are a part of the support arm 300 for attaching the support apparatus 110 to a mechanical robotic arm 301. The support arm 300 includes an arm portion 302 that is formed integrally with the arms 172, 174. The arms 172, 174 are integrally constructed with the arm portion 302.

The support arm 300 also includes an arm portion 303. The arm portion 303 has an attaching structure 304, including a groove 305, which snaps into a socket in the mechanical arm 301. Detents of any suitable type and designated 306 in the mechanical arm 301, hold the arm portion 303 in position in the socket in the mechanical arm 301. The detents 306 may be controlled by external actuation levers (not shown) on the mechanical arm 301 for manually releasing the arm portion 303 from the mechanical arm 301.

The arm portions 302 and 303 are pivotally connected to each other by a fastener 310. The fastener 310 extends through an opening 311 in the arm portion 302 and threads into a threaded opening 312 in the arm portion 303. When the fastener 310 is released, the arm portions 302, 303 may pivot relative to each other about a pivot axis 314. The pivot axis 314 is centered on the axis of the fastener 310 and the axis of the threaded opening 312. When the fastener 310 is tightly screwed into the threaded opening 312, the arm portions 302, 303 are secured together against pivoting movement. When the fastener is released, the arm portions 303, 302 may pivot relative to each other about the axis 314.

The end of the arm portion 302, which is adjacent to the arm portion 303, has a convex surface 350, which is curved about the axis 314. The arm portion 303 has a concave surface 351, which is also curved about the axis 314. The surfaces 350, 351 move concentrically relative to each other when the arm portions 303 and 302 pivot relatively about the axis 314.

The arm portion 303 has a set of teeth 320 which encircle the axis 314 and which project axially toward a set of teeth 321 on the arm portion 302. The teeth 321 project axially toward the teeth 320. The teeth 320 and the teeth 321 mesh with each other and provide a locking action so that the arm portions 302, 303 are positively locked against relative movement about axis 314 when the fastener 310 is tightly screwed into the opening 312. The teeth 320, 321 comprise a lock which blocks relative rotation of the arm portions 302, 303 about the axis 314. When the fastener 310 is loosened, the arm portions 302, 303 may be rotated relative to each other about the axis 314, and thus, the arm portions 302, 303 may pivot relative to each other to adjust the position of the support apparatus 110.

A cylindrical projection 325 is welded to the arm portion 303. Thus, the projection 325 and arm portion 303 are fixedly connected together. The projection 325 is centered on the axis 314 and contains a chamber 328.

As viewed in FIG. 20, the chamber 328 communicates with a fluid passage 329 in a male fluid connector 331. The male connector 331 attaches to a male connector 333 on the mechanical arm 301 by means of a flexible hose 392 so that the fluid passage 329 communicates with a fluid passage in the mechanical arm 301.

As viewed in FIG. 20, the chamber 328 is closed at its upper end by a cap 335. The cap 335 has an opening 336 centered on the axis 314. The opening 336 communicates with the chamber 328. A manually movable internal valve member 340 normally closes the opening and blocks the chamber 328 from communicating with the ambient air surrounding the support arm 300. The valve member 340 is connected to a stem 341, which is also centered on the axis 314. The stem 341 has a knob or button 343 on its end that may be manually depressed to move the stem 341 and valve member 340 downward into the chamber 328. When the stem 341 and valve member 340 are so moved, the chamber 328 is in communication with the ambient air surrounding the device due to the unblocking of the opening 336.

The mechanical arm 301 is a known device and is of the type generally disclosed in U.S. Pat. No. 4,863,133, which is incorporated by reference in its entirety herein. The mechanical arm 301 is sold by Leonard Medical, Inc. 1464 Holcomb Road, Huntington Valley, Pa., 19006. The mechanical arm 301 includes relatively movable parts, which permit movement and adjustment of the support apparatus 110 in a variety in planes, directions, and orientations. The mechanical arm 301 permits easy movement when a vacuum is not applied to the arm 301. When a vacuum is applied to the arm 301, relative movement of the parts of the arm 301 is resisted, and therefore adjustment of the support apparatus 110 is difficult.

When the button 343 is depressed, the chamber 328 loses its vacuum and the pressure in the chamber 328 increases toward ambient pressure. The passage 329 communicates this pressure increase to the mechanical arm 301, and thus the parts of the mechanical arm 301 are free to move and allow for adjustment of the position of the support apparatus 110 by the surgeon.

Accordingly, when the surgeon uses the support apparatus 110, the support arm 300 is snapped into the socket of the mechanical arm 301 where it is held by the detent 306. The surgeon may then depress the button 343 and relatively move parts of the mechanical arm 301, as well as the support apparatus 110 into the position where the surgeon desires the support apparatus 110 to be. This position may be where the opening 126 in the disk 124 is aligned with the proximal end 16 of the cannula 10 that has been positioned in the patient's body with the distal end 24 of the cannula 10 being located in an incision in the body of the patient. The viewing device 200 may be mounted on the support apparatus 110, and the surgeon may make adjustments prior to and during the surgical procedure as desired, as described above.

Figure 23:
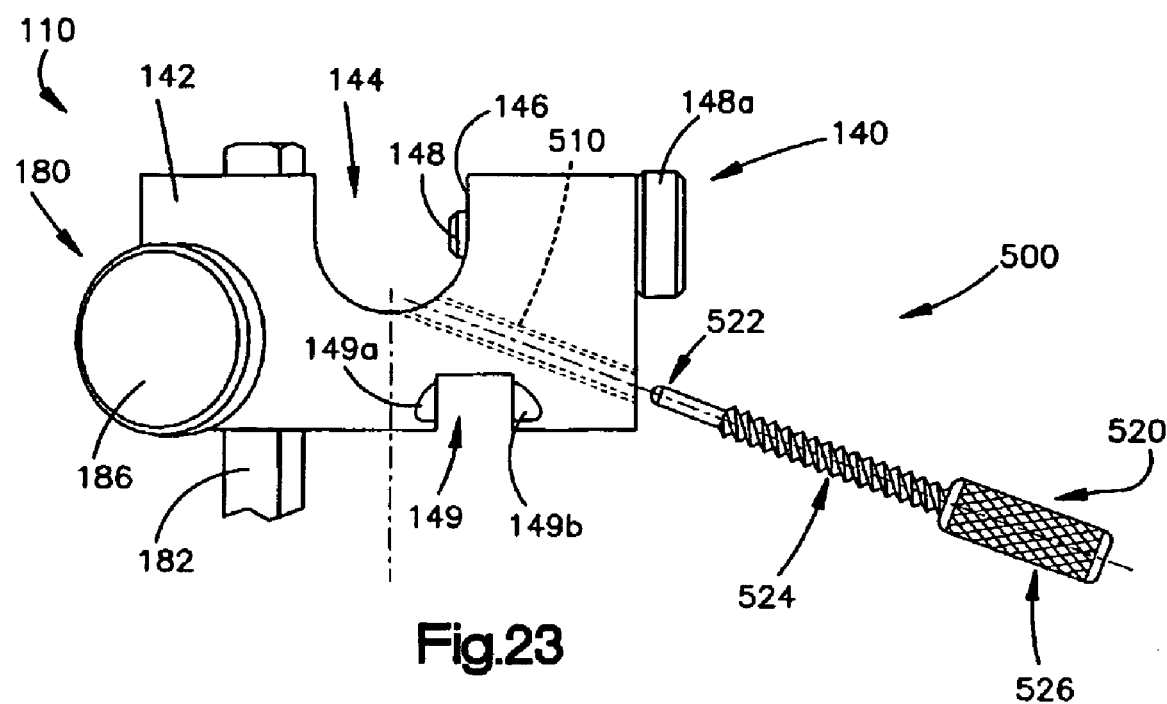
FIG. 23 is a schematic view of another feature of part of the support apparatus of FIG. 6.

As viewed in FIG. 23, the support apparatus 110 may include a second support with a fourth adjustment mechanism 500 for rotating the viewing device 200 about an axis 501 (FIG. 15) defined by the ball plungers 400 of the extension arms 151, 152 when set screw 148 is not clamping the viewing device 200 to the body 142. The axis 501 is offset from the axis 14 of the cannula 10 and perpendicular to the axis 14 of the cannula 10. Rotation of the viewing device 200 about axis 501 causes the endoscope 200 and the rod and lens assembly 203 to move perpendicular to the axis 14 of the cannula 10. This rotation will result in radial adjustment of the position of the rod and lens assembly 203 in a radial direction transverse to the axis 14.

The spring-loaded connections of the spherical detent members 420 of the ball plungers 400 and the hemispherical recesses of the endoscope 202 allow rotation about the axis 501 when the set screw 148 is released from clamping engagement of the viewing device 200.

The mechanism 500 includes a threaded bore 510 in the second support 140 and an adjustable member 520 for moving (vertically as viewed in the Figs.) a part of the viewing device 200 about the axis 501. The adjustable member 520 has a rounded first end portion 522, a threaded middle portion 524, and a knurled second end portion 526, or knob. The bore 510 extends at an angle as shown in FIG. 23 from a lower portion of the second support 140 up to the opening 144 in the clamp 146 of the second support 140.

The adjustable member 520 is rotated and threaded into the bore 510 and may be rotated until the first end portion 522 protrudes into the opening 144 of the second support 140. Accordingly, when the surgeon wishes to adjust the rod and lens assembly 203 (within the surgical sight) about the axis 501 and radially relative to the axis 14 of the cannula 10, the surgeon may loosen the connection of the set screw 148 with the viewing device 200 and rotate the adjustable member 520 by manually rotating knob 526 so that the first end portion 522 vertically extends farther or less into the opening 144. This adjustment will adjust the part of the viewing device 200 engaged by the clamp 146 along the axis 14, rotate the viewing device 200 about the axis 501, and cause the lens 203 at the surgical site to move transverse to the axis 14 of the cannula 10. This will expand the area of the surgical site that the surgeon may view. When the adjustment is complete, the surgeon may tighten the set screw 148 and re-secure the viewing device 200 to the second support 140 of the support apparatus 110.

Figure 24:
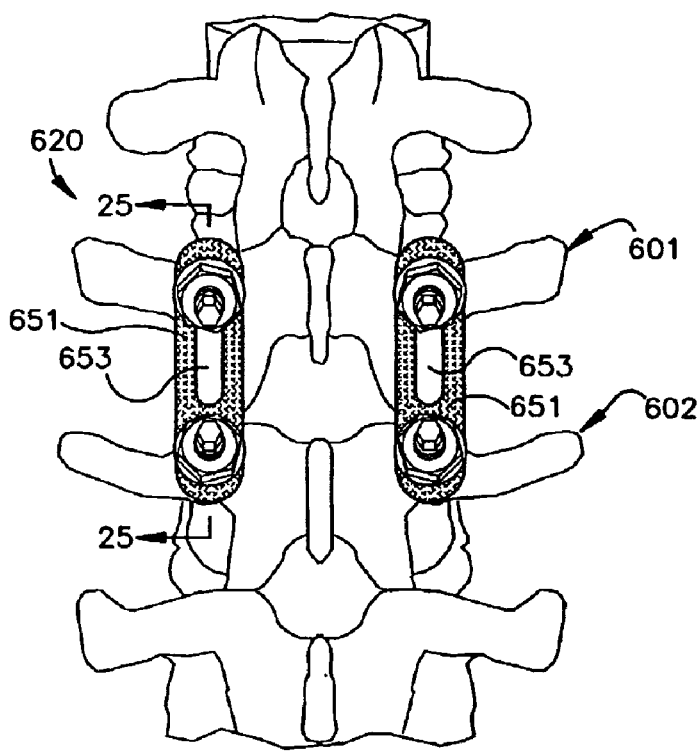
FIG. 24 is a schematic view of a fixation assembly attached to vertebrae of a patient.
Figure 25:
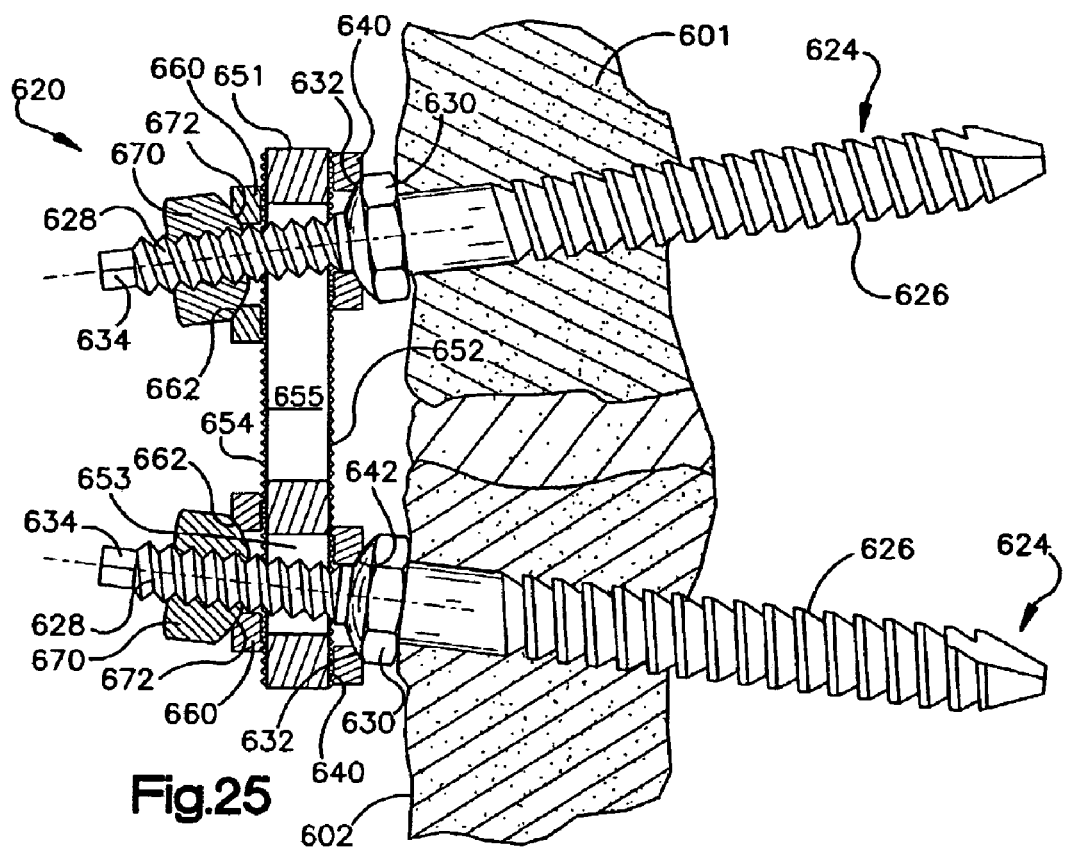
FIG. 25 is a schematic view taken along line 25-25 of FIG. 24.
Figure 26:
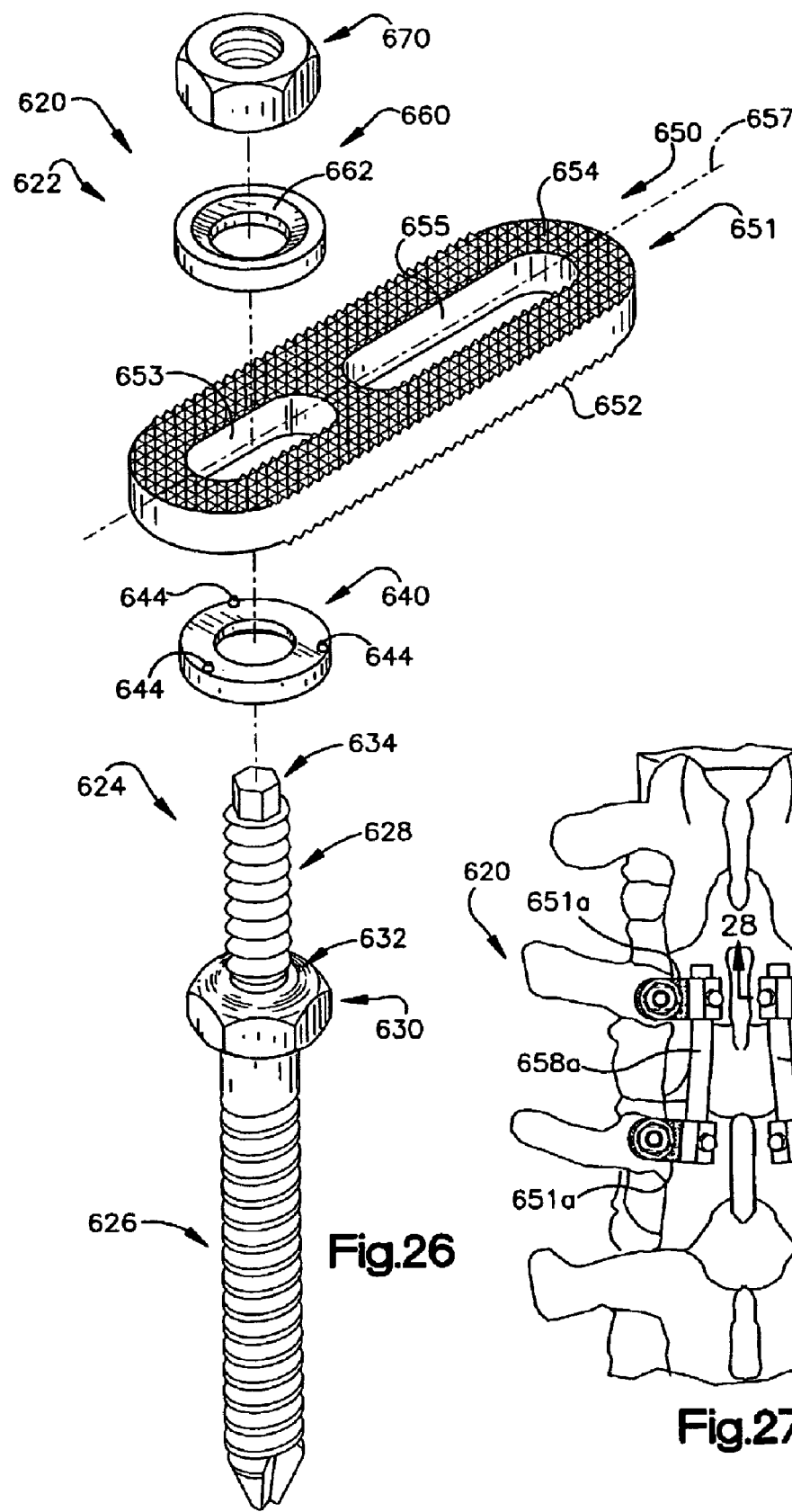
FIG. 26 is an exploded schematic view of part of the assembly of FIG. 24.
Figure 27:
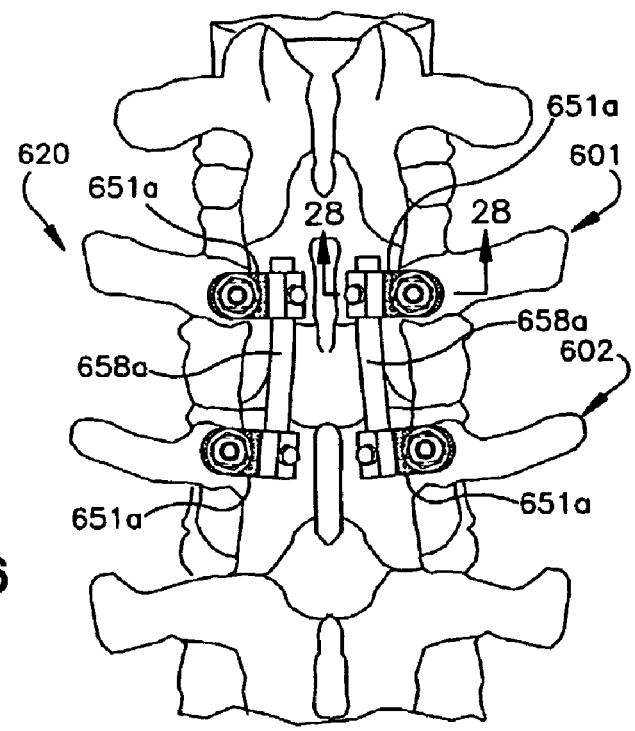
FIG. 27 is a schematic view of another fixation assembly attached to vertebrae of a patient.

The method of securing two vertebrae 601, 602 together according to one embodiment may include the insertion of a vertebral fixation assembly 620 through the cannula 10 and attachment of the vertebral fixation assembly 620 to two vertebrae (such as the L4 and L5 vertebrae), as viewed in FIGS. 24-29. The fixation assembly 620 may be of any suitable construction and is shown in FIG. 26 as including four identical attachment devices 622. Each attachment device 622 includes a threaded fastener 624 or pedicle screw, placed in a vertebra 601 or 602, as viewed in FIGS. 25 & 28. The fastener 624, has a first threaded portion 626 with a first threaded diameter that threads into the vertebrae 601, 602 by screwing the fastener 624 into the vertebrae. The fastener 624 further includes a second threaded portion 628 with a second threaded diameter that may be less than the first threaded diameter. The second threaded portion 628 extends away from the vertebrae 601, 602.

A first hexagonal engagement surface 630, intermediate the first and second threaded portions 626, 628, allows gripping of the fastener 624 when the fastener is screwed into the vertebrae 601, 602. A first convex engagement surface 632, adjacent the first hexagonal engagement surface 630 and the second threaded portion 628, projects away from the vertebrae 601, 602. A second hexagonal engagement surface 634 projects away from the second threaded portion 628 and allows further gripping of the fastener 624.

Each attachment device 622 further includes a first fixation washer 640 (FIGS. 26 & 29) that engages the first convex engagement surface 632. The first fixation washer 640 includes a first concave engagement surface 642 for abutting and slidingly engaging the first convex engagement surface 632 of the fastener 624.

The first fixation washer 640 further includes spikes 644, typically three, extending away from the vertebrae 601, 602. The spikes 644 of the first fixation washer 640 engage a lower knurled surface 652 of a vertebral fixation element 650 that in FIGS. 24-26 is a spine plate.

An upper knurled surface 654 of the fixation element 650 engages the spikes 664 of a second fixation washer 660 that is identical to the first fixation washer 640, but inverted, as viewed in FIGS. 26 & 29. A second convex engagement surface 672 of a threaded locking nut 670 abuts and slidingly engages the second concave engagement surface 662 of the second fixation washer 660 when the locking nut 670 is loosely threaded onto the second threaded portion 628 of the fastener 624.

The convex and concave engagement surfaces 632, 642, 662, 672 allow angular adjustment of the fixation elements 650, before the locking nut 670 is fully tightened, when the fasteners 624 are not threaded into the vertebrae 601, 602 exactly parallel to each other, as shown exaggerated in FIG. 25. These surfaces may typically allow for up to a 12-degree offset of the axes of the two fasteners 624.

One of two types of fixation elements 650 may typically be used to secure the vertebrae 601, 602 together. The first type may be a spinal plate 651 (FIG. 26) with two slots 653, 655 extending along the longitudinal axis 657 of the spinal plate. The second threaded portion 628 of one fastener 624, screwed into one vertebra 601, extends through one slot 653 and the second threaded portion 628 of another fastener 624, screwed into another vertebra 602, extends through the other larger slot 655. Two of the spinal plates 651, one on each side of the vertebrae 601, 602, are used to secure the two vertebrae together, as viewed in FIG. 24. The slots 653, 655 allow further transverse adjustment so that the same spinal plate 651 may be used for different size patients.

A second type of fixation element 650 may be two universal side blocks 651a (FIG. 29), each with one slot 653a extending along the longitudinal axis 657a of each side block and a securement opening 655a extending substantially perpendicularly to each slot 653a, as viewed in FIG. 29. The second threaded portion 628 of a fastener 624, screwed into one vertebra 601, extends through one slot 653a and the second threaded portion 628 of another fastener 624, screwed into another vertebrae 602, extends through a slot 653a in an identical side block 651a. The side blocks 651a further include lower and upper knurled surfaces 652a, 654a similar to the knurled surfaces 652, 654 of the spinal plate 651.

This second type of fixation element 650 further includes a rod 658a extending from the opening 655a in one side block 651a to the opening 655a in the other side block 651a. Set screws 659a secure the rod 658a in each opening 655a when the rod 658a is positioned properly to secure the vertebrae 601, 602 together, as viewed in FIG. 27.

Four of the side blocks 651a, one on each side of each vertebra 601, 602, and two rods 658a are used to secure the two vertebrae together. The slots 653a allow further transverse adjustment so that the same side block 651a may be used for different size patients. The rods 658a may also be cut to fit different sized patients.

The cannula 10, support apparatus 110, and vertebral fixation assembly 620 described above may be used to perform an operation which secures two vertebrae 601, 602 together, such as the posterolateral fusion and screw placement described above. This type of operation traditionally results in much blood loss because of the open access to the spine required for its performance. Utilizing the cannula 10 and support apparatus 110 for placement of the fixation assembly 620 at the surgical site and attachment of the fixation assembly 620 to the vertebrae 601, 602 in a manner to be described results in a much less invasive procedure and significantly less blood loss.

According to one embodiment, a method of fixing the vertebrae 601, 602 of a patient together at two surgical sites includes two main procedures. In the first procedure, a first cannula 10 is inserted into the body 130 of the patient adjacent one side of the spinal column. A second cannula 10 is inserted into the body 130 of the patient adjacent the other side of the spinal column. The second tubular portions 40 of both cannulae are expanded as described above thereby creating a substantially complete view of both sides of the two adjacent vertebrae 601, 602. In one embodiment, the two adjacent vertebrae 601, 602 are viewed by way of two endoscopes 200 and one or more monitors.

Alternatively, instead of using two cannulae and two endoscopes simultaneously so that both sides of adjacent vertebrae may be worked on by the surgeon at the same time, only one side of the adjacent vertebrae may be worked on and then the other side of the adjacent vertebrae may be worked on. In this case, only one endoscope, one endoscope support 110, and one monitor is required. Two cannulae would most probably be used, one for each side of the vertebrae.

In the second procedure, the vertebrae 601, 602 are accessed through the cannulae 10. Four insertion openings are drilled, one in each side of each vertebra 601, 602, utilizing suitable instruments extending through the cannulae 10. The fasteners 624 are inserted through each cannula 10 and are screwed one fastener 624 into each insertion opening, thereby securing each fastener 624 to a vertebra. The position of the vertebrae 601, 602 are checked to ensure that the vertebrae have maintained the proper position. If necessary, the vertebrae 601, 602 are repositioned. Eight fixation washers 640, 660, four locking nuts 670, and two fixation elements 650 are moved through the cannulae 10. Four fixation washers 640 and the fixation elements 650 are placed on the fasteners 624. Each fastener 624 is extended through one fixation washer and one slot in each fixation element 650. The additional fixation washers 660 are placed on the fasteners 624. The locking nuts 670 are threaded onto each fastener 624 thereby fixing the fixation elements 650 to the vertebrae 601, 602 and securing the vertebrae together in a natural and permanent position within the body. Also, bone graft may be moved through the cannulae 10 and placed in and around the fixation element 650 and fasteners 624 to permit a posterior fusion across the bony elements of the vertebrae 601, 602.

If necessary, the disc between the vertebrae 601, 602 may be removed through the cannula; the area between the vertebrae cleaned and the vertebrae prepared for receiving a fusion cage or cages and/or disc replacement material. This would be done before inserting the fasteners 624 or attaching the fixation elements 650. The method may also include inserting, through the cannulae 10, one or more appropriately sized fusion cages and positioning the fusion cage(s) appropriately relative to the vertebrae 601, 602; and inserting bone graft tissue through the cannulae 10 and positioning the tissue in and around the fusion cage(s).

The fusion cage may be of any known construction. One typical fusion cage is a hollow rectangular cage that is inserted into grooves that are formed in facing bone surfaces of the vertebrae. Another type of fusion cage is a hollow cylindrical threaded cage which screws into position between the vertebrae. Any suitable fusion cage may be used.

The cannulae 10 and the shrink wrap 102 are then removed from the body and the incisions are suitably closed. After a time, vertebrae 601, 602 and bone graft will grow together across the fusion cage(s) and in and around the fixation elements 650. The vertebrae 601, 602 will then no longer require the fixation assembly to maintain their position. The fixation elements 650 and fasteners 624 may then be removed. The removal procedure may utilize the same type of apparatus as was used in the first and second procedures (i.e., cannula, support apparatus, etc.).

The first and second cannulae 10 may be shifted slightly in the incisions in the body 130 to desired locations within the incisions at any time during the first and second procedures or the removal procedure. This is accomplished by changing the position of the support apparatus 110 by manipulating the arm 301.

The method described above may, and most probably does, involve removal of tissue from the surgical site through the cannula 10. Muscle, fat, and bone may be removed through the cannula 10 to provide a proper view of the vertebrae 601, 602 at the location to receive the fixation assembly 620. Different tools may be used in the process of removing tissue. These tools may include a burr and/or tissue cutting blades that are inserted through the cannula 10.

A preferred tissue cutting blade device 710 is shown in FIGS. 30-31. The device 710 has an axis 712 and includes inner and outer cutting tubes 740, 750. Each of the inner and outer tubes 740, 750 has openings 741, 751 into their interiors. Cutting teeth 745, 755 are located on opposite sides of each opening 741, 751.

The inner tube 740 rotates about the axis 712 relative to the outer tube 750 within the outer tube. The inner tube 740 rotates in opposite directions a predetermined amount equal to one or more revolutions about the axis 712, then rotates in the opposite direction the same predetermined amount. Thus, the inner tube 740 oscillates about the axis 712. As the inner tube 740 oscillates/rotates about the axis 712, the cutting teeth 745, 755 on the inner and outer tubes 740, 750 cut tissue. Alternatively, the inner tube 740 may rotate in one direction (clockwise or counterclockwise) within the outer tube.

During the cutting of tissue, a saline solution or the like may be forced through the annular space 770 between the inner tube 740 and the outer tube 750 to the surgical site. Suction may be applied in the opening 741 of the inner tube 740 to remove the cut tissue and the saline solution from the surgical site.

A tubular sheath 760 receives the inner and outer cutting tubes 740, 750. The sheath 760 extends along the length of the cutting tubes 740, 750 and adjacent a distal end of the cutting tubes where the cutting teeth 745, 755 are located. The sheath 760 is a stainless steel tube that is electrically insulated along its length from the patient's body and from the outer tube 750. An electrical insulator 763, such as a suitable polymer coating, is provided over the outside and inside surfaces of the sheath 760. However, a selected area 762 of the outside surface of the sheath 760 adjacent the distal end of the cutting tubes 740, 750 is not coated with the insulator 763. A portion 765 of the distal end of the sheath 760 is cut away so that the cutting teeth 745, 755 on the cutting tubes 740, 750 are not blocked by the sheath 760 from cutting tissue.

An electric current from a current source 766 is applied to the sheath 760. The electric current flows through the sheath 760 and to the selected uncoated area 762 of the sheath. The current then flows through tissue and blood into the distal end of the outer cutting tube 750 and back to the current source through the outer cutting tube to form a completed circuit.

The current flow through the electrically energized sheath 760 and outer cutting tube 750 serves to electrocoagulate blood in the cutting area at the surgical site. Electrocoagulation of blood is known and any other suitable electrocoagulation device may alternatively be used.

It is contemplated that viewing of the surgical site may be performed without using an endoscope. A microscope or glasses that magnify the site may be used. In fact, any suitable viewing device may be used. Also, the procedure discussed above mentions drilling the vertebrae. Any suitable alternative to drilling may be used such as using an awl or other instrument to form an opening to receive a fastener.

Figure 32:
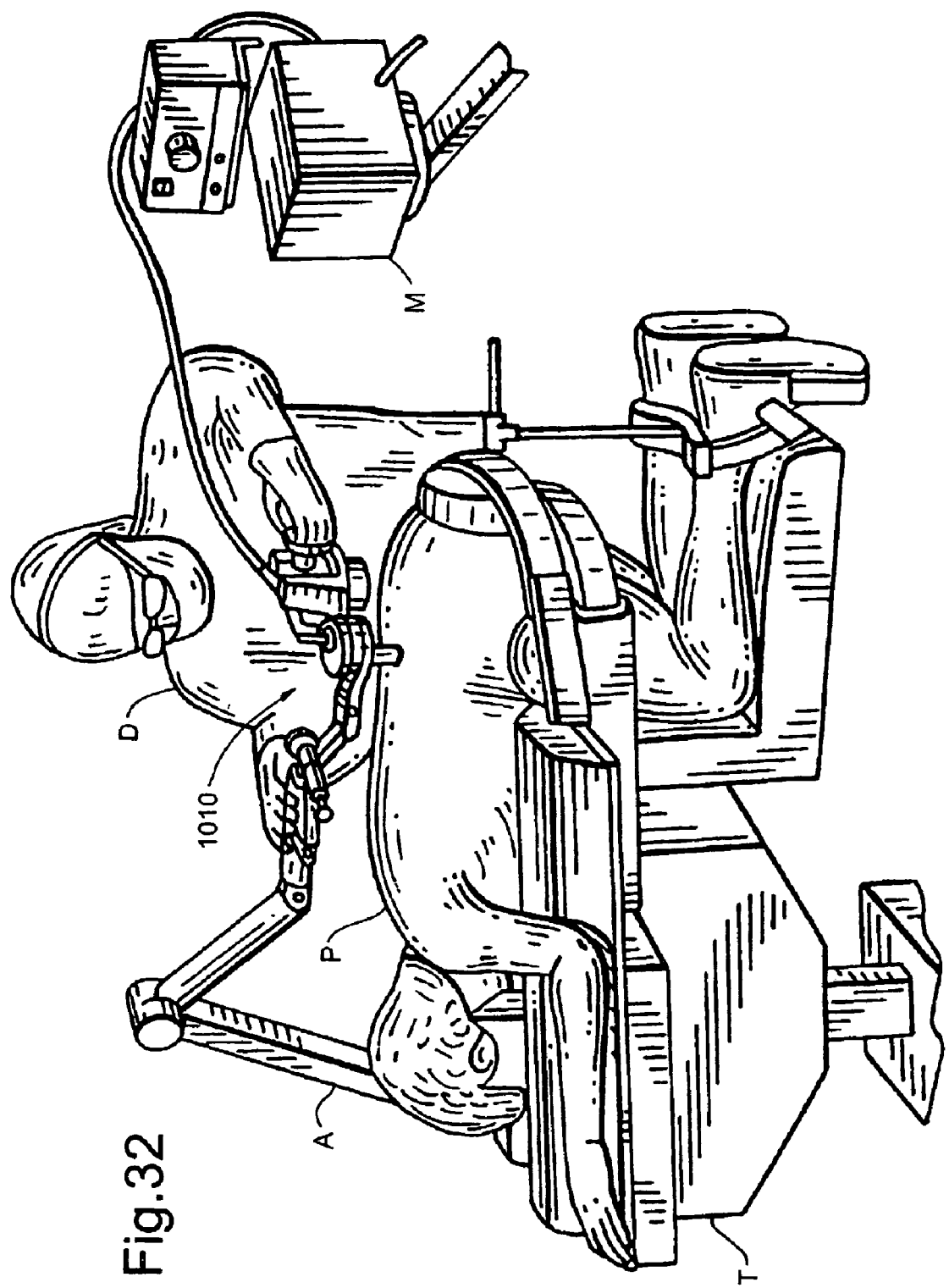
FIG. 32 is a perspective view of a surgical system and procedure according to another embodiment.
Figure 33:
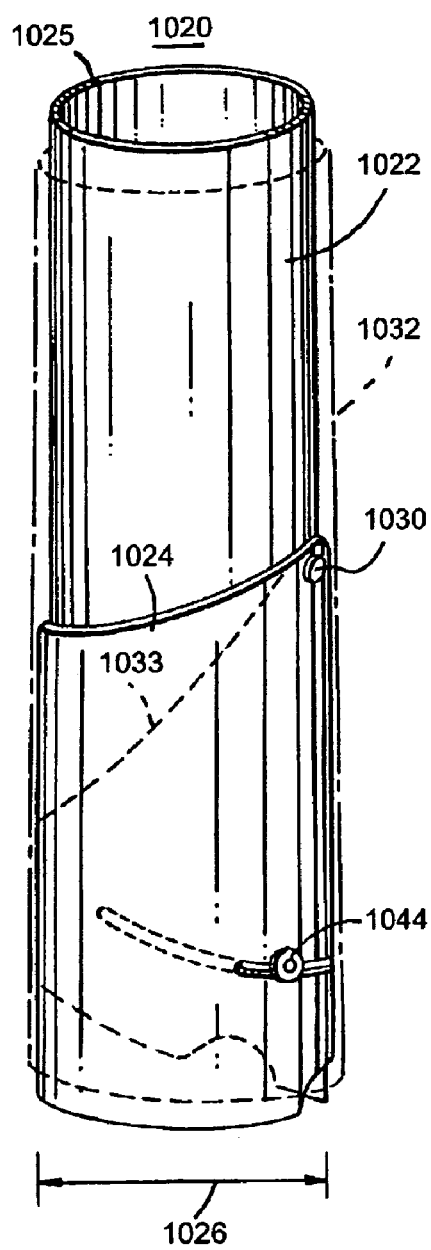
FIG. 33 is a perspective view of a cannula or expandable conduit in a reduced profile configuration according to another embodiment.

An exemplary arrangement for performing a procedure in accordance with the invention is illustrated in FIG. 32. The patient P is typically placed in the prone position on operating table T, taking care that the abdomen is not compressed and physiological lordosis is preserved, as is known in the art. The physician D is able to access the surgical site and perform the surgical procedure with the components of a surgical system 1010, which will be described in greater detail herein. The system 1010 may be supported, in part, by a mechanical support arm A, such as the type generally disclosed in U.S. Pat. No. 4,863,133, which is incorporated by reference in its entirety herein. The mechanical arm of this type is manufactured by Leonard Medical, Inc., 1464 Holcomb Road, Huntington Valley, Pa., 19006. The physician D is able to view the procedure by reference to a monitor M, which displays the images captured by an endoscope and camera which will be described in greater detail herein. Alternatively, the physician D may view the surgical site though an eyepiece of the endoscope, or she may directly view the surgical site with loupes, microscope, or with the unaided eye.

The procedure described below is a two level posterolateral fixation of the spine involving the L4, L5 and S1 vertebrae. (In the drawings, the vertebrae will generally be denoted by reference letter V.) The usefulness of the inventive procedure is neither restricted to the posterolateral approach nor to the L4, L5 and S1 vertebrae, but it may be used in other anatomical approaches and other vertebrae within the cervical, thoracic and lumbar spine. The inventive procedure may be directed toward surgery involving one or more vertebral levels. It is also useful for anterior and lateral procedures. Moreover, it is believed that the invention is also particularly useful where any body structures must be accessed beneath the skin and muscle tissue of the patient, and where it desirable to provide sufficient space and visibility in order to manipulate surgical instrumentation and treat the underlying body structures. For example, certain features or instrumentation described herein are particularly useful for a minimally invasive, e.g., arthroscopic procedures, in which the expandable distal portion of the expandable conduit prevents the instrument from dislodging or popping out of the operative site.

The system 1010 includes another access device, such as an expandable cannula or conduit which provides an internal passage for surgical instrumentation to be inserted through the skin and muscle tissue of the patient P to the surgical site. The expandable conduit has a wall portion defining reduced profile configuration for initial percutaneous insertion into the patient. This wall portion may have a generally tubular configuration that may be passed over a dilator that has been inserted into the patient to atraumatically enlarge an opening sufficiently large to receive the expandable conduit therein.

The wall portion of the expandable conduit is subsequently expanded to an enlarged configuration, by moving against the surrounding muscle tissue to at least partially define an enlarged surgical space in which the surgical procedures will be performed. In a sense, it acts as its own dilator. Typically, but not by way of limitation, the distal portion expands to a greater extent than the proximal portion, since the surgical procedures are to be performed at the surgical site adjacent the distal portion thereof.

While in the reduced profile configuration, the expandable conduit defines a first unexpanded configuration. Thereafter, the expandable conduit enlarges the surgical space defined thereby by engaging the tissue surrounding the conduit and displacing the tissue radially outwardly as the conduit expands. The expandable conduit may be sufficiently rigid to displace such tissue during the expansion thereof. The expandable conduit may be resiliently biased to expand from the reduced profile configuration to the enlarged configuration. In addition, the conduit may also be manually expanded with surgical instrumentation inserted therein, as will be described below. The surgical site is at least partially defined by the expanded conduit itself. During expansion, the conduit moves from the first overlapping configuration to a second overlapping configuration.

In addition to enlargement, the distal end portion of the expandable conduit may be configured for relative movement with respect to the proximal end portion in order to allow the physician to precisely position the distal portion at the desired location. This relative movement also provides the advantage that the proximal portion of the expandable conduit nearest the physician D may remain substantially stable during such distal movement. In an exemplary embodiment, the distal portion is a separate component which is pivotably or movably attached relative to the proximal portion. Alternatively, the distal portion is flexible or resilient in order to permit such relative movement.

Another embodiment of the cannula or expandable conduit for use in a method is illustrated in FIGS. 33-37 and is designated by reference number 1020. The expandable conduit 1020 includes a proximal wall portion 1022, which has a tubular configuration, and a distal wall portion, which is an expandable skirt portion 1024. The skirt portion 1024 is expandable from a reduced profile configuration having an initial dimension 1026 and corresponding cross-sectional area (illustrated in FIG. 33), to an enlarged configuration having a dimension 1028 and corresponding cross-sectional area (illustrated in FIG. 35). The skirt portion 1024 may be attached to the proximal cylindrical tube portion 1022 with a rivet 1030, pin, or similar connecting device to permit movement of the skirt portion 1024 relative to the proximal cylindrical tube portion 1022.

Figure 34:
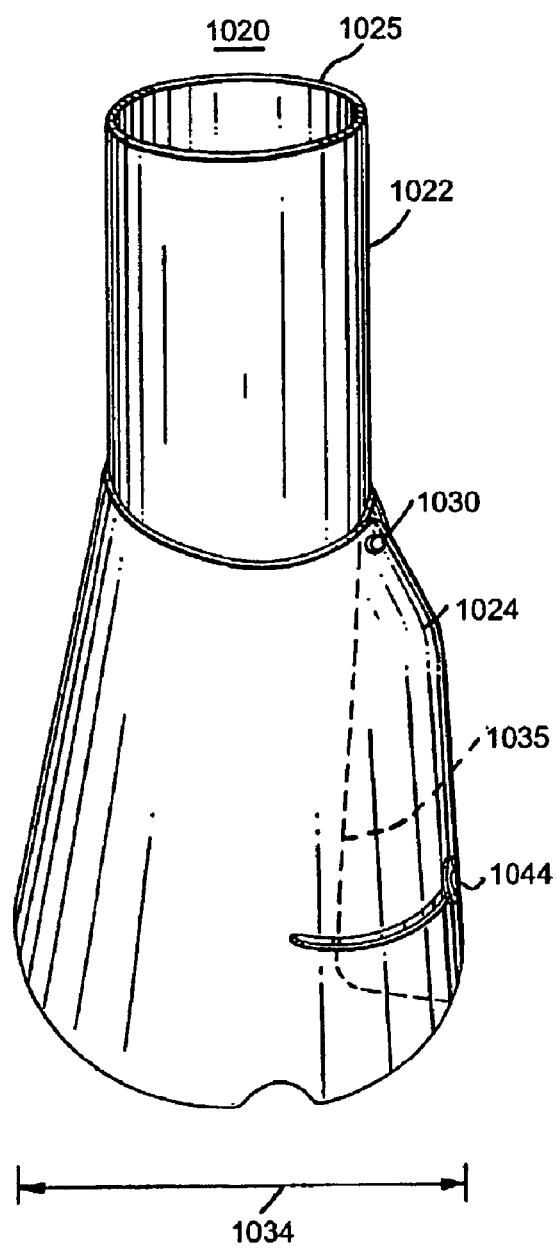
FIG. 34 is a perspective view of the expandable conduit of FIG. 33 in a first enlarged configuration.
Figure 35:
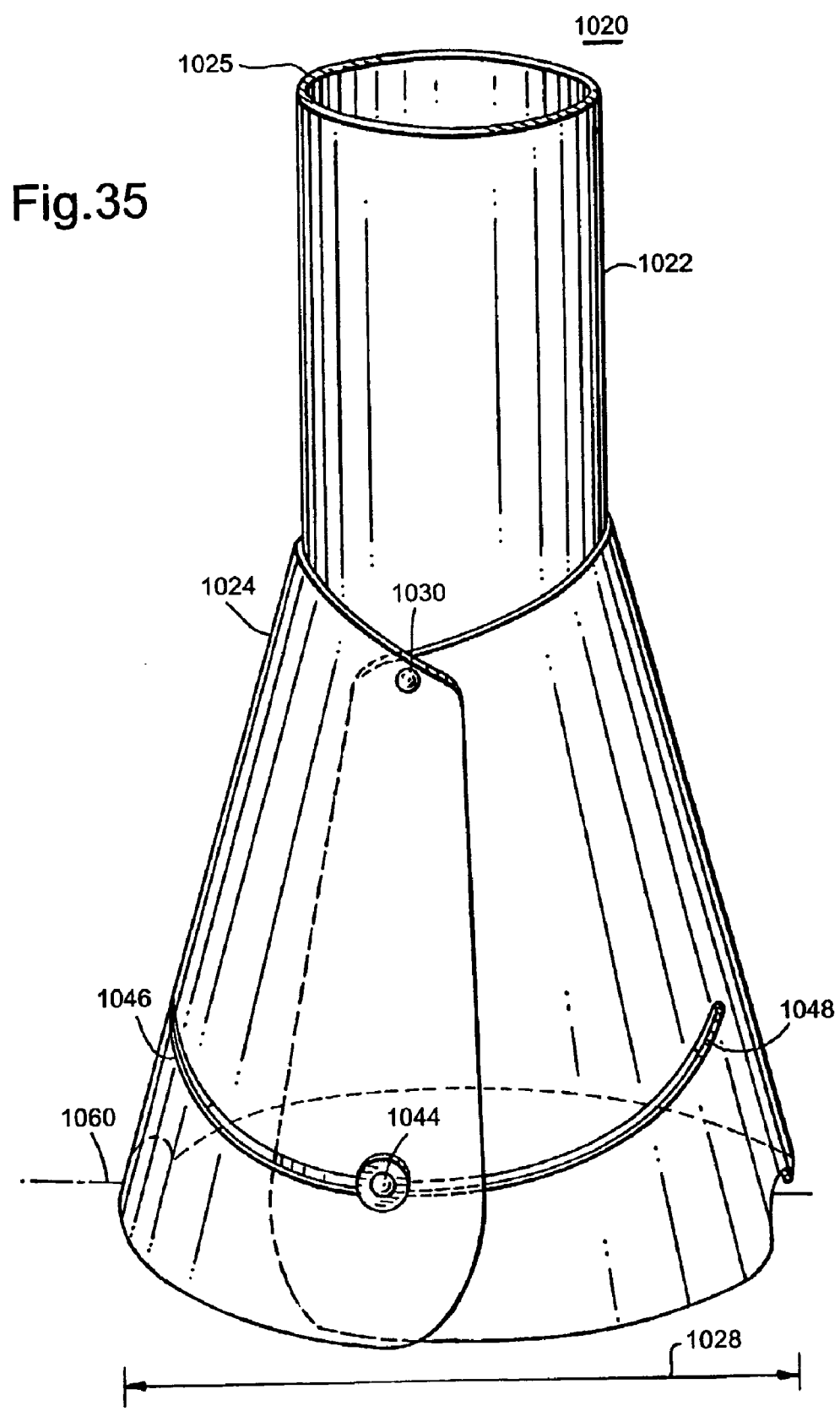
FIG. 35 is a perspective view of the expandable conduit of FIG. 33 in a second enlarged configuration.
Figure 37:
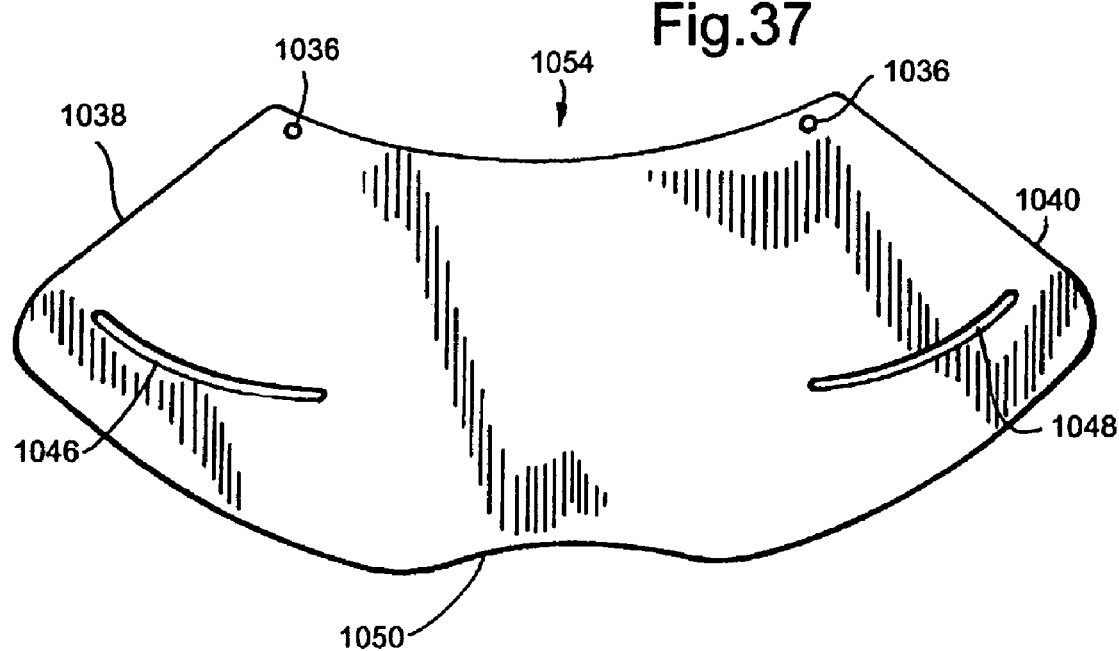
FIG. 37 is a view of a cannula skirt according to another embodiment.

The skirt portion 1024 is manufactured from a resilient material, such as stainless steel. The skirt 1024 is manufactured so that it normally assumes an expanded configuration illustrated in FIG. 35. As illustrated in FIG. 34, the skirt portion 1024 may assume an intermediate dimension 1034 and corresponding cross-sectional area, which is greater than dimension 1026 of the reduced profile configuration of FIG. 33, and smaller than dimension 1028 of FIG. 35. Skirt portion 1024 may assume the configuration of FIG. 34 when deployed in the patient in response to the force of the tissue acting on the skirt portion. The actual dimension 1034 will depend upon several factors, including the rigidity of the skirt portion 1024, the surrounding tissue, and whether such surrounding tissue has relaxed or tightened during the course of the procedure. An outer plastic sleeve 1032 (illustrated in dashed line in FIG. 33) may be provided which surrounds the expandable conduit 1020 and maintains the skirt 1024 in the reduced profile configuration. The plastic sleeve 1032 may have a braided polyester suture embedded within it (not shown), aligned substantially along the longitudinal axis thereof; such that when the suture is withdrawn, the sleeve 1032 is torn, which allows the expandable conduit 1020 to resiliently expand from the reduced profile configuration of FIG. 33 to the expanded configurations of FIGS. 34-35. While in the reduced profile configuration of FIG. 33, the skirt portion 1024 defines a first overlapping configuration 1033, as illustrated by the dashed line. As the skirt portion 1024 resiliently expands, the skirt portion assumes the second configuration 1035, as illustrated in FIGS. 34-35.

The skirt portion 1024 is sufficiently rigid that it is capable of displacing the tissue surrounding the skirt portion as it expands. Depending upon the resistance exerted by surrounding tissue, the skirt portion 1024 is sufficiently rigid to provide some resistance against the tissue to remain in the configurations of FIGS. 34-35. Moreover, the expanded configuration of the skirt portion 1024 is at least partially supported by the body tissue of the patient. The rigidity of the skirt portion 1024 and the greater expansion at the distal portion creates a stable configuration that is at least temporarily stationary in the patient, which frees the physician from the need to actively support the conduit 1020 until the endoscope mount platform 1300 and support arm 1400 are subsequently added (see FIGS. 52-53).

Figure 36:
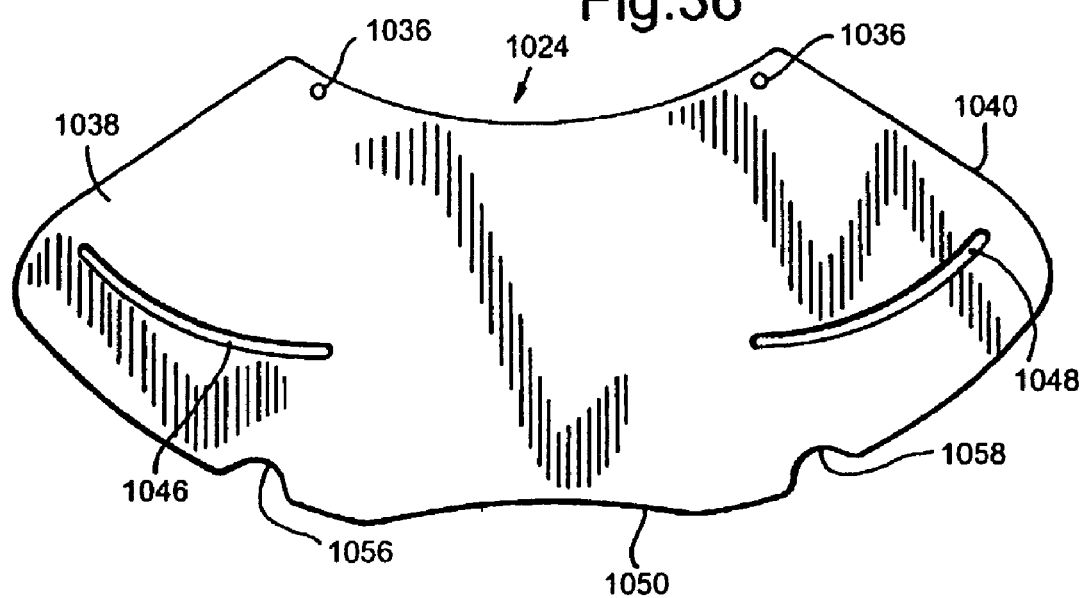
FIG. 36 is a view of a cannula skirt according to another embodiment.

The skirt portion 1024 of expandable conduit 1020 is illustrated in an initial flattened configuration in FIG. 36. The skirt portion 1024 may be manufactured from a sheet of stainless steel having a thickness of about 0.007 inches for skirt portions having a fully expanded dimension 1028 of about 65 mm in its unrestricted circular shape. The skirt portion 1024 may also take on an oval shape having a longer dimension of about 85 mm. An increased thickness, e.g., about 0.010 inches, may be used in connection with skirt portions having a larger diameter, such as about 65 mm. Other materials, such as Nitinol or plastics having similar properties, may also be useful.

As discussed above, the skirt portion 1024 is attached to the proximal cylindrical portion 1022 with a pivotable connection, such as rivet 1030. A pair of rivet holes 1036 are provided in the skirt portion 1024 to receive the rivet 1030. The two free ends 1038 and 1040 of the skirt portion 1024 are secured by a slidable connection, such as second rivet 1044 (not shown in FIG. 36, illustrated in FIGS. 33-35). A pair of complementary slots 1046 and 1048 are defined in the skirt portion 1024 adjacent the end portions 1038 and 1040. The rivet 1044 is permitted to move freely within the slots 1046 and 1048. This slot and rivet configuration allows the skirt portion 1024 to move between the reduced profile configuration of FIG. 33 and the expanded configuration of FIGS. 34-35. The use of a pair of slots 1046 and 1048 reduces the risk of the "button-holing" of the rivet, i.e., a situation in which the opening of the slot becomes distorted and enlarged such that the rivet may slide out of the slot, and cause failure of the device. However, the likelihood of such occurrence is reduced in skirt portion 1024 since each of the slots 1046 and 1048 in the double slot configuration has a relatively shorter length than a single slot configuration, which thereby limits the ability of the respective slots 1046 and 1048 to be distorted to the extent in which a rivet may slide out of position. In addition, the configuration of rivet 1044 and slots 1046 and 1048 permits a smooth operation of enlarging and reducing the skirt portion 1024, and allows the skirt 1024 to expand to span as many as three vertebrae, e.g., L4, L5, and S1, to perform a multi-level fixation.

An additional feature of the skirt 1024 is the provision of a shallow concave profile 1050 defined along the distal edge of the skirt 1024, which allows for improved placement of the skirt 1024 with respect to the body structures and the surgical instruments defined herein. Small scalloped or notched portions 1056 and 1058, are provided, as illustrated in FIG. 36. When the skirt 1024 is assembled, the cut out portions 1056 and 1058 are oriented in the cephalad-caudal direction (indicated by arrow 1060) in FIG. 35 and permit instrumentation, such as an elongated member or fixation element 4650 used in a fixation procedure to secure vertebrae (described in detail below), to extend beyond the area enclosed by the skirt portion 1024 without moving or raising the skirt portion 1024 from its location to allow the elongated member 4650 to pass under the skirt portion 1024. (In another embodiment of the cannula or expandable conduit 1054 illustrated in FIG. 37, cut out portions 1056 and 1058 are eliminated from the contour where the physician deems such cut out portions 1056 and 1058 to be unnecessary in view of the spacing of the fasteners 4600 or the length of the elongated member 4650.)

As illustrated in FIG. 35, the skirt 1024 may be expanded to a substantially conical configuration having a substantially circular or elliptical profile. Alternatively, features may be provided on the skirt which facilitate the bending of the skirt at several locations to provide a pre-formed enlarged configuration. For example, in another embodiment of the cannula or expandable conduit 1070, illustrated in FIGS. 38-40, skirt portion 1074 may have four sections 1076a, 1076b, 1076c, 1076d having a reduced thickness. For a skirt portion 1074 having a thickness 1078 of about 0.007 inches thick, reduced thickness sections 1076a, 1076b, 1076c, 1076d may have a thickness 1080 of about 0.002-0.004 inches (FIG. 39). The width of the reduced thickness sections 1076a, 1076b, 1076c, 1076d may be about 1-5 mm. The thickness 1078 of the skirt portion 1074 may be reduced by milling or grinding, as is known in the art. Thus when the skirt 1074 is opened, it moves toward a substantially rectangular configuration, subject to the resisting forces of the body tissue (FIG. 40). Alternatively, another embodiment of the skirt (not shown) may be provided with two reduced thickness sections (rather than the four reduced thickness sections of skirt 1074) which would produce a substantially "football"-shaped access area.

In another embodiment of the cannula or expandable conduit 1080, the skirt portion 1084 is provided with a plurality of perforations 1086, in order to increase flexibility at the desired locations (FIGS. 41-43). The size and number of perforations 1086 may vary depending upon the desired flexibility and durability. Alternatively, the skirt may be scored or otherwise provided with a groove or rib in order to facilitate the bending of the skirt at the desired location.

According to still further embodiments, the cannula or expandable conduit may be provided with one slot. As illustrated in FIG. 44, skirt portion 1094 is provided with slot 1096 and aperture 1098. A rivet (not shown) is stationary with respect to aperture 1098 and slides within slot 1096. Similarly, skirt 1104 is provided with an aperture 1108 which receives a rivet (not shown) which slides within elongated slot 1106 (FIG. 45).

An early stage in the process is to determine the access point in the skin of the patient to insert the access conduit. In the exemplary embodiment, the access point corresponds to the posterior-lateral aspects of the spine. Manual palpation and Anterior-Posterior (AP) fluoroscopy may be used to determine the optimal incision locations. For the exemplary procedure, placement of the cannula or expandable conduit 1020 is preferably midway (in the cephalad-caudal direction) between the L4 through S1 vertebrae, centrally about 4-7 cm from the midline.

An incision is made at the above-determined location. A guide wire (not shown) is introduced under fluoroscopic guidance through the skin, fascia, and muscle to the approximate surgical site. A series of dilators is used to sequentially expand the incision to the desired width, about 23 mm for the exemplary procedure, without damaging the structure of surrounding tissue and muscles. A first dilator is placed over the guide wire, which expands the opening. The guide wire is then subsequently removed. A second dilator that is slightly larger than the first dilator is placed over the first dilator, which expands the opening further. Once the second dilator is in place, the first dilator is subsequently removed. This process of (1) introducing a next-larger-sized dilator coaxially over the previous dilator and (2) subsequently removing the previous dilator when the next-larger-sized dilator is in place continues until an opening of the desired size is created in the skin, muscle, and subcutaneous tissue. In the exemplary method, this dimension is about 23 mm. (Other dimensions of the opening, e.g., about 20 mm, 27 mm, 30 mm, etc., are also useful with this apparatus in connection with spinal surgery, and still other dimensions are contemplated.)

Figure 46:
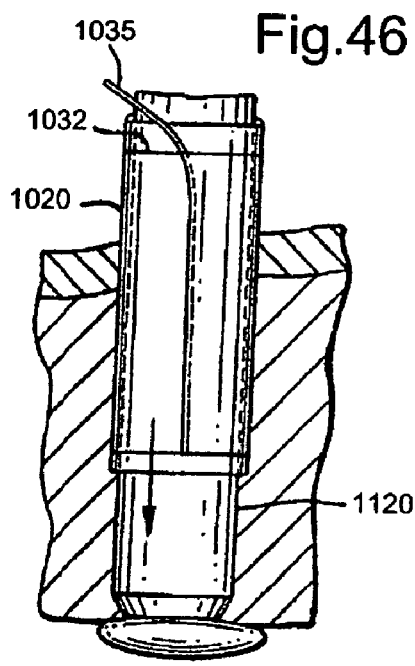
FIG. 46 is a sectional view illustrating an early stage of a procedure according to another embodiment.

As illustrated in FIG. 46, following placement of the largest dilator 1120, the expandable conduit 1020, in its reduced profile configuration, is introduced and positioned in a surrounding relationship over the dilator 1120. Dilator 1120 is subsequently removed from the patient, and the expandable conduit 1020 is allowed to remain in position.

Once the expandable conduit 1020 is positioned in the patient, it may be enlarged to provide a passage for the insertion of various surgical instrumentation and an enlarged space for performing the procedures described herein. As described above, the expandable conduit may accommodate the enlargement in several ways. In one embodiment, a distal portion of the cannula may be enlarged, and a proximal portion may maintain a constant diameter. The relative lengths of the proximal portion 1022 and the skirt portion 1024 may be adjusted to vary the overall expansion of the conduit 1020. Alternatively, such expansion may extend along the entire length of the expandable conduit. In the exemplary procedure, the expandable conduit 1020 may be expanded by removing suture 1035 and tearing sleeve 1032 surrounding the expandable conduit 1020, and subsequently allowing the skirt portion 1024 to resiliently expand towards its fully expanded configuration as (illustrated in FIG. 35) to create an enlarged surgical space from the L4 to the S1 vertebrae. The resisting force exerted on the skirt portion may result in the skirt portion 1024 assuming the intermediate configuration illustrated in FIG. 34. Under many circumstances, the space created by the skirt portion 1024 in the intermediate configuration is a sufficiently large working space to perform the procedure described herein. Once the skirt portion 1024 has expanded, the rigidity and resilient characteristics of the skirt portion 1024 allow the conduit 1020 to resist closing to the reduced profile configuration of FIG. 33 and to at least temporarily resist being expelled from the incision. These characteristics create a stable configuration for the conduit 1020 to remain in position in the body, supported by the surrounding tissue. It is understood that additional support may be needed, especially when an endoscope 1500 is added.

According to the exemplary embodiment, the expandable conduit 1020 may be further enlarged at its distal end portion using an expander apparatus to create a surgical access space. An expander apparatus useful for enlarging the expandable conduit has a reduced profile configuration and an enlarged configuration. The expander apparatus is inserted into the expandable conduit in the reduced profile configuration, and subsequently expanded to the enlarged configuration. The expansion of the expander apparatus also causes the expandable conduit to be expanded to the enlarged configuration. In some embodiments, the expander apparatus may increase the diameter of the expandable conduit along substantially its entire length in a conical configuration. In other embodiments, the expander apparatus expands only a distal portion of the expandable conduit, allowing a proximal portion to maintain a constant diameter.

In addition to expanding the expandable conduit, the expander apparatus may also be used to position the distal portion of the expandable conduit at the desired location for the surgical procedure. The expander engages the interior wall of the expandable conduit, and moves the cannula to the proper location. For the embodiments in which the distal portion of the expandable conduit is relatively movable with respect to the proximal portion, the expander apparatus is useful to position the distal portion without substantially disturbing the proximal portion.

Figure 48:
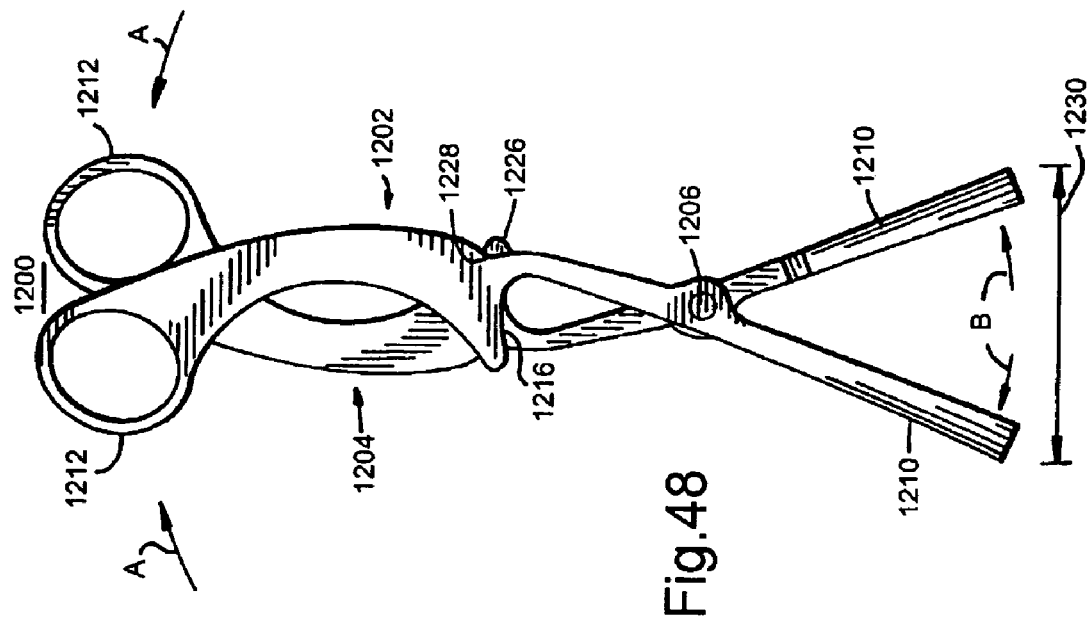
FIG. 48 is a side view of the apparatus of FIG. 47 in an expanded configuration.
Figure 47:
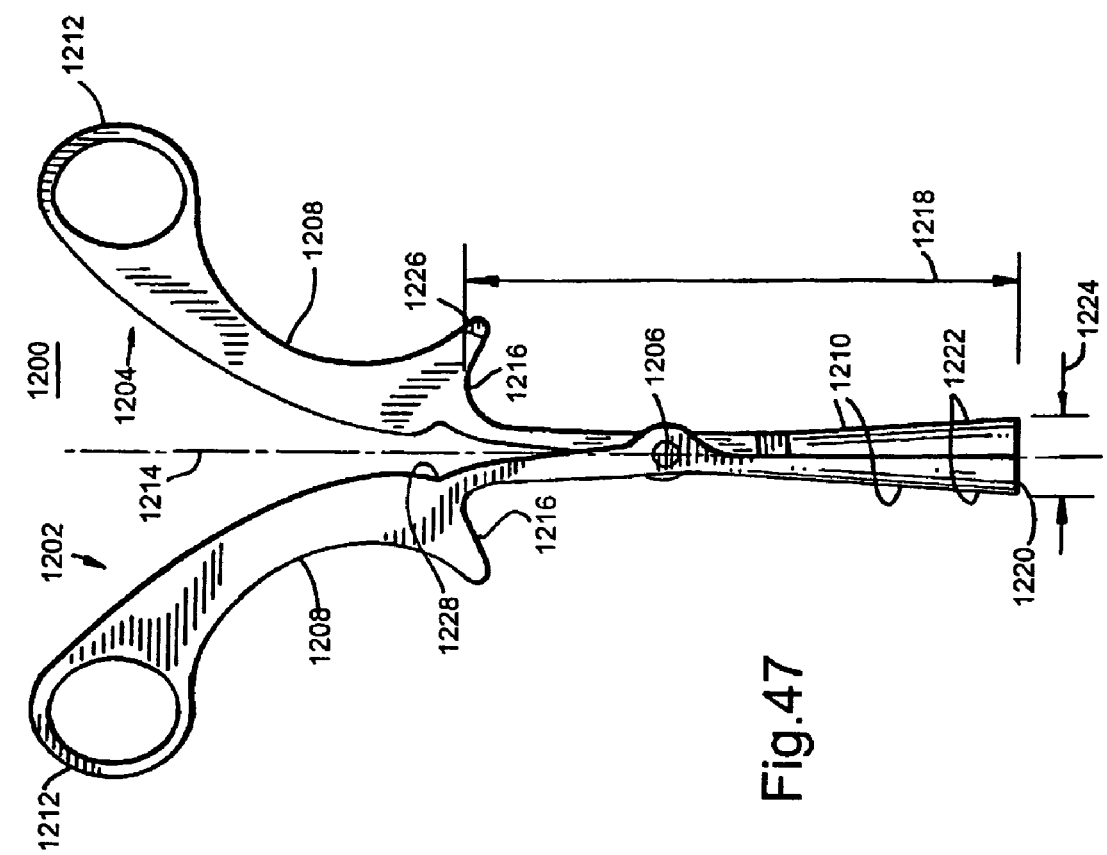
FIG. 47 is a side view of another apparatus in a reduced profile configuration according to another embodiment.

In the exemplary embodiment, an expander apparatus may be used to further expand the skirt portion 1024 towards the fully expanded configuration (illustrated in FIG. 35). The expander apparatus is inserted into the expandable conduit, and typically has two or more members which are movable to engage the interior wall of the skirt portion 1024 and apply a force sufficient to further expand the skirt portion. An exemplary expander apparatus, expander apparatus 1200, is illustrated in FIGS. 47 and 48, and is constructed of two components 1202 and 1204 defining a tongs-like configuration, and which are pivotable about a pin 1206. The components 1202 and 1204 are typically constructed of steel having a thickness of about 9.7 mm. Each of the components 1202 and 1204 has a proximal handle portion 1208 and a distal expander portion 1210. Each proximal handle portion 1208 has a finger grip 1212 that may extend transversely from the longitudinal axis 1214 of the apparatus 1200. The proximal handle portion 1208 may further include a stop element, such as flange 1216, that extends transversely from the longitudinal axis 1214, and which is dimensioned to provide a visual and tactile indication of the proper depth for inserting the expander apparatus 1200 by engaging the proximal portion 1025 of the expandable conduit 1020 when the apparatus 1200 is inserted a predetermined depth. In the exemplary embodiment, the dimension 1218 from the flange 1216 to the distal tip 1220 is about 106 mm. The dimension 1218 is determined by the typical depth of the body structures beneath the skin surface at which the surgical procedure is being performed. The distal portions 1210 are each provided with a frusto-conical outer surface 1222 for engaging the inside wall of the skirt portion 1024. As illustrated in FIG. 47, the unexpanded distal width 1224 of the apparatus 1200 at the distal tip 1220 is about 18.5 mm.

In use, the finger grips 1212 are approximated towards one another (arrow A), which causes the distal portions 1210 to move to the enlarged configuration (arrows B), illustrated in FIG. 48. The components 1202 and 1204 are also provided with a cooperating tab 1226 and shoulder portion 1228 which are configured for mutual engagement when the distal portions 1210 are in the expanded configuration. In the exemplary embodiment, the expanded distal width 1230 of the distal portions 1210 is about 65 mm to about as large as 83 mm. The tab 1226 and shoulder configuration 1228 limits the expansion of the apparatus 1200 in order to prevent expanding the skirt portion 1024 of the expandable conduit 1020 beyond its designed dimension, and to minimize trauma to the underlying tissue. Further details of the expander apparatus are described in U.S. patent application Ser. No. 09/906,463 filed Jul. 16, 2001, which is incorporated by reference in its entirety herein.

When the expandable conduit 1020 is inserted into the patient and sleeve 1032 is removed, the skirt portion 1024 expands to a point where the outward resilient expansion of the skirt portion is balanced by the force of the surrounding tissue. The surgical space defined by the conduit may be sufficient to perform the surgical procedures. However, if it is desired to expand the expandable conduit 1020 further, the expander apparatus 1200 may be inserted into the expandable conduit 1020 in the reduced profile configuration until the shoulder portions 1216 are in approximation with the proximal lip 1025 of the cylindrical portion 1024 of the expandable conduit 1020 (FIG. 49).

Figure 49:
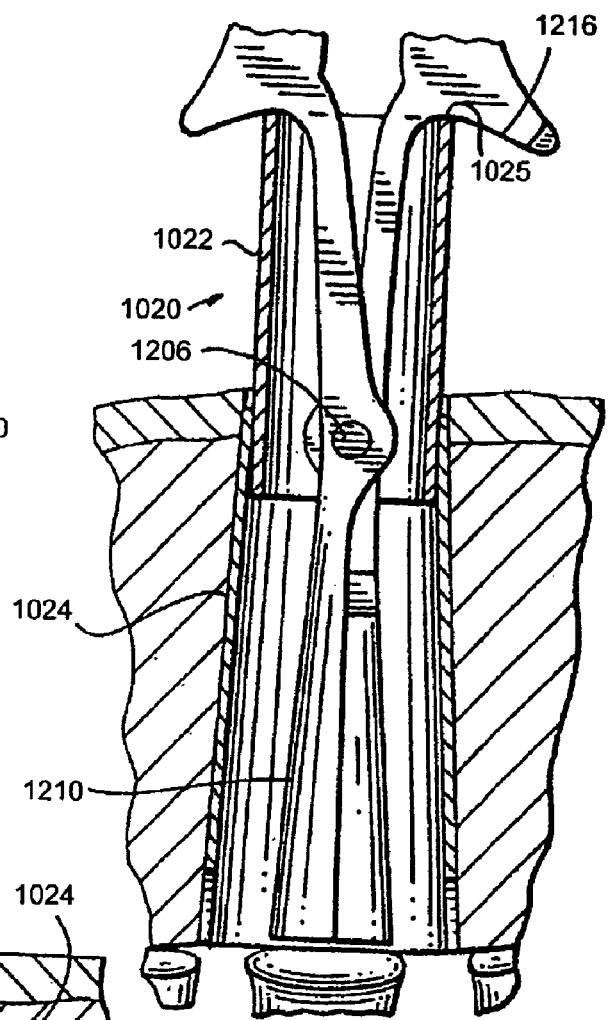
FIG. 49 is a sectional view of the apparatus of FIGS. 47-48 inserted into the expandable conduit of FIG. 33.
Figure 50:
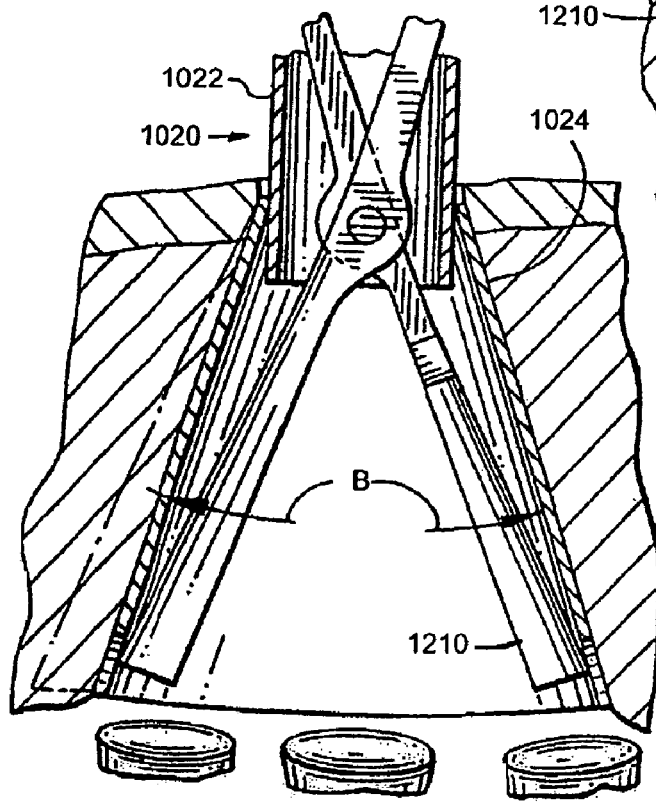
FIG. 50 is a sectional view of the apparatus of FIGS. 47-48 inserted into the expandable conduit of FIG. 33.

As illustrated in FIG. 49, the expander apparatus 1200 is inserted in the access conduit 1020 in the reduced profiled configuration. Expansion of apparatus 1200 is achieved by approximating the handle portions 1212 (not shown in FIG. 50), which causes the distal portions 1210 of the expander apparatus 1200 to move to a spaced apart configuration. As the distal portions 1210 move apart and contact the inner wall of the skirt portion 1024, it is expanded by allowing the floating rivet 1044 to slide within the two slots 1046 and 1048 of the skirt portion 1024. When the distal portions 1210 reach the maximum expansion of the skirt portion 1024 (illustrated by a dashed line), the shoulder 1228 and tab portion 1226 of the expander apparatus 1200 come into engagement to prevent further expansion of the tong portions (as illustrated in FIG. 48). The conduit 1020 may be alternatively further expanded with a balloon or similar device.

A subsequent, optional step in the procedure is to adjust the location of the distal portion of the expandable conduit relative to the body structures to be operated on. For example, the expander apparatus 1200 may also be used to engage the inner wall of the skirt portion 1024 of the expandable conduit 1020 in order to move the skirt portion 1024 of the expandable conduit 1020 to the desired location. For an embodiment in which the skirt portion 1024 of the expandable conduit 1020 is relatively movable relative to the proximal portion, e.g. by use of the rivet 1030, the expander apparatus 1200 is useful to position the skirt portion 1024 without substantially disturbing the proximal portion 1022 or the tissues closer to the skin surface of the patient. As will be described below, the ability to move the distal end portion, e.g., the skirt portion, without disturbing the proximal portion is especially beneficial when additional apparatus, as described below, is mounted relative to the proximal portion of the expandable conduit.

An endoscope mount platform 1300 and indexing arm 1400 provide securement of an endoscope 1500 on the proximal portion 1025 of access conduit 1020 for remotely viewing the surgical procedure, as illustrated in FIGS. 51-54. The endoscope mount platform 1300 also provides several functions during the surgical procedure. The endoscope mount platform 1300 includes a base 1302 that extends laterally from a central opening 1304 in a general ring-shaped configuration. For the physician who is primarily viewing the procedure by observing a monitor, the base 1302 provides an aid for the physician when inserting surgical instruments into the central opening 1304. For example, the size of the base 1302 provides visual assistance (as it may be observable in the physician's peripheral vision) as well as provides tactile feedback as the instruments are lowered towards the central opening 1304 and into the expandable conduit 1020.

The endoscope mount platform 1300 further provides a guide portion 1306, which extends substantially parallel to the longitudinal axis 1308 away from the central opening 1304. The base 1302 is typically molded as one piece with the guide portion 1306. The base 1302 and guide portion 1306 may be constructed as a suitable polymer such as polyetheretherketone (PEEK).

The guide portion 1306 includes a first upright member 1310 extending upward from the base 1302, and a second upright member 1312 extending upward from the base 1302. The upright members 1310 and 1312 each have a respective vertical grooves 1314 and 1315 for slidably receiving an endoscopic mount assembly 1318.

The endoscope 1500 (not shown in FIG. 51) is movably mounted to the endoscope mount platform 1300 by the endoscope mount assembly 1318 including endoscope mount 1320 and a saddle unit 1322. The saddle unit 1322 is slidably mounted within the grooves 1314 and 1315 in the upright members 1310 and 1312. The endoscope mount 1320 receives the endoscope 1500 through a bore 1326 which passes through the endoscope mount 1320. Part of the endoscope 1500 may extend through the expandable conduit 1020 substantially parallel to central axis 1308 into the patient's body 1130.

The endoscope mount 1320 is removably positioned in a recess 1328 defined in the substantially "U"-shaped saddle unit 1322, which is selectively movable in a direction parallel to the longitudinal axis 1308 in order to position the endoscope 1500 at the desired height within the expandable conduit 1020 to provide a zoom feature to physician's view of the surgical procedure.

A screw mechanism 1340 is positioned on the base 1302 and between the upright members 1310 and 1312, and is used to selectively move the saddle unit 1322 with the endoscope mount 1320 and the endoscope 1500. The screw mechanism 1340 comprises a thumb wheel 1342 and a spindle 1344. The thumb wheel 1342 is rotatably mounted in a bore in the base 1302. The thumbwheel has an external thread 1346 received in a cooperating thread in the base 1302. The spindle 1344 is mounted for movement substantially parallel to the central axis 1308. The spindle 1344 has a first end received in a rectangular opening in the saddle unit 1322, which inhibits rotational movement of the spindle unit 1344. The second end of the spindle 1344 has an external thread which cooperates with an internal thread formed in a bore within the thumbwheel 1342. Rotation of the thumb wheel 1342 relative to the spindle 1344, causes relative axial movement of the spindle unit 1344 along with the saddle unit 1322. Further details of the endoscope mount platform are described in U.S. patent application Ser. No. 09/491,808, filed Jan. 28, 2000, now U.S. Pat. No. 6,361,488, application Ser. No. 09/821,297, filed Mar. 29, 2001, now U.S. Pat. No. 6,530,880, and application Ser. No. 09/940,402, filed Aug. 27, 2001, and published as Publication No. 2003/0040656, all of which are incorporated by reference in their entirety herein.

Figure 52:
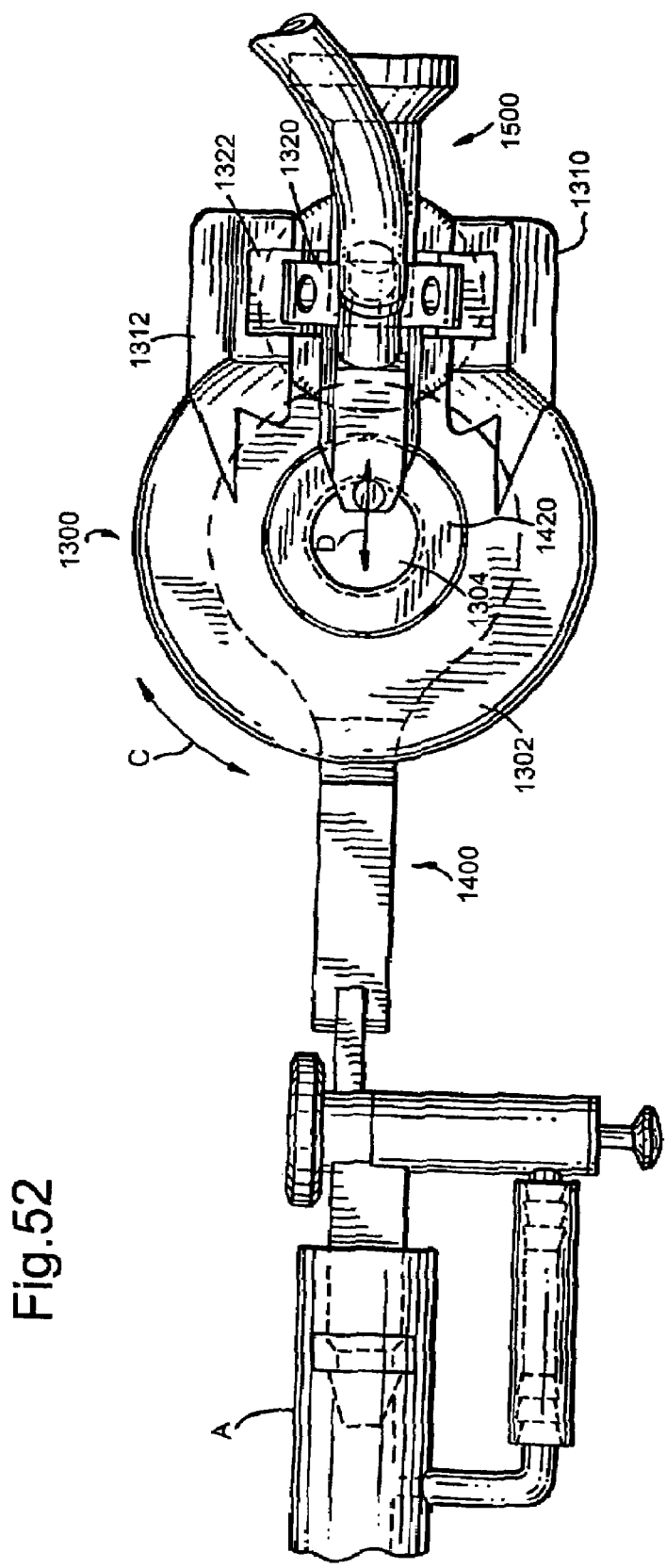
FIG. 52 is a top view of the apparatus of FIG. 51 illustrated with other apparatus.

As illustrated in FIGS. 52-54, the endoscope mount platform 1300 is mounted to the support arm 1400. The support arm 1400, in turn, is mounted to mechanical support, such as mechanical support arm A. The support arm 1400 rests on the proximal portion 1025 of the expandable conduit 1020. The support arm 1400 includes an indexing collar 1420, which is received in the central opening 1304 of the base 1302 of endoscope mount platform 1300. The indexing collar 1420 is substantially torroidal in section and has an outer peripheral wall 1422 and inner wall 1424 and a wall thickness 1426. The indexing collar further includes a flange 1428, which supports the indexing collar 1420 on the support arm 1400.

In order to support cannula or conduits 1020 of different dimensions, a plurality of indexing collars 1420 may be provided to accommodate each respective conduit size while using a single endoscope mount platform 1300. The central opening 1304 of the endoscope mount platform 1300 has constant dimension, e.g., a diameter of about 32.6 mm. An appropriate indexing collar 1420 is selected to support the respective conduit 1020. Thus the outer wall 1422 and the outer diameter 1430 are unchanged between different indexing collars 1420, although the inner wall 1424 and the inner diameter 1432 vary to accommodate differently sized conduits 1020.

The indexing collar 1420 is mounted to the proximal portion of the expandable conduit 1020 and allows angular movement of the endoscope mount platform 1300 with respect thereto about the central axis 1308 (as indicated by arrow C in FIG. 52). The outer wall 1422 of the index collar 1420 includes a plurality of hemispherical recesses 1450 for receiving one or more ball plungers 1350 on the endoscope mount platform 1300 (indicated in dashed line.) This mount configuration permits the endoscope mount platform 1300, along with the endoscope 1500 to be fixed in a plurality of discrete angular positions. Further details of the support arm and indexing collar are described in U.S. patent application Ser. No. 09/491,808, filed Jan. 28, 2000, now U.S. Pat. No. 6,361,488, application Ser. No. 09/821,297, filed Mar. 29, 2001, now U.S. Pat. No. 6,530,880, and application Ser. No. 09/940,402, filed Aug. 27, 2001, and published as Publication No. 2003/0040656, all of which are incorporated by reference hereinabove.

Figure 55:
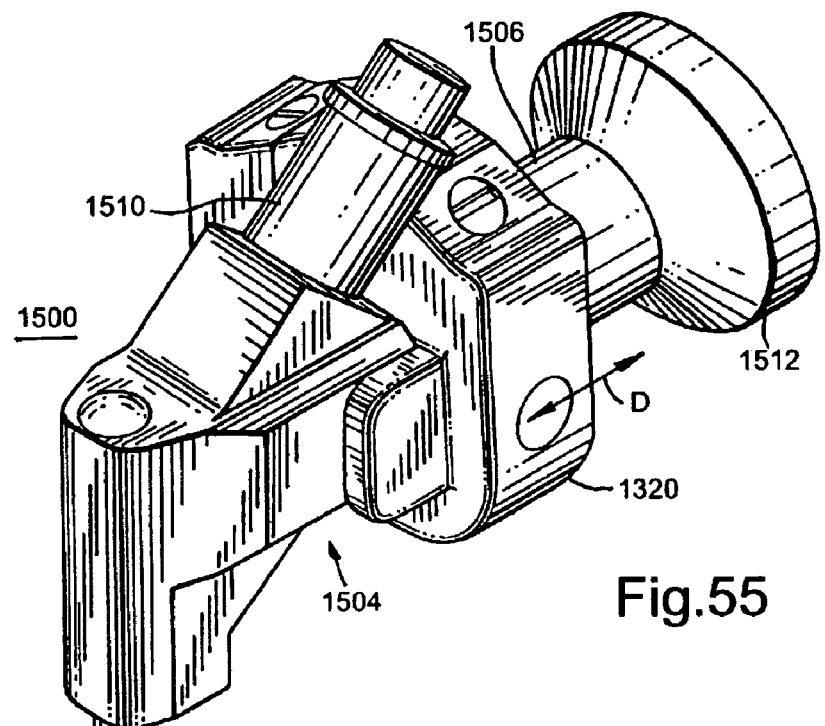
FIG. 55 is a perspective view of further apparatus according to another embodiment.

The endoscope, such as endoscope 1500 (FIG. 55), has an elongated configuration that extends into the expandable conduit 1020 in order to view the surgical site. In particular, endoscope 1500 has an elongated rod portion 1502 and a body portion 1504 which is substantially perpendicular thereto. In the exemplary embodiment, rod portion 1502 of endoscope 1500 has a diameter of about 4 mm and a length of about 106 mm. Body portion 1504 may define a tubular portion 1506 which is configured to be slidably received in the bore 1326 of endoscope mount 1320 as indicated by arrow D. The slidable mount of the endoscope 1500 on the endoscope mount 1300 permits the endoscope 1500 to adjust to configurations that incorporate different conduit diameters. Additional mobility of the endoscope 1500 in viewing the surgical site may be provided by rotating the endoscope mount platform 1300 about the central axis 1308 (as indicated by arrow C in FIG. 52).

The rod portion 1502 supports an optical portion (not shown) at a distal end 1508 thereof, which may define a field of view of about 105 degrees and a direction of view 1511 of about 25-30 degrees. An eyepiece 1512 is positioned at an end portion of the body portion 1504. The camera (not shown) is attached to the endoscope 1500 adjacent the eyepiece 1512 with a standard coupler unit. A light post 1510 supplies illumination to the surgical site at the distal end portion 1508. A preferred camera for use in the system and procedures described herein is a three chip unit that provides greater resolution to the viewed image than a single chip device.

Figure 56:
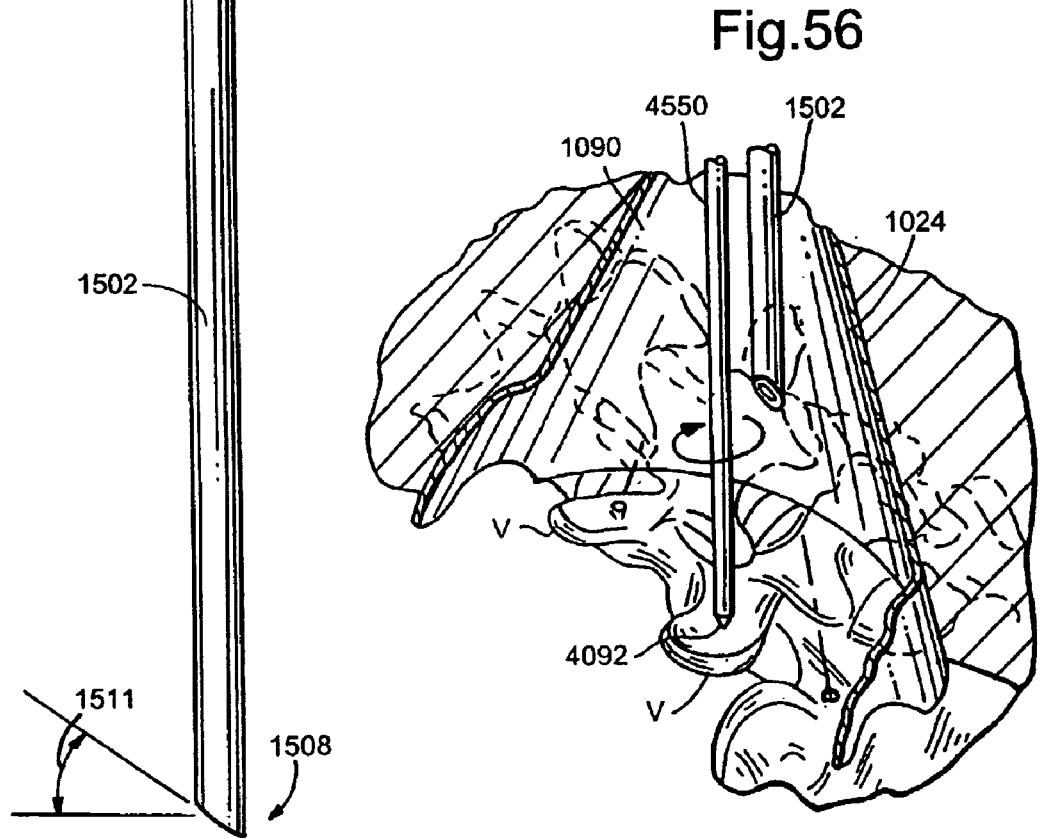
FIG. 56 is a view in partial section of a later stage in the procedure according to another embodiment.

A subsequent stage in the procedure is the placement of the support arm 1400 and the endoscope mount platform 1300 on the proximal portion 1025 of the expandable conduit 1020 (FIG. 53), and mounting of the endoscope 1500 on the endoscope mount platform 1300. A next step is insertion of surgical instrumentation into the expandable conduit to perform the surgical procedure on the body structures at least partially within the operative space defined by the expanded portion of the expandable conduit. In the exemplary method, skirt portion 1024 of expandable conduit 1020 at least partially defines operative space 1090 in which the surgical procedures described herein may be performed (FIG. 56). Depending upon the overlap of the skirt portion, the skirt portion may define a surface which is continuous about the circumference or which is discontinuous having one or more gaps where the material of the skirt portion does not overlap. For illustrative purposes, the surgical instrumentation described herein is useful to perform a two-level spinal fixation. Surgical instrumentation inserted into the expandable conduit is used for debridement and decortication. In particular, the soft tissue, such as fat and muscle, covering the vertebrae are removed in order to allow the physician to visually identify the various "landmarks," or vertebral structures, which enable the physician to locate the location for attaching the fasteners 4600 or other procedures, as will be described herein. Allowing visual identification of the vertebral structures enables the physician to perform the procedure while viewing the surgical area through the endoscope, microscope, loupes, etc., or in a conventional, open manner.

Tissue debridement and decortication of bone are completed using one or more debrider blades, bipolar sheath, high speed burr, and additional conventional manual instruments. The debrider blades are used to excise, remove and aspirate the soft tissue. The bipolar sheath is used to achieve hemostasis through spot and bulk tissue coagulation. The debrider blades and bipolar sheath are described in greater detail in U.S. Pat. No. 6,193,715, assigned to Medical Scientific, Inc., which is incorporated by reference in its entirety herein. The high speed burr and conventional manual instruments are also used to continue to expose the structure of the vertebrae.

Figure 67:
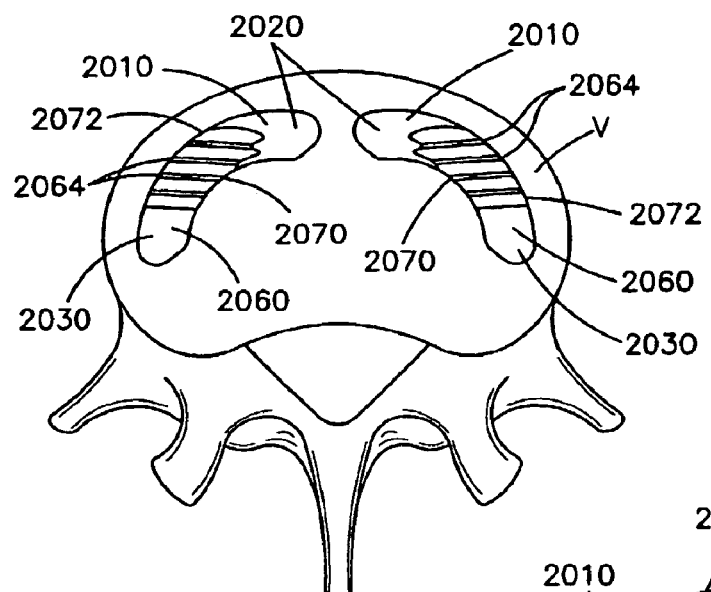
FIG. 67 is a view showing a pair of the spinal implants of FIG. 57 in first relative positions between adjacent vertebrae.
Figure 68:
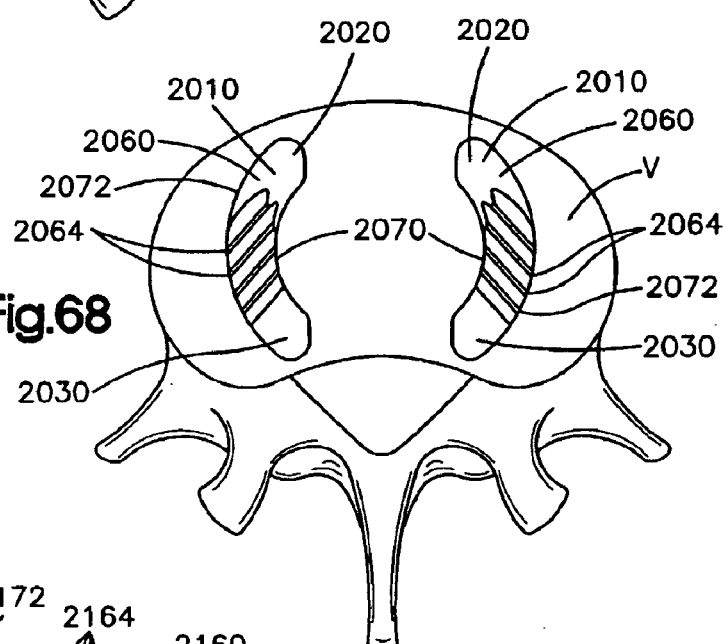
FIG. 68 is a view showing a pair of the spinal implants of FIG. 57 in second relative positions between adjacent vertebrae.

FIGS. 57-61 illustrate an embodiment of a fusion device or spinal implant 2010 that is inserted between the adjacent vertebrae. The spinal implant 2010 is placed between adjacent vertebrae to provide sufficient support to allow fusion of the adjacent vertebrae, as shown in FIGS. 67 and 68. The spinal implants 2010 are preferably made from an allograft material.

The spinal implant 2010 (FIGS. 57-61) has a first end 2020 for insertion between the adjacent vertebrae V. The first end 2020 has a tapered surface 2022 to facilitate insertion of the implant between the adjacent vertebrae V. The surface 2022 defines an angle X of approximately 45° as shown in FIG. 60.

Figure 70:
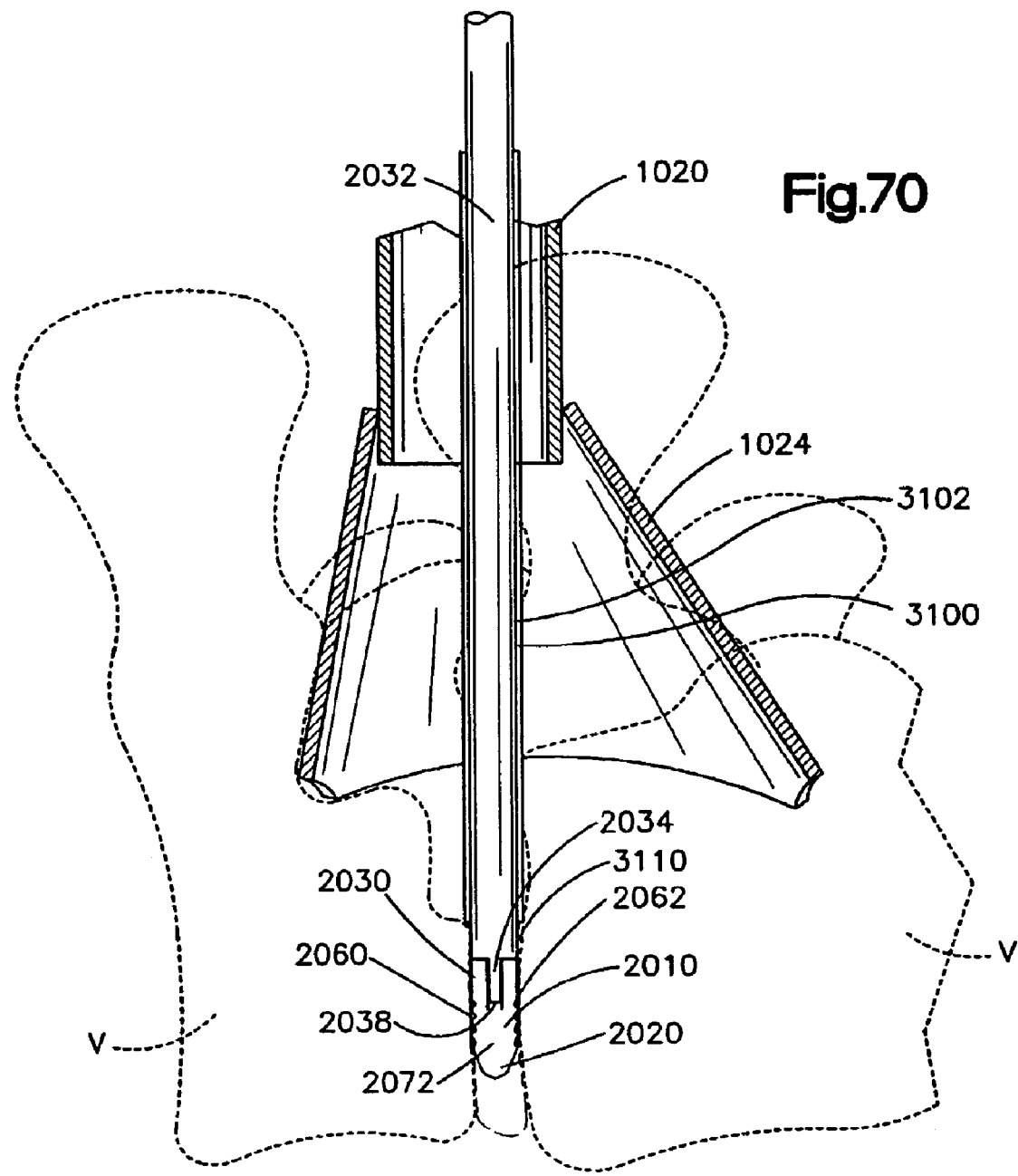
FIG. 70 is a view showing a spinal implant being inserted between the adjacent vertebrae according to another embodiment.
Figure 73:
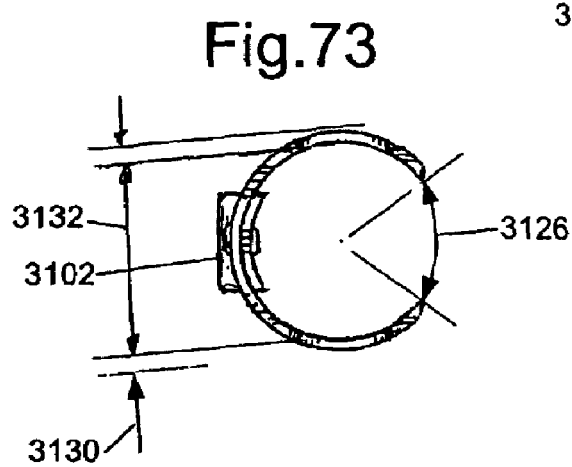
FIG. 73 is a top view of the apparatus of FIG. 71.
Figure 74:
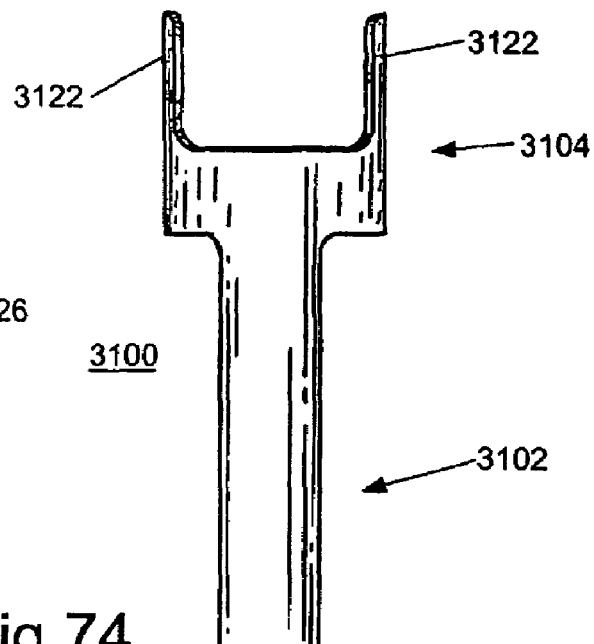
FIG. 74 is a back view of the apparatus of FIG. 71.
Figure 75:
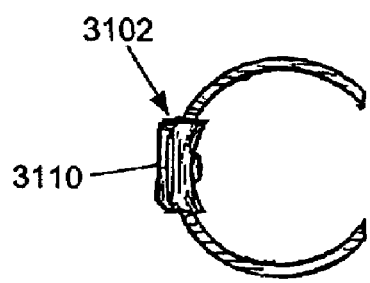
FIG. 75 is a bottom view of the apparatus of FIG. 71.

The spinal implant 2010 (FIGS. 57 and 58) has a second end 2030 that is engageable with a tool 2032 (FIG. 70) for inserting the implant between the adjacent vertebrae V. The tool 2032 has a pair of projections 2034, one of which is shown in FIG. 70, that extend into recesses 2036 and 2038 in the end 2030 of the implant 2010. The recesses 2036 and 2038 (FIGS. 57 and 58) extend from the second end 2030 toward the first end 2020. The recess 2036 (FIG. 60) is defined by an upper surface 2040 and a lower surface 2042 extending generally parallel to the upper surface 2040. The recess 2038 (FIG. 58) has a lower surface 2046 and an upper surface 2048 extending generally parallel to the lower surface 2046.

The recesses 2036 and 2038 define a gripping portion 2052. The projections 2034 on the tool 2032 extend into the recesses 2036 and 2038 and grip the gripping portion 2052. The projections 2034 engage the upper and lower surfaces 2040 and 2042 of the recess 2036 and the upper and lower surfaces 2046 and 2048 of the recess 2038. Accordingly, the tool 2032 grips the implant 2010 for inserting the implant between the adjacent vertebrae V.

The implant 2010 (FIGS. 57-60) has an upper surface 2060, as viewed in FIGS. 57-60, for engaging the upper vertebra V. The implant 2010 has a lower surface 2062, as viewed in FIGS. 57-60, for engaging the lower vertebra V. The upper and lower surfaces 2060 and 2062 extend from the first end 2020 to the second end 2030 of the implant 2010 and parallel to the upper and lower surfaces 2040, 2042, 2046, and 2048 of the recesses 2036 and 2038. The upper surface 2060 has teeth 2064 for engaging the upper vertebra V. The lower surface 2062 has teeth 2066 for engaging the lower vertebra V. Although FIGS. 57 and 58 show four teeth 2064 and four teeth 2066, it is contemplated that any number of teeth could be used.

A first side surface 2070 and a second side surface 2072 extend between the upper and lower surfaces 2060 and 2062. The first side surface 2070 extends along a first arc from the first end 2022 of the implant 2010 to the second end 2030. The second side surface 2072 extends along a second arc from the first end 2022 to the second end 2030. The first and second side surfaces 2070 and 2072 are concentric and define portions of concentric circles. The teeth 2064 and 2066 parallel to each other and extend between the side surfaces 2070 and 2072 and along secant lines of the concentric circles defined by the side surfaces.

The implant 2010 is formed by harvesting allograft material from a femur, as known in the art. The femur is axially cut to form cylindrical pieces of allograft material. The cylindrical pieces are then cut in half to form semi-cylindrical pieces of allograft material. The semi-cylindrical pieces of allograft material are machined into the spinal implants 2010.

A pair of spinal implants 2010 may be placed bilaterally between the adjacent vertebrae V. The cannula or expandable conduit 1020 is inserted into the patient's body adjacent the vertebrae V. The skirt portion 1024 of the cannula 1020 is radially expanded to provide a working space adjacent the vertebrae V. Disc material between the vertebrae V is removed using instruments such as kerrisons, rongeurs, or curettes. A microdebrider may also be utilized to remove the disc material. An osteotome, curettes, and scrapers are used to prepare end plates of the vertebrae V for fusion. Preferably, an annulus of the disc is left between the vertebrae V.

Distracters are used to sequentially distract the disc space until the desired distance between the vertebrae V is achieved. The fusion device or implant 2010 is placed between the vertebrae V using the tool 2032. The first end 2020 of the implant 2010 is inserted first between the vertebrae V. The implant 2010 is pushed between the vertebrae V until the end 2030 of the implant is between the vertebrae. A second spinal implant 2010 is inserted on the ipsilateral side using the same procedure.

A shield apparatus 3100 with an elongated portion 3102 may be used to facilitate insertion of the implants 2010 between the vertebrae V. A distal portion 3110 of the apparatus 3100 may be placed in an annulotomy. The implant 2010 is inserted with the side surface 2170 facing the elongated portion 3102 so that the apparatus 3100 can act as a "shoe horn" to facilitate or guide insertion of the implants 2010 between the vertebrae.

The implants 2010 may be inserted between the vertebrae V with the first ends 2020 located adjacent each other and the second ends 2030 spaced apart from each other, as shown in FIG. 67. The implants 2010 may also be inserted between the vertebrae V with the first ends 2020 of the implants 2010 spaced apart approximately the same distance that the second ends 2030 are spaced apart. It is contemplated that the implants 2010 may be inserted in any desired position between the vertebrae V. It is also contemplated that only one implant 2010 may be inserted between the vertebrae V. Furthermore, it is contemplated that the implants 2010 may be inserted between vertebrae using an open procedure.

Figure 69:
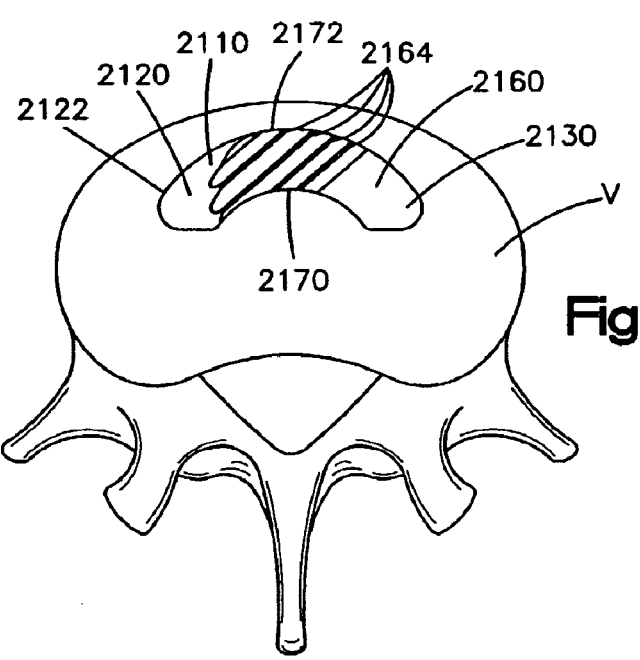
FIG. 69 is a view showing the spinal implant of FIG. 62 between adjacent vertebrae.

Another embodiment of a fusion device or spinal implant 2110 is illustrated in FIGS. 62-66. The spinal implant 2110 is substantially similar to the embodiment disclosed in FIGS. 57-61. The implant 2110 is placed between the adjacent vertebrae V to provide sufficient support to allow fusion of the adjacent vertebrae, as shown in FIG. 69. The spinal implant 2110 is preferably made from an allograft material.

Figure 65:
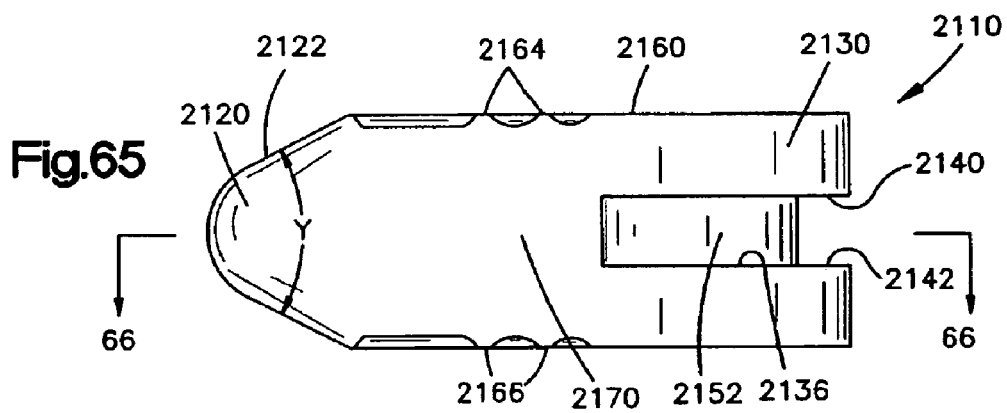
FIG. 65 is a side view of the spinal implant of FIG. 62 showing the first side surface.
Figure 66:
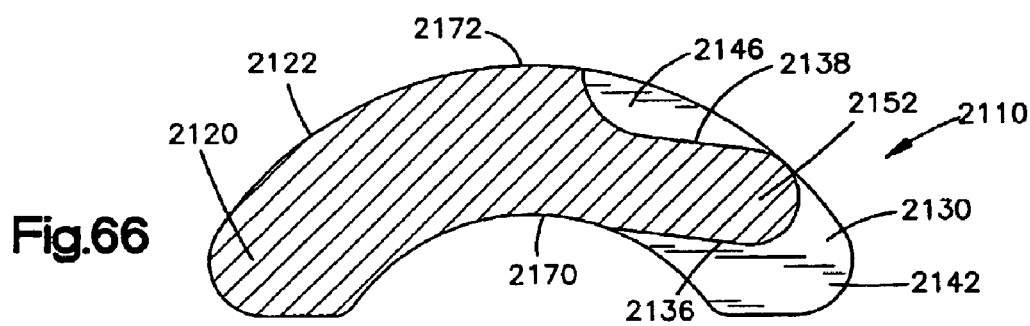
FIG. 66 is a cross-sectional view of the spinal implant taken along the line 66-66 in FIG. 65.

The spinal implant 2110 (FIGS. 62-66) has a first end 2120 for insertion between the adjacent vertebrae V. The first end 2120 has a tapered surface 2122 to facilitate insertion of the implant between the adjacent vertebrae V. The surface 2122 defines an angle Y of approximately 45° as shown in FIG. 65.

The spinal implant 2110 (FIGS. 62 and 63) has a second end 2130 that is engageable with the projections 2034 on the tool 2032 for inserting the implant between the adjacent vertebrae V. The projections 2034 extend into recesses 2136 and 2138 in the end 2130 of the implant 2110. The recesses 2136 and 2138 extend from the second end 2130 toward the first end 2120. The recess 2136 (FIGS. 62 and 65) is defined by an upper surface 2140 and a lower surface 2142 extending generally parallel to the upper surface 2140. The recess 2138 (FIG. 63) has a lower surface 2146 and an upper surface 2148 extending generally parallel to the lower surface 2146.

The recesses 2136 and 2138 define a gripping portion 2152. The projections 2034 on the tool 2032 extend into the recesses 2136 and 2138 and grip the gripping portion 2152. The projections 2034 engage the upper and lower surfaces 2140 and 2142 of the recess 2136 and the upper and lower surfaces 2146 and 2148 of the recess 2138. Accordingly, the tool 2032 grips the implant 2110 for inserting the implant between the adjacent vertebrae V.

Figures 62, 63:
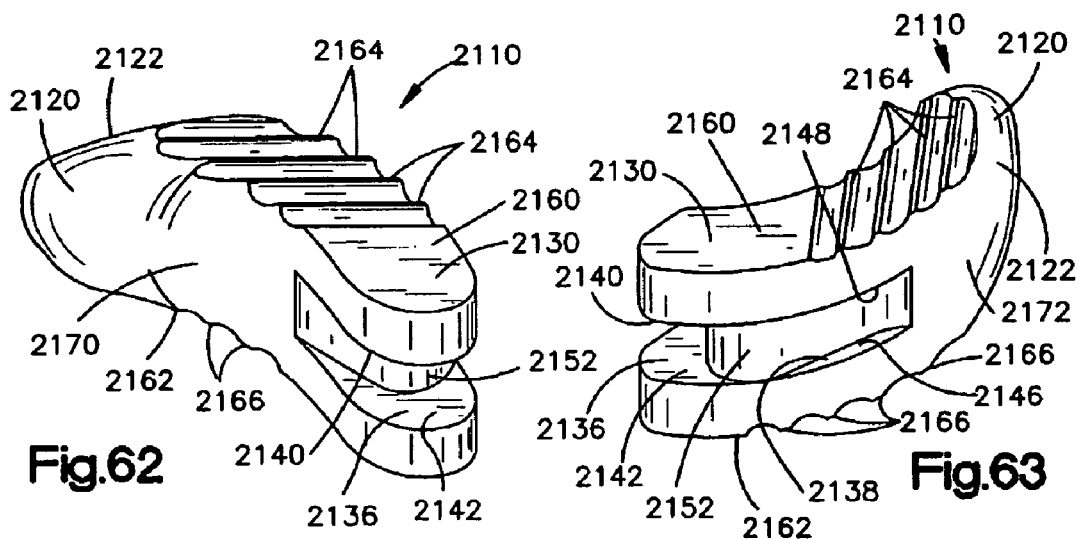
FIG. 62 is a perspective view of another embodiment of a spinal implant constructed according to another embodiment showing a first side surface of the spinal implant.
FIG. 63 is a perspective view of the spinal implant of FIG. 62 showing a second side surface of the spinal implant.
Figure 64:
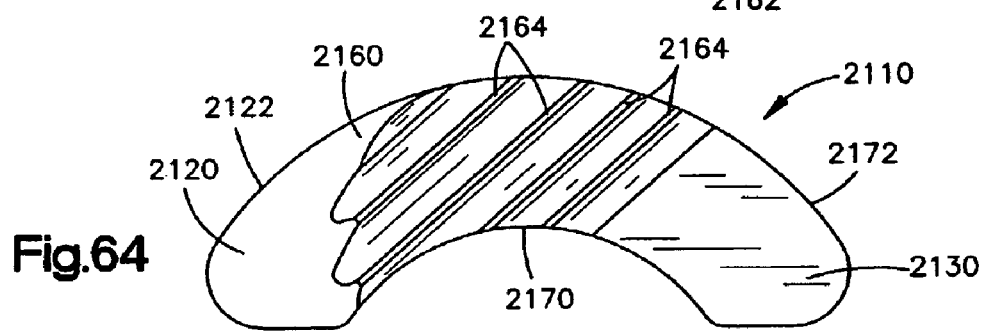
FIG. 64 is a plan view of the spinal implant of FIG. 62 showing an upper surface of the spinal implant.

The implant 2110 (FIGS. 62-65) has an upper surface 2160, as viewed in FIGS. 62-65, for engaging the upper vertebra V. The implant 2110 has a lower surface 2162, as viewed in FIGS. 62-65, for engaging the lower vertebra V. The upper and lower surfaces 2160 and 2162 extend from the first end 2120 to the second end 2130 of the implant 2110 and parallel to the upper and lower surfaces 2140, 2142, 2146, and 2148 of the recesses 2136 and 2138. The upper surface 2160 has teeth 2164 for engaging the upper vertebra V. The lower surface 2162 has teeth 2166 for engaging the lower vertebra V. Although FIG. 63 shows four teeth 2164 and four teeth 2166, it is contemplated that any number of teeth could be used.

A first side surface 2170 and a second side surface 2172 extend between the upper and lower surfaces 2160 and 2162. The first side surface 2170 extends along a first arc from the first end 2122 of the implant 2110 to the second end 2130. The second side surface 2172 extends along a second arc from the first end 2120 to the second end 2130. The first and second side surfaces 2170 and 2172 are concentric and define portions of concentric circles. The teeth 2164 and 2166 extend parallel to each other and between the side surfaces 2170 and 2172 along secant lines of the concentric circles defined by the side surfaces.

The implant 2110 is formed by harvesting allograft material from a femur, as is known in the art. The femur is axially cut to form cylindrical pieces of allograft material. The cylindrical pieces are then cut in half to form semi-cylindrical pieces of allograft material. The semi-cylindrical pieces of allograft material are machined into the spinal implants 2110.

A spinal implant 2110 is placed unilaterally between the adjacent vertebrae V. The cannula 1020 is inserted into the patient's body adjacent the vertebrae V. The skirt portion 1024 of the cannula 1020 is radially expanded to provide a working space adjacent the vertebrae V. Disc material between the vertebrae V is removed using instruments such as kerrisons, rongeurs, or curettes. A microdebrider may also be utilized to remove the disc material. An osteotome, curettes, and scrapers are used to prepare end plates of the vertebrae V for fusion. Preferably, an annulus of the disc is left between the vertebrae V.

Distracters are used to sequentially distract the disc space until the desired distance between the vertebrae V is achieved. The implant 2110 is placed between the vertebrae V using the tool 2032. It is contemplated that the apparatus 3100 could be used also. The first end 2120 of the implant 2110 is inserted first between the vertebrae V. The implant 2110 is pushed between the vertebrae V until the end 2130 of the implant is between the vertebrae. It is contemplated that the implant 2110 may be inserted in any desired position between the vertebrae V. It is also contemplated that more than one implant 2110 may be inserted between the vertebrae.

The apparatus or shield 3100 for use in placing the fusion devices or spinal implants between the vertebrae is illustrated in FIGS. 71-75. The apparatus 3100 includes an elongated body portion 3102, which protects the nerve root or dura, and a mounting portion 3104, which allows for the surgeon to releasably mount the apparatus 3100 to the cannula 1020. Consequently, the surgeon is able to perform the surgical procedures without requiring the surgeon or an assistant to continue to support the apparatus 3100 throughout the procedure, and without reducing the field of view.

The apparatus 3100 may be manufactured from a biocompatible material such as, but not limited to, stainless steel. In the exemplary embodiment, apparatus 3100 is manufactured from stainless steel having a thickness of about 0.02 inches to about 0.036 inches. The elongated body portion 3102 has dimensions which correspond to the depth in the body in which the procedure is being performed, and to the size of the body structure which is to be shielded by elongated body portion 3102. In the exemplary embodiment, the elongated body portion 3102 has a width 3106 of about 0.346 inches and a length of about 5.06 inches (FIG. 72), although other dimensions would be appropriate for spinal surgical procedures performed at different locations, or for surgical procedures involving different body structures. The distal tip portion 3110 of the apparatus 3100 may have a slightly curved "bell mouth" configuration which allows for atraumatic contact with a body structure, such as a nerve. It is contemplated that the elongated body portion may have any desired shape.

The mounting portion 3104 allows the apparatus 3100 to be secured to a support structure in any number of ways. In the exemplary embodiment, mounting portion 3104 may include a ring portion. With reference to FIGS. 71-75, ring portion 3120 has a substantially ring-shaped configuration with an opening 3124, which defines an angle 3126 of about 90 degrees of the total circumference of the ring portion 3120. As will be described in greater detail below, the angle 3126 is a nominal value, because the ring portion 3104 is resilient, which permits the opening 3124 to change size during the mounting process.

In the exemplary embodiment, the mounting portion 3104 has a substantially cylindrical configuration in order to be mounted within the interior lumen of the cannula 1020, as will be described below. The ring portion 3104 has an exterior dimension 3130 of about 0.79 inches, and an interior dimension 3132 of about 0.76 inches. It is understood that the dimensions of the ring portion 3104 would be different if the expandable conduit 1020 has a different interior dimension. Moreover, the cylindrical shape of the ring portion 3104 would change if the apparatus 3100 is used with a support member having a differently shaped internal lumen.

Finger grip portions 3122 extend from the mounting portion 3104 and allow the surgeon to apply an inwardly directed force (as indicated by arrows A) to the ring portion 3120. The resilient characteristics of the ring portion 3120 allow the material to deflect thereby reducing the exterior dimension 3130 and reducing the spacing 3124. Releasing the finger grip portions 3122 allows the ring portion to move towards its undeflected condition, thereby engaging the interior wall of the expandable conduit 1020.

The elongated body portion 3102 and the mounting portion 3104 may be manufactured from a single component, such as a sheet of stainless steel, and then the mounting portion 3104 may be subsequently formed into a substantially cylindrical shape. In another embodiment, the mounting portion 3104 may be manufactured as a separate component and attached to the elongated body portion, by techniques such as, but not limited to welding and securement by fasteners, such as rivets.

The expandable conduit 1020 serves as a stable mounting structure for apparatus 3100. In particular, mounting portion 3104 is releasably mounted to the interior wall of proximal wall portion 1022 of expandable conduit 1020. Elongated body portion 3102 extends distally into the operative site to protect the desired body structure, such as the nerve, as will be described below.

Figure 77:
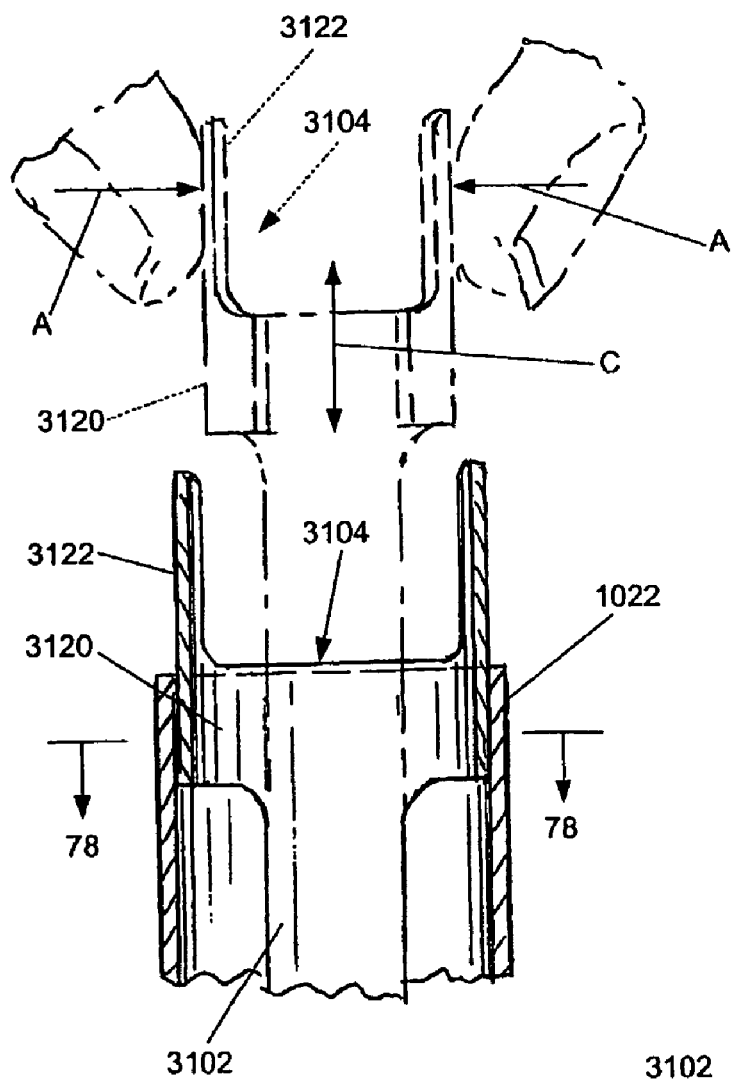
FIG. 77 is a longitudinal sectional view of the apparatus of FIG. 76 taken from line 77-77 of FIG. 76.
Figure 78:
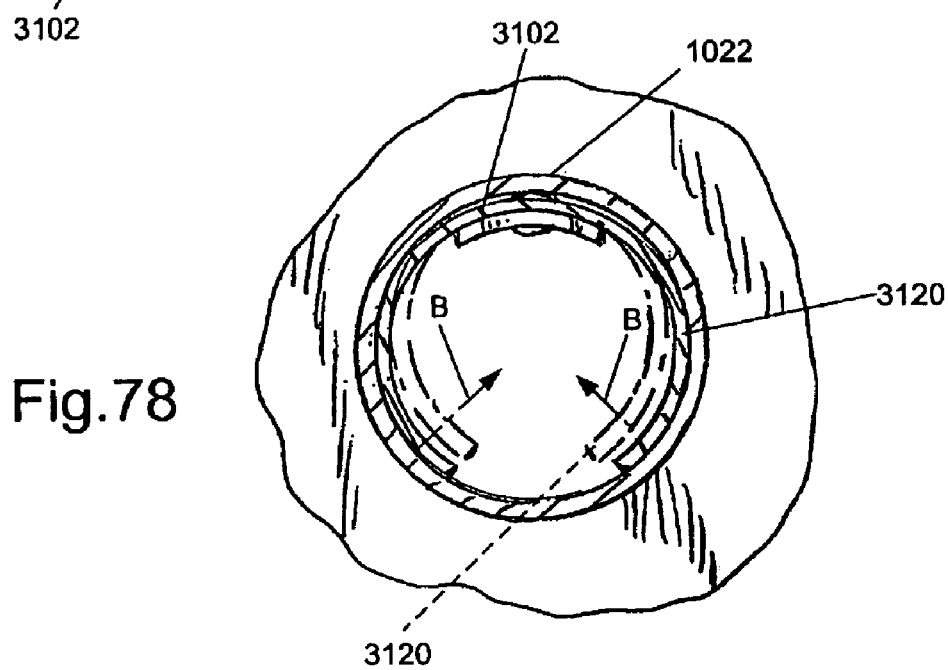
FIG. 78 is a transverse sectional view of the apparatus of FIG. 77 taken from line 78-78 of FIG. 77.

To install the apparatus 3100 within the interior passage of the proximal wall portion 1022, the surgeon may apply an inwardly directed force on the ring portion 3120, thereby causing the ring portion to resiliently deform, as illustrated by dashed line and arrows B in FIG. 78. The surgeon subsequently inserts the apparatus 3100 into the interior lumen of the proximal wall portion 1022 (as indicated by arrow C) to the position of ring portion 3104 illustrated in solid line in FIG. 77. When the surgeon releases the finger grip portions 3122, the ring portion 3120 resiliently moves towards its undeflected configuration, thereby engaging the interior lumen of the proximal wall portion 1022. The mounting portion 3104 described herein has the advantage that it is easily removed and/or moved with respect to the conduit 1020 without disturbing the position of the conduit 1020 or any other instrumentation.

Figure 76:
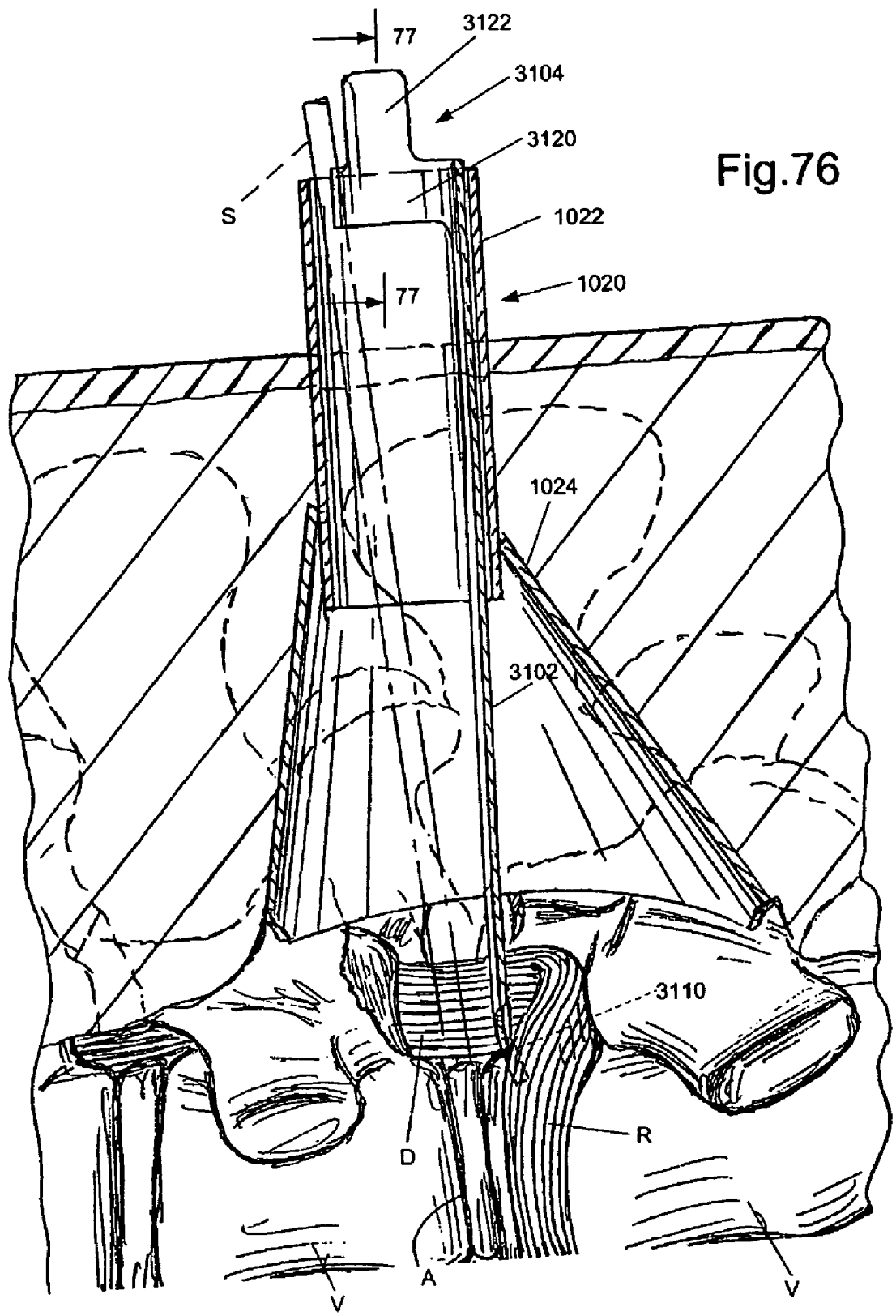
FIG. 76 is a sectional view of the apparatus of FIG. 71, used in conjunction with additional structure in a patient.

As illustrated in FIG. 76, the configuration of the mounting portion 3104 and the elongated body portion 3102 allow the elongated body portion to occupy a small space along the periphery of the proximal wall portion 3122. This allows the apparatus to protect the desired body structure without blocking access for the insertion of other surgical instrumentation, and without blocking visibility by the surgeon during the procedure.

The mounting portion 3104 is one exemplary configuration for mounting the apparatus 3100 to the support structure. It is contemplated that the apparatus 3100 may be mounted within the cannula in another manner.

When in position, the distal end portion 3110 covers the exiting nerve root R, while exposing the disc annulus A (See FIG. 76). As discussed above, the debridement and decortication of tissue covering the vertebrae, as well as a facetecomy and/or laminectomy if indicated, are performed prior to the insertion of apparatus 3100 into the surgical space. Thus, there is no need to displace or retract tissue, and apparatus 3100 merely covers the nerve root and does not substantially displace the nerve root or any other body tissue. It is understood that term "cover" as used herein refers to apparatus 3100 being a small distance adjacent to the body structure, or in contact with the body structure without applying significant tension or displacement force to the body structure.

Additional surgical instrumentation S may be inserted into the expandable conduit to perform procedures on the surrounding tissue. For example, an annulotomy may be performed using a long handled knife and kerrisons. A discectomy may be completed by using curettes and rongeurs. Removal of osteophytes which may have accumulated between the vertebrae may be performed using osteotomes and chisels.

Figure 79:
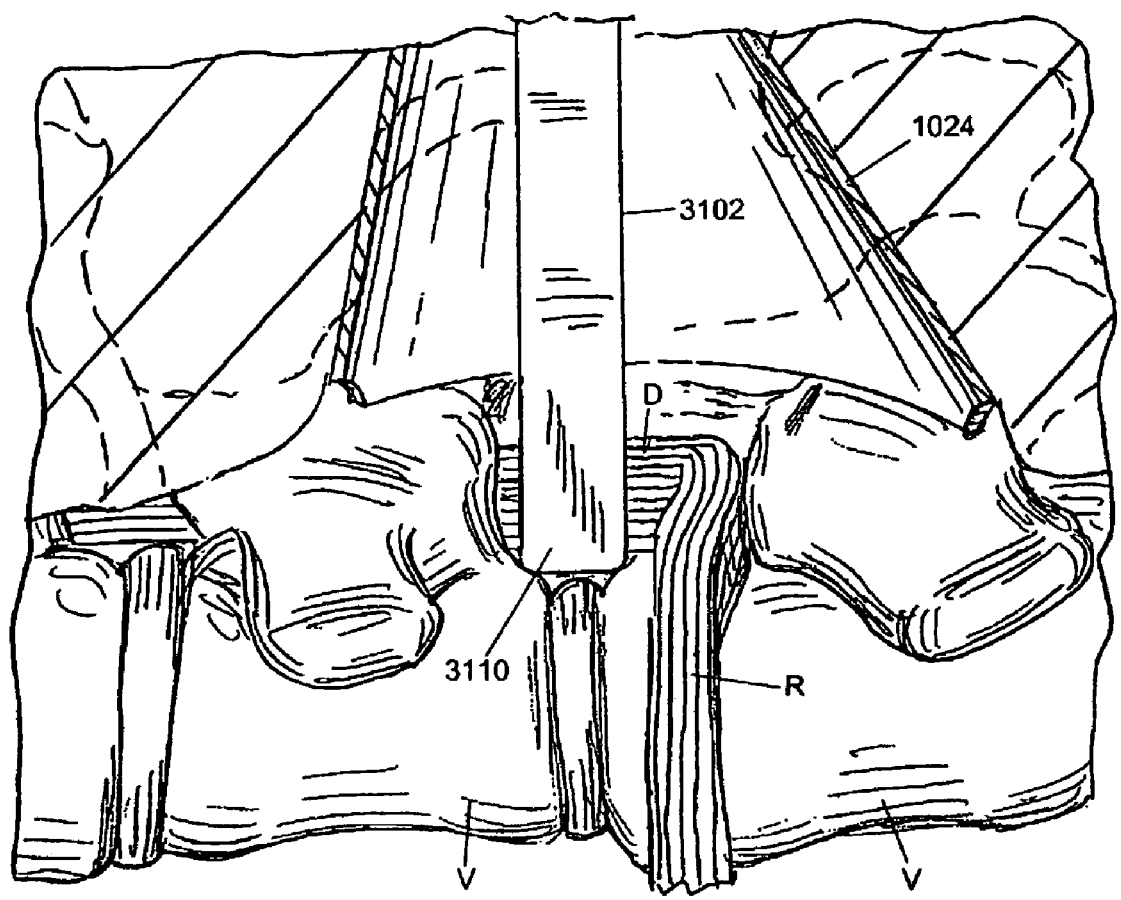
FIG. 79 is a sectional view, similar to FIG. 76, illustrating an alternative position of the apparatus of FIG. 71.

As illustrated in FIG. 79, the elongated body portion 3102 is rotated to protect the spinal cord, or dura D, during the above procedures. The surgeon may change the position of the apparatus 3100 by approximating the finger grips 3122 to release the ring portion from engagement with the inner wall of the proximal wall portion 1020, and then re-position the apparatus 3100 without disturbing the expandable conduit 1020 (as shown in FIG. 77).

Figure 80:
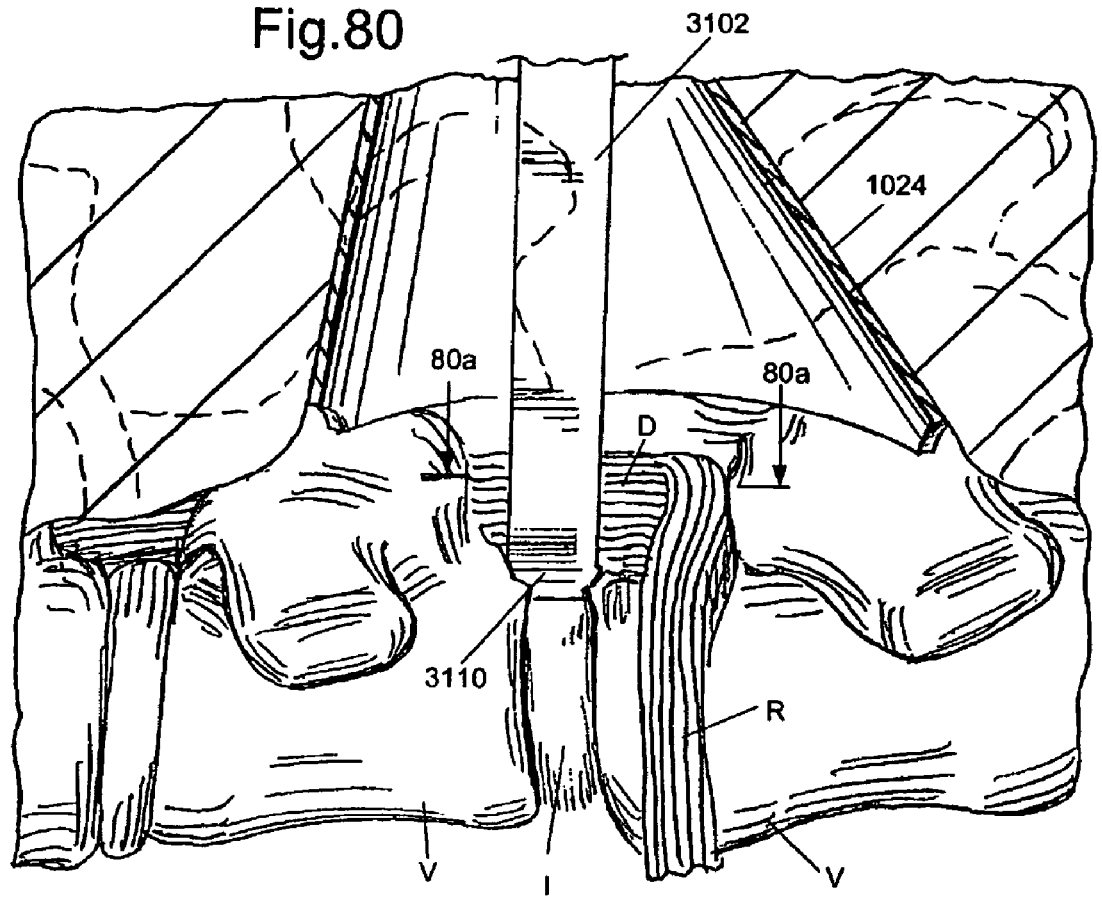
FIG. 80 is a sectional view, similar to FIG. 76, illustrating another alternative position of the apparatus of FIG. 71.
Figure 80A:
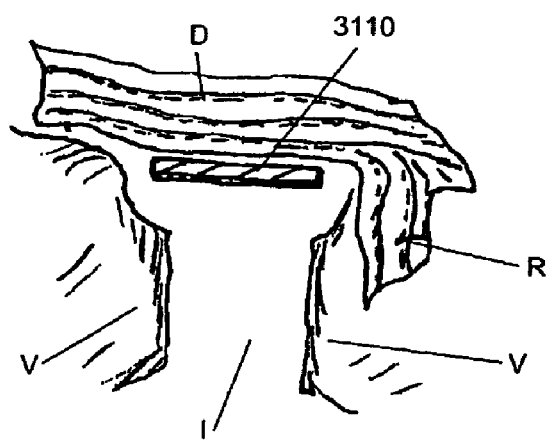
FIG. 80a is a transverse sectional view of the apparatus of FIG. 80, taken along lines 80a-80a of FIG. 80.

During certain surgical procedures, it may be useful to introduce crushed bone fragments or the fusion devices 2010 or 2110 to promote bone fusion. As illustrated in FIGS. 80-80a, apparatus 3100 is useful to direct the implants into the space I between adjacent vertebrae V. As shown in the figures, the distal portion 3110 of the elongated body portion 3102 is partially inserted into the space I. The distal end portion 3110, is positioned between adjacent vertebrae V, and creates a partially enclosed space for receiving the implants or other material therein.

Another embodiment of the apparatus or shield is illustrated in FIGS. 81-82, and designated apparatus 3200. Apparatus 3200 is substantially identical to apparatus 3100, described above, with the following differences noted herein. In particular, distal end portion 3210 includes a pair of surfaces 3240 and 3242. Surface 3240 is an extension of elongated shield portion 3202, and surface 3242 extends at an angle with respect to surface 3240. In the exemplary embodiment, surfaces 3240 and 3242 defined an angle of about 90 degrees between them. Alternatively another angle between surfaces 3240 and 3242 may be defined as indicated by the body structures to be protected.

Figure 83:
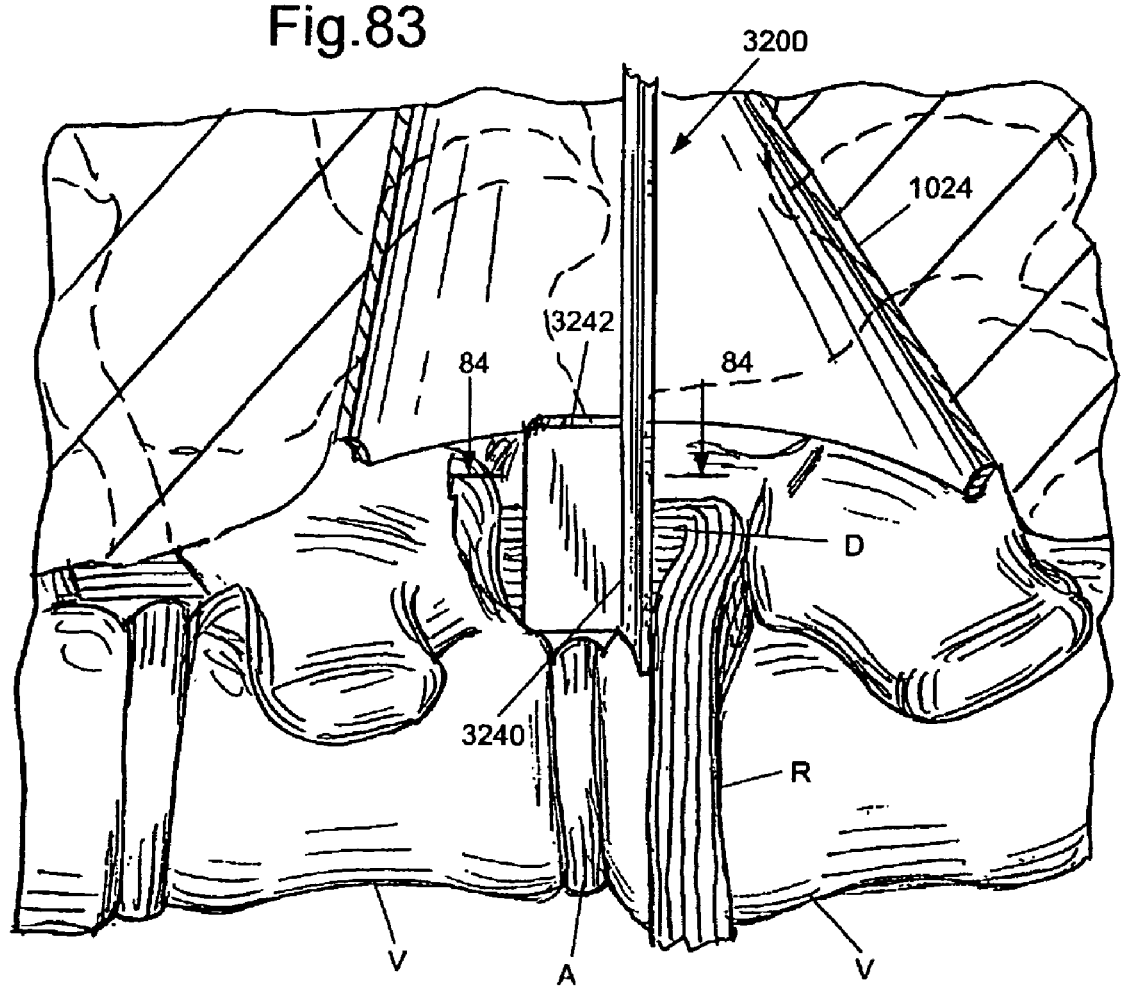
FIG. 83 is a sectional view, similar to FIG. 76, of the apparatus of FIGS. 81-82, used in conjunction with additional structure in a patient.
Figure 84:
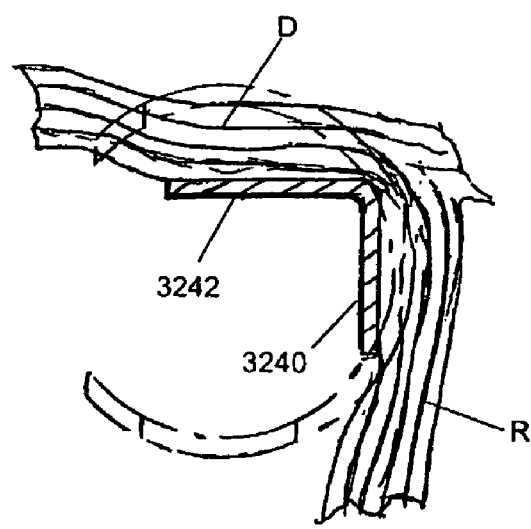
FIG. 84 is a transverse sectional view of the apparatus of FIGS. 81-82, taken along lines 84-84 of FIG. 83.

Distal end portion 3210 allows the apparatus to provide simultaneous shielding of both the dura D and the nerve root R. In FIGS. 83-84, surface 3242 shields the dura D, and surface 3240 shields the nerve root R. It is understood that surfaces 3240 and 3242 may be interchanged with respect to which tissue they protect during the surgical procedure.

After the spinal implants 2010 or 2110 are inserted between the vertebrae V, the fasteners 4600 are attached to the vertebrae. Prior to attachment of the fasteners, the location of the fastener attachment is confirmed. In the exemplary embodiment, the pedicle entry point of the L5 vertebra is located using visual landmarks as well as lateral and A/P fluoroscopy, as is known in the art. With reference to FIG. 56, the entry point 4092 is prepared with an awl 4550. The pedicle hole 4092 is completed using instruments known in the art such as a straight bone probe, a tap, and a sounder. The sounder, as is known in the art, determines whether the hole that is made is surrounded by bone on all sides, and that there has been no perforation of the pedicle wall.

After hole 4092 in the pedicle is provided (or at any point during the procedure), an optional step is to adjust the location of the distal portion 1024 of the expandable conduit 1020. This may be performed by inserting the expander apparatus 1200 into the expandable conduit 1020, expanding the distal portions 1210, and contacting the inner wall of the skirt portion 1024 to move the skirt portion 1024 to the desired location. This step may be performed while the endoscope 1500 is positioned within the expandable conduit 1020, and without substantially disturbing the location of the proximal portion of the expandable conduit 1020 to which the endoscope mount platform 1300 may be attached.

Figure 85:
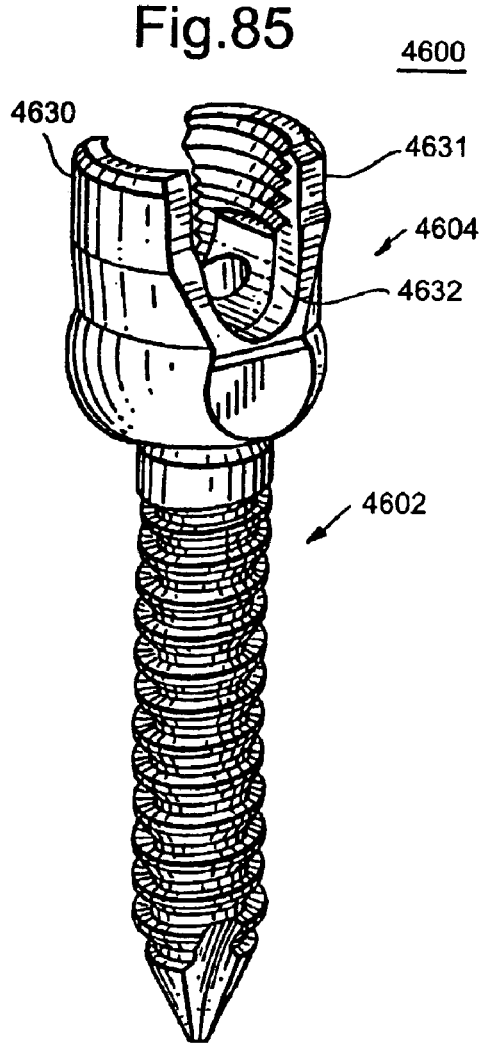
FIG. 85 is a perspective view of an apparatus according to another embodiment.
Figure 86A:
FIG. 86a is an enlarged side view of a component illustrated in FIG. 86.
Figure 86:
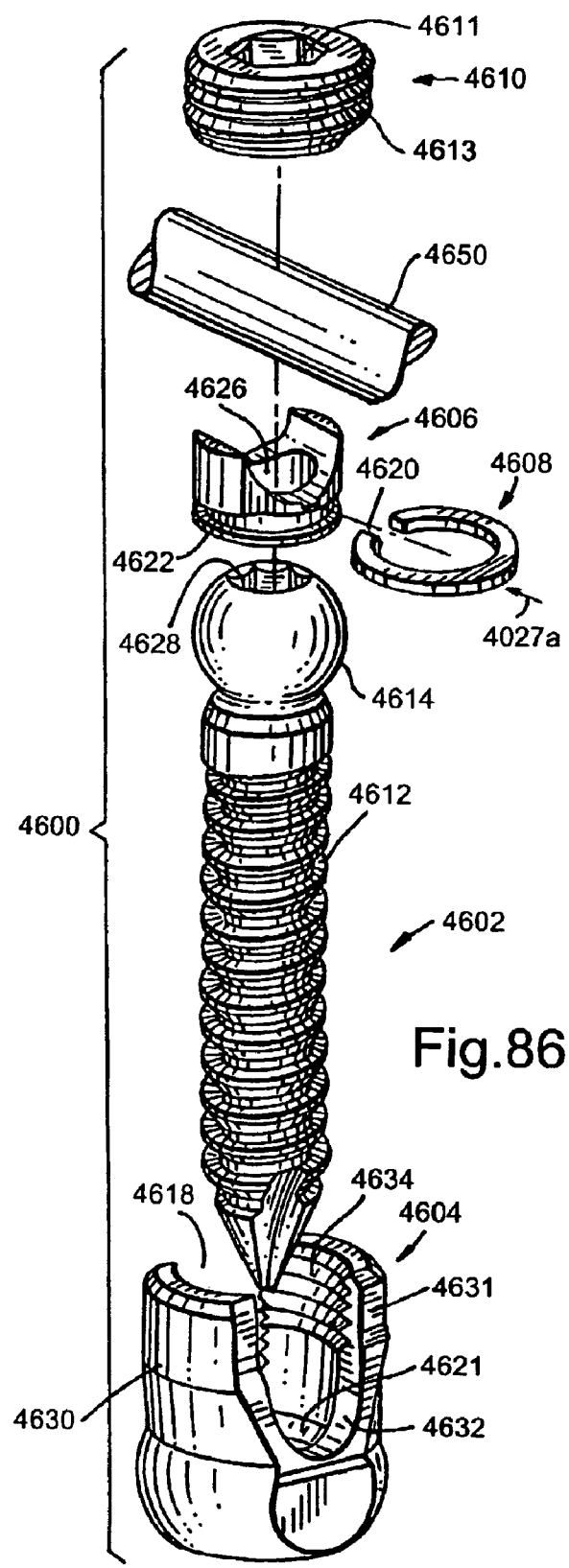
FIG. 86 is a perspective view with parts separated of the apparatus of FIG. 85.

A particularly useful fastener for use in the exemplary procedure is the fastener 4600, illustrated in FIGS. 85-86, and described in greater detail in U.S. patent application Ser. No. 10/075,668, filed Feb. 13, 2002 and in application Ser. No. 10/087,489, filed Mar. 1, 2002, which are hereby incorporated by reference in their entirety herein. Fastener 4600 includes a screw portion 4602, a housing 4604, a spacer member 4606, a biasing member 4608, and a clamping member, such as cap screw 4610. The screw portion 4602 has a distal threaded portion 4612 and a proximal, substantially spherical joint portion 4614. The threaded portion 4612 is inserted into the hole 4092 in the vertebrae, as will be described below. The substantially spherical joint portion 4614 is received in a substantially annular, part spherical recess 4616 in the housing 4604 in a ball and socket joint relationship (see also FIG. 88).

As illustrated in FIG. 86, the fastener is assembled by inserting the screw portion 4602 into a bore in a passage 4618 in the housing 4604, until the joint portion 4614 engages the annular recess 4616. The screw portion 4602 is retained in the housing 4604 by the spacer member 4606 and biasing member 4608. The biasing member 4608 provides a biasing force to drive the spacer member 4606 in frictional engagement with the joint portion 4614 of the screw member 4602 and the annular recess 4616 of the housing 4604. The biasing provided by the biasing member 4608 frictionally maintains the relative positioning of the housing 4604 with respect to the screw portion 4602. The biasing member 4608 is selected such that biasing force prevents unrestricted movement of the housing 4604 relative to the screw portion 4602. However, the biasing force is insufficient to resist the application of force by a physician to move the housing 4604 relative to the screw portion 4602. In other words, this biasing force is strong enough to maintain the housing 4604 stationary relative to the screw portion 4602, but this force may be overcome by the physician to reorient the housing 4604 with respect to the screw member 4602, as will be described below.

In the exemplary embodiment, the biasing member 4608 is a resilient ring having a gap 4620, which permits the biasing member 4608 to radially contract and expand. The biasing member 4608 has an arched shape, when viewed end-on (FIG. 86a). The arch shape of the spring member 4608 provides the biasing force, as will be described below. The spacer member 4606 and the biasing member 4608 are inserted into the housing 4604 by radially compressing the biasing member into an annular groove 4622 in the spacer member 4606. The spacer member 4606 and the biasing member 4608 are slid into the passage 4618 until the distal surface of the spacer member 4606 engages the joint portion 4614 of the screw portion 4602, and the biasing member 4608 expands radially into the annular groove 4620 in the housing 4604. The annular groove 4620 in the housing 4604 has a dimension 4623 which is smaller than the uncompressed height of the arched shape of the biasing member 4608. When the biasing member 4608 is inserted in the annular groove 4620, the biasing member 4608 is flattened against its normal bias, thereby exerting the biasing force to the spacer member 4606. It is understood that similar biasing members, such as coiled springs, belleville washers, or the like may be used to supply the biasing force described herein.

The spacer member 4606 is provided with a longitudinal bore 4626, which provides access to a hexagonal recess 4628 in the proximal end of the joint portion 4614 of the screw member 4602. The proximal portion of the housing 4604 includes a pair of upright members 4630 and 4631 that are separated by substantially "U"-shaped grooves 4632. A recess for receiving elongated member 4650 is defined by the pair of grooves 4632 between upright members 4630 and 4631. Elongated member 4650 is to be placed distally into the housing 4604 in an orientation substantially transverse to the longitudinal axis of the housing 4604, as will be described below. The inner walls of the upright members 4630 and 4631 are provided with threads 4634 for attachment of the cap screw 4610 by threads 4613 therein.

The fastener 4600 is inserted into the expandable conduit 1020 and guided to the prepared hole 4092 in the vertebrae as a further stage of the procedure. The fastener 4600 must be simultaneously supported and rotated in order to be secured in hole 4092. In the exemplary embodiment, the fastener 4600 is supported and attached to the bone by an endoscopic screwdriver apparatus 4660, illustrated in FIG. 87. Screwdriver 4660 includes a proximal handle portion 4662 (illustrated in dashed line), an elongated body portion 4664, and a distal tool portion 4666.

The distal tool portion 4666, as illustrated in greater detail in FIG. 88 includes a substantially hexagonal outer periphery which is received in the substantially hexagonal recess 4628 in the joint portion 4614 of the screw member 4602. A spring member at the distal tool portion 4666 releasably engages the hexagonal recess 4628 of the screw member 4602 to support the fastener 4600 during insertion and tightening. In the exemplary embodiment, a spring member 4672 is configured to engage the side wall of the recess 4628. More particularly, a channel/groove is provided in the tip portion 4666 for receiving the spring member 4672. The channel/groove includes a medial longitudinal notch portion 4676, a proximal, angled channel portion 4678, and a distal substantially transverse channel portion 4680. The spring member 4672 is preferably manufactured from stainless steel and has a medial portion 4682 which is partially received in the longitudinal notch portion 4676, an angled proximal portion 4684 which is fixedly received in the angled channel portion 4678, and a transverse distal portion 4686 which is slidably received in the transverse channel 4680. The medial portion 4682 of the spring member 4672 is partially exposed from the distal tip portion 4666 and normally biased in a transverse outward direction with respect to the longitudinal axis (indicated by arrow E), in order to supply bearing force against the wall of the recess 4628. Alternatively, the distal tip portion of the screw driver may be magnetized in order to hold the screw portion 4602. Similarly, the distal tip portion may include a ball bearing or similar member which is normally biased in a radially outward direction to engage the interior wall of the recess 4628 to secure the fastener 4600 to the screwdriver distal tip 4666.

The insertion of the fastener 4600 into the prepared hole 4092 may be achieved by insertion of screwdriver 4660 into conduit 1020 (indicated by arrow G). This procedure may be visualized by the use of the endoscope 1500 in conjunction with fluoroscopy. The screw portion 4602 is threaded into the prepared hole 4092 by the endoscopic screwdriver 4660 (indicated by arrow H). The endoscopic screwdriver 4660 is subsequently separated from the screw, by applying a force in the proximal direction, and thereby releasing the distal tip portion 4666 from the hexagonal recess 4628 (e.g., causing the transverse distal portion 4686 of the spring member 4672 to slide within the transverse recess 4680 against the bias, indicated by arrow F), and removing the screwdriver 4660 from the expandable conduit 1020. An alternative method may use a guide wire, which is fixed in the hole 4092, and a cannulated screw which has an internal lumen (as is known in the art) and is guided over the guide wire into the hole 4092. The screwdriver would be cannulated as well to fit over the guide wire.

For a two-level fixation, it may be necessary to prepare several holes and attach several fasteners 4600. Typically, the expandable conduit will be sized in order to provide simultaneous access to all vertebrae in which the surgical procedure is being performed. In some cases, however, additional enlargement or repositioning of the distal portion of the expandable conduit may be required in order to have sufficient access to the outer vertebrae, e.g., the L4 and S1 vertebrae. In the exemplary embodiment, the expander apparatus 1200 may be repeatedly inserted into the expandable conduit 1020 and expanded in order to further open or position the skirt portion 1024. In the exemplary procedure, additional fasteners are inserted in the L4 and S1 vertebrae in a similar fashion as the fastener 4600 inserted in to the L5 vertebra as described above. (When discussed individually or collectively, a fastener and/or its individual components will be referred to by the reference number, e.g., fastener 4600, housing 4604, and all fasteners 4600. However, when several fasteners and/or their components are discussed in relation to one another, an alphabetic subscript will be used, e.g., fastener 4600a is moved towards fastener 4600b.)

In a further stage of the procedure, the housing portions 4604 of the fasteners 4600 are substantially aligned such that their upright portions 4630 and 4631 face upward, and the notches 4632 are substantially aligned to receive the fixation element or elongated member 4650 therein. The frictional mounting of the housing 4604 to the screw member 4602, described above, allows the housing 4604 to be temporarily positioned until a subsequent tightening step, described below. Positioning of the housing portions 4604 may be performed by the use of an elongated surgical instrument capable of contacting and moving the housing portion to the desired orientation. An exemplary instrument for positioning the housings 4604 is a grasper apparatus 4700, illustrated in FIG. 89. The grasper apparatus 4700 includes a proximal handle portion 4702, an elongated body portion 4704, and distal nose portion 4706. The distal nose portion 4706 includes a pair of grasping jaws 4708a and 4708b, which are pivotable about pin 4710 by actuation of the proximal handle portion 4702. The grasping jaws 4708a and 4708b are illustrated in the closed position in FIG. 89. As is known in the art, pivoting the movable handle 4714 towards stationary handle 4712 causes longitudinal movement of actuator 4716, which in turn pivots the jaw 4708b towards an open position (illustrated in dashed line). The biasing members 4718 and 4720 are provided to return the handles 4712 and 4714 to the open position and bias the jaws 4708a and 4708b to the closed position.

A subsequent stage in the process is the insertion of the fixation element or elongated member 4650 into the expandable conduit 1020. The elongated member is manufactured from a biocompatible material and must be sufficiently strong to maintain the positioning of the vertebrae, or other body structures. In the exemplary embodiment, the elongated members 4650 are manufactured from Titanium 6/4 or titanium alloy. Alternatively, the elongated member may be manufactured from stainless steel or other suitable material. The radii and length of the elongated members 4650 are selected by the physician to provide the best fit for the positioning of the screw heads. Such selection may be performed by placing the elongated member 4650 on the skin of the patient overlying the location of the fasteners and viewed fluoroscopically. For example, a 70 mm preformed rod having a 3.5 bend radius may be selected for the spinal fixation.

Figure 89:
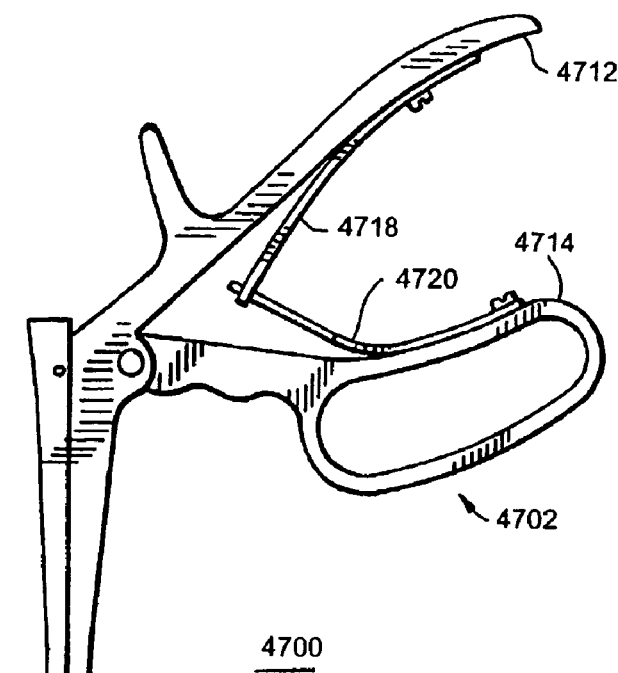
FIG. 89 is side view of a surgical instrument according to another embodiment.

The elongated member 4650 is subsequently fixed to each of the fasteners 4600, and more particularly, to the housings 4604 of each fastener. The grasper apparatus 4700, described above, is also particularly useful for inserting the elongated member 4650 into the expandable conduit 1020 and positioning it with respect to each housing 4604. As illustrated in FIG. 89, the jaws 4708a and 4708b of the grasper apparatus 4700 each has a curved contact portion 4722a and 4722b for contacting and holding the outer surface of the elongated member 4650.

Figure 90:
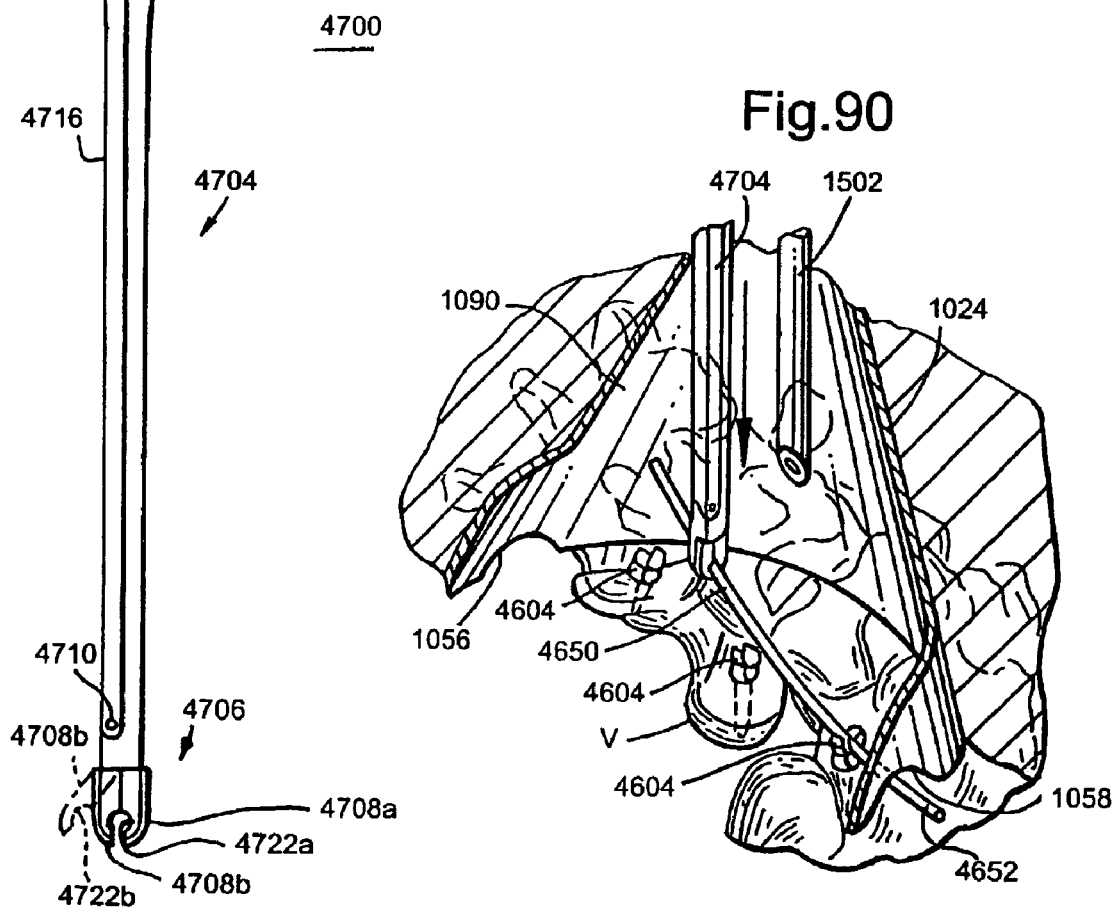
FIG. 90 is a view in partial section of a stage in the procedure according to another embodiment.

As illustrated in FIG. 90, the grasper apparatus 4700 may be used to insert the elongated member 4650 into the operative space 1090 defined at least partially by the skirt portion 1024 of the expandable conduit 1020. The cut-out portions 1056 and 1058 provided in the skirt portion 1024 assist in the process of installing the elongated member 4650 with respect to the housings 4604. The cut-out portions 1056 and 1058 allow an end portion 4652 of the elongated member 4650 to extend beyond the operative space without raising or repositioning the skirt portion 1024. The elongated member 4650 is positioned within the recesses in each housing 4604 defined by grooves 4632 disposed between upright members 4630 and 4631. The elongated member 4650 is positioned in an orientation substantially transverse to the longitudinal axis of each housing 4604.

Figure 91:
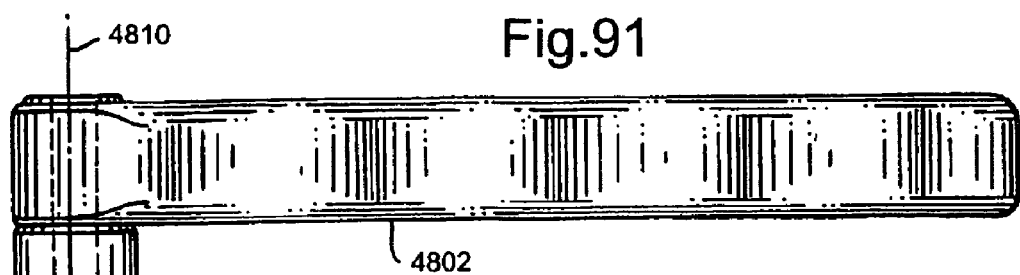
FIG. 91 is a side view of an instrument according to another embodiment.

Further positioning of the elongated member 4650 may be performed by guide apparatus 4800, illustrated in FIG. 91. Guide apparatus 4800 is useful in cooperation with an endoscopic screwdriver, such as endoscopic screwdriver 4660 (illustrated in FIG. 87), in order to position the elongated member 4650, and to introduce and tighten the cap screw 4610, described above and illustrated in FIG. 86. Tightening of the cap screw 4610 with respect to the housing 4604 fixes the orientation of the housing 4604 with respect to the screw portion 4602 and fixes the position of the elongated member 4650 with respect to the housing 4604.

In the exemplary embodiment, the guide apparatus 4800 has a proximal handle portion 4802, an elongated body portion 4804, and a distal tool portion 4806. The elongated body portion 4804 defines a central bore 4808 (illustrated in dashed line) along its longitudinal axis 4810. The central bore 4808 is sized and configured to receive the endoscopic screwdriver 4660 and cap screw 4610 therethrough. In the exemplary embodiment, the diameter of the central bore 4808 of the elongated body portion 4804 is about 0.384-0.388 inches in diameter, and the external diameter of the endoscopic screwdriver 4660 (FIG. 87) is about 0.25 inches.

The proximal handle portion 4802 extends transverse to the longitudinal axis 4810, which allows the physician to adjust the guide apparatus 4800 without interfering with the operation of the screwdriver 4660.

Figure 92:
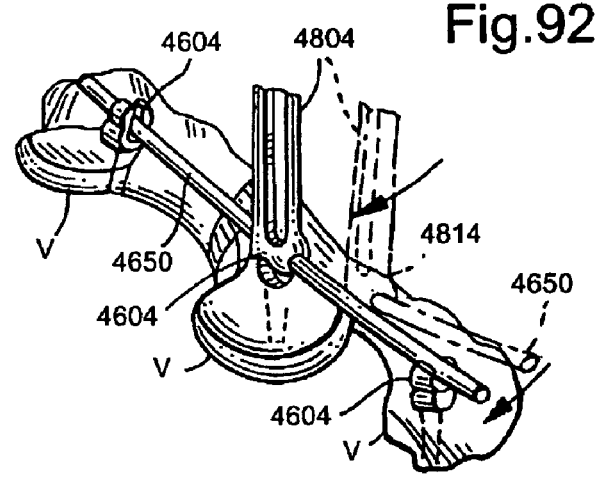
FIG. 92 is a perspective view similar to FIG. 90 illustrating the apparatus of FIGS. 85 and 91, in a further stage of the procedure according to another embodiment.

The distal portion 4806 of the apparatus includes several semicircular cut out portions 4814 which assist in positioning the elongated member 4650. As illustrated in FIG. 92, the cut out portions 4814 are sized and configured to engage the surface of elongated member 4650 and move the elongated member 4650 from an initial location (illustrated in dashed line) to a desired location.

Figure 93:
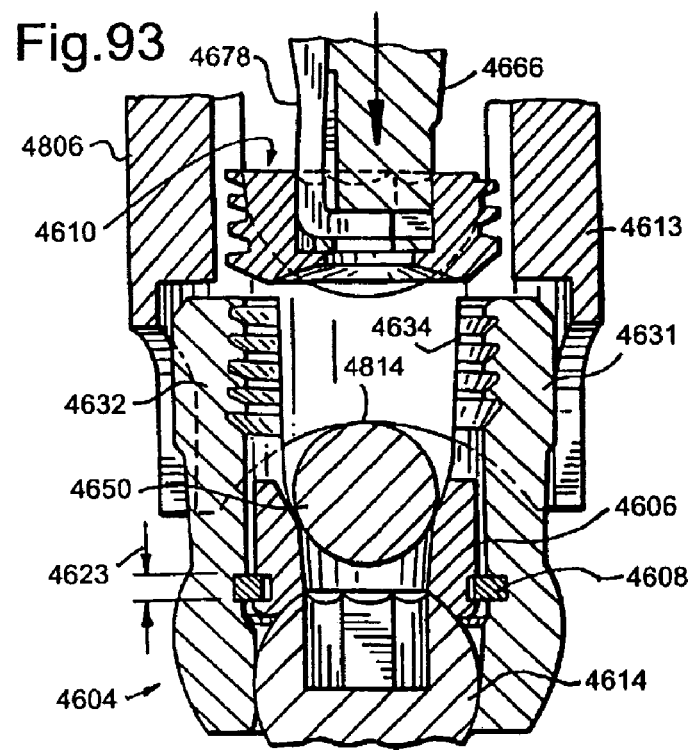
FIG. 93 is an enlarged sectional view of the apparatus of FIGS. 85 and 91, illustrating a still further stage according to another embodiment.

As illustrated in FIG. 93, the guide apparatus 4800 is used in cooperation with the endoscopic screwdriver 4660 to attach the cap screw 4610. The distal end of the body portion 4804 includes a pair of elongated openings 4816, which permit the physician to endoscopically view the cap screw 4610 retained at the distal tip 4666 of the endoscopic screw driver 4660.

The guide apparatus 4800 and the endoscopic screwdriver 4660 may cooperate as follows: The guide apparatus 4800 is configured to be positioned in a surrounding configuration with the screwdriver 4600. In the exemplary embodiment, the body portion 4804 is configured for coaxial placement about the screwdriver 4660 in order to distribute the contact force of the guide apparatus 4800 on the elongated member 4650. The distal portion 4806 of the guide apparatus 4800 may bear down on the elongated member 4650 to seat the elongated member 4650 in the notches 4632 in the housing 4604. The "distributed" force of the guide apparatus 4800 may contact the elongated member 4650 on at least one or more locations. In addition, the diameter of central bore 4808 is selected to be marginally larger than the exterior diameter of cap screw 4610, such that the cap screw 4610 may freely slide down the central bore 4808, while maintaining the orientation shown in FIG. 93. This configuration allows the physician to have effective control of the placement of the cap screw 4610 into the housing 4604. The cap screw 4610 is releasably attached to the endoscopic screwdriver 4660 by means of spring member 4672 engaged to the interior wall of hexagonal recess 4611 as it is inserted within the bore 4808 of the body portion 4804 of guide apparatus 4800. The cap screw 4610 is attached to the housing 4604 by engaging the threads 4615 of the cap screw 4610 with the threads 4634 of the housing.

Figure 94:
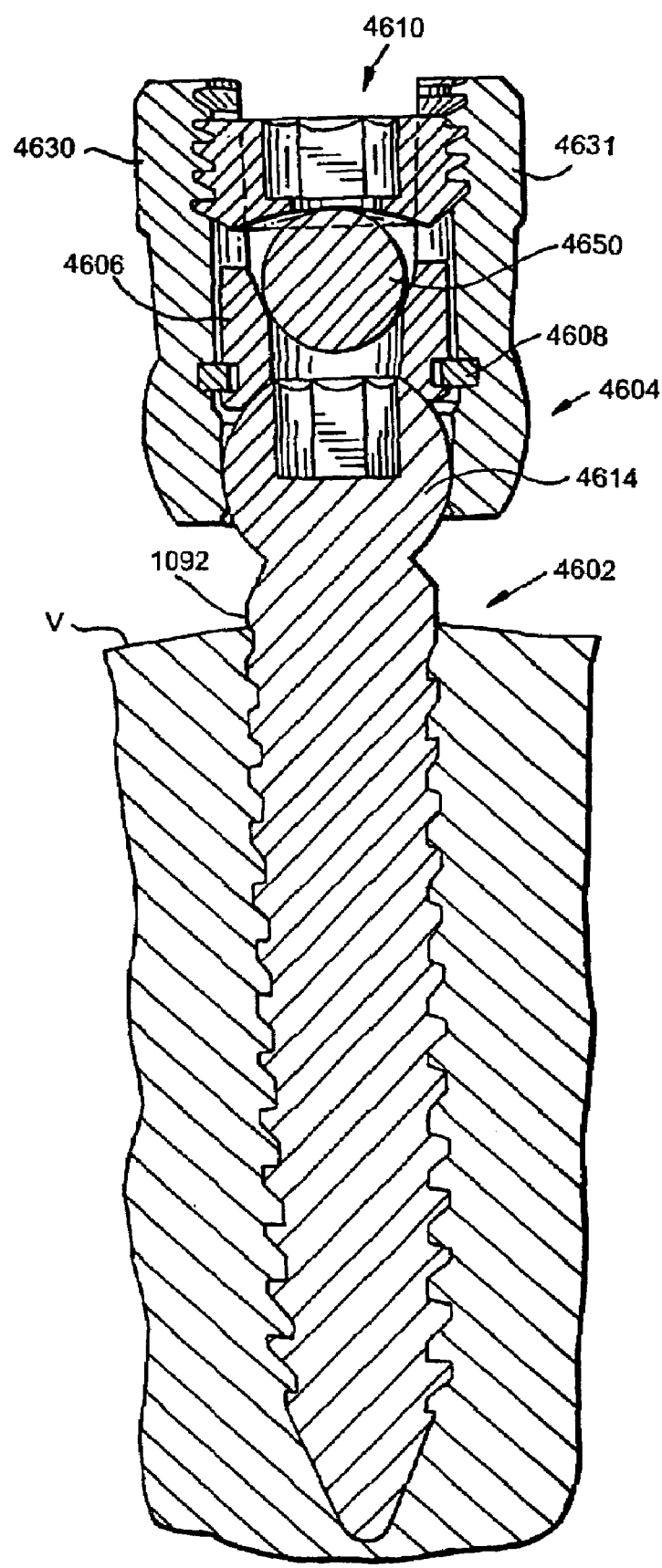
FIG. 94 is an enlarged sectional view similar to FIG. 93, illustrating a subsequent stage of the procedure according to another embodiment.

As illustrated in FIG. 94, tightening of the cap screw 4610 fixes the assembly of the housing 4604 with respect to the elongated member 4650. In particular, the distal surface of the cap screw 4610 provides a distal force against the elongated member 4650, which in turn drives the spacer member 4606 against the joint portion 4614 of the screw portion 4602, which is consequently fixed with respect to the housing 4604.

If locations of the vertebrae are considered acceptable by the physician, then the fixation procedure is substantially complete once the cap screws 4610 have been attached to the respective housings 4604, and tightened to provide a fixed structure as between the elongated member 4650 and the various fasteners 4600. However, if compression or distraction of the vertebrae with respect to one another is required additional apparatus would be used to shift the vertebrae prior to final tightening of all the cap screws 4610.

In the exemplary embodiment, this step is performed with a surgical instrument, such as compressor-distracter instrument 4900, illustrated in FIG. 95, which is useful to relatively position bone structures in the cephalad-caudal direction and to fix their position with respect to one another. Thus, the compressor-distracter instrument 4900 has the capability to engage two fasteners 4600 and to space them apart while simultaneously tightening one of the fasteners to fix the spacing between the two vertebrae, or other bone structures. Moreover, the compressor-distracter instrument 4900 may also be used to move two fasteners 4600, and the vertebrae attached thereto into closer approximation and fix the spacing there between.

The distal tool portion 4902 of the compressor-distracter instrument 4900 is illustrated in FIG. 95. (Further details of the compressor-distracter apparatus is described in co-pending U.S. application Ser. No. 10/178,875, filed Jun. 24, 2002, entitled "Surgical Instrument for Moving Vertebrae," which is hereby incorporated by reference in its entirety herein.) The distal tool portion 4902 includes a driver portion 4904 and a spacing member 4906. The driver portion 4904 has a distal end portion 4908 with a plurality of wrenching flats configured to engage the recess 4611 in the proximal face of the cap screw 4610, and to apply torque to the cap screw. The driver portion 4904 is rotatable about the longitudinal axis (indicated by arrow M) to rotate the cap screw 4610 relative to the fastener 4600. Accordingly, the driver portion 4904 can be rotated to loosen the cap screw 4610 on the fastener 4600 and permit movement of the elongated member 4650 connected with one of the vertebrae relative to the fastener 4600 connected with another of the vertebrae. The cap screw 4610 can also be rotated in order to tighten the cap screw 4610 and clamp the elongated member 4650 to the fastener 4600.

The distal tool portion 4902 may also include a spacing member, such as spacing member 4906, which engages an adjacent fastener 4600*b* while driver member 4904 is engaged with housing 4600*a* to move the fastener 4600*b* with respect to fastener 4600*a*. In the exemplary embodiment, spacing member 4906 is a jaw portion which is pivotably mounted to move between a first position adjacent the driver portion and a second position spaced from the driver portion, as shown in FIG. 95. The distal tip 4910 of the spacing member 4906 is movable relative to the driver portion 4904 in a direction extending transverse to the longitudinal axis.

As illustrated in FIG. 95, the spacer member 4906 can be opened with respect to the driver portion 4904 to space the vertebrae further apart (as indicated by arrow N). The distal portion 4910 of the spacer member 4906 engages the housing 4604*b* of fastener 4600*b* and moves fastener 4600*b* further apart from fastener 4600*a* to distract the vertebrae. Where the vertebrae are to be moved closer together, e.g. compressed, the spacer member 4906 is closed with respect to the driver portion 4904 (arrow P), as illustrated in FIG. 96. The distal portion 4610 of spacer member 4606 engages housing 4604*b* of fastener 4600*b* and moves fastener 4600*b* towards fastener 4600*a*. When the spacing of the vertebrae is acceptable to the physician, the cap screw 4610*a* is tightened by the driver member 4904, thereby fixing the relationship of the housing 4604*a* with respect to elongated member 4650, and thereby fixing the position of the vertebrae, or other bone structures, with respect to one another.

Once the elongated member or fixing element 4650 is fixed with respect to the fasteners 4600, the procedure is substantially complete. The surgical instrumentation, such as the endoscope 1500 is withdrawn from the surgical site. The expandable conduit 1020 is also withdrawn from the site. The muscle and fascia typically close as the expandable conduit 1020 is withdrawn through the dilated tissues in the reduced profile configuration. The fascia and skin incisions are closed in the typical manner, with sutures, etc. The procedure described above may be repeated for the other lateral side of the same vertebrae, if indicated.

Accordingly, the method of fixing three vertebrae V of a patient together at the surgical site includes inserting a first cannula 1020 into the body of the patient. The skirt portion 1024 of the cannula 1020 is expanded using the expander apparatus 1200. A first fusion device 2010 or 2110 is moved through the cannula 1020 and inserted between the first and second vertebrae V. A first fastener 4600 is moved through the cannula 1020 and secured to the first vertebra V. A second fastener 4600 is moved through the cannula 1020 and secured to a second vertebra V. A second fusion device 2010 or 2110 is moved through the cannula 1020 and inserted between the second and third vertebrae V. A third fastener 4600 is moved through the cannula 1020 and secured to the third vertebra V. A first fixation element 4650 is moved through the cannula 1020. The first fixation element 4650 is fixed to the first, second, and third fasteners 4600.

A second cannula 1020 is inserted into the body of the patient laterally from where the first cannula was inserted. The skirt portion 1024 of the second cannula 1020 is expanded using the expander apparatus 1200. A third fusion device 2010 or 2110 is moved through the cannula 1020 and inserted between the first and second vertebrae V. A fourth fastener 4600 is moved through the second cannula 1020 and secured to the first vertebra V. A fifth fastener 4600 is moved through the cannula 1020 and secured to the second vertebra V. A fourth fusion device 2010 or 2110 is moved through the second cannula 1020 and inserted between the second and third vertebrae V. A sixth fastener 4600 is moved through the second cannula 1020 and secured to the third vertebra V. A second fixation element 4650 is moved through the second cannula 1020. The second fixation element 4650 is fixed to the fourth, fifth, and sixth fasteners.

Although the method of securing the three vertebrae together is described as including the insertion of fusion devices between the second and third vertebrae, it is contemplated that fusion devices may only be inserted between the first and second vertebrae. Furthermore, it is contemplated that the skirt portion 1024 of the cannula 1020 could include a stop that retains the skirt portion in an expanded configuration as shown in U.S. patent application Ser. No. 09/855,358, now U.S. Pat. No. 6,524,320, which is hereby incorporated by reference in its entirety herein.

Figure 97:
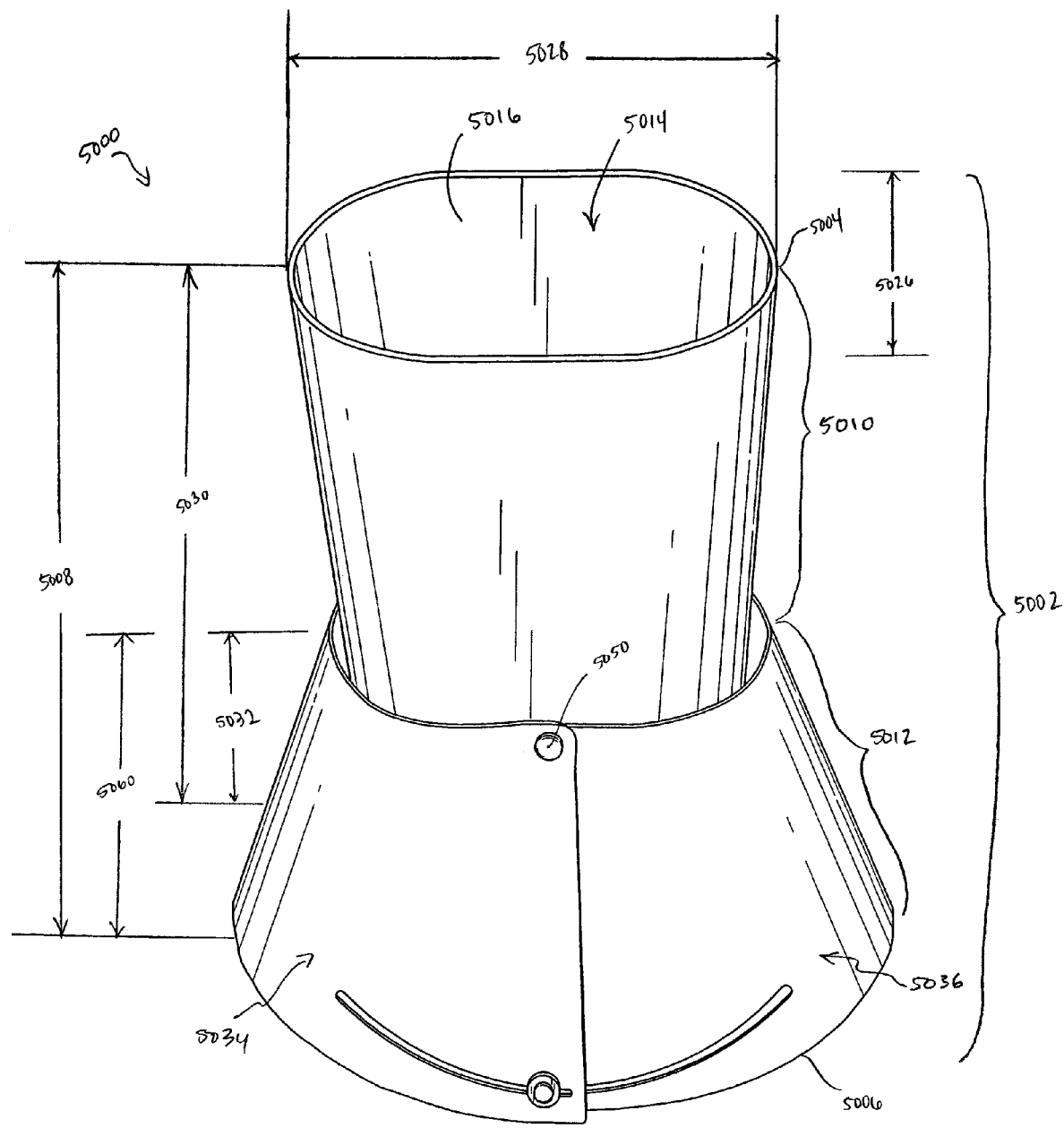
FIG. 97 is a perspective view of an access device according to another embodiment.
Figure 98:
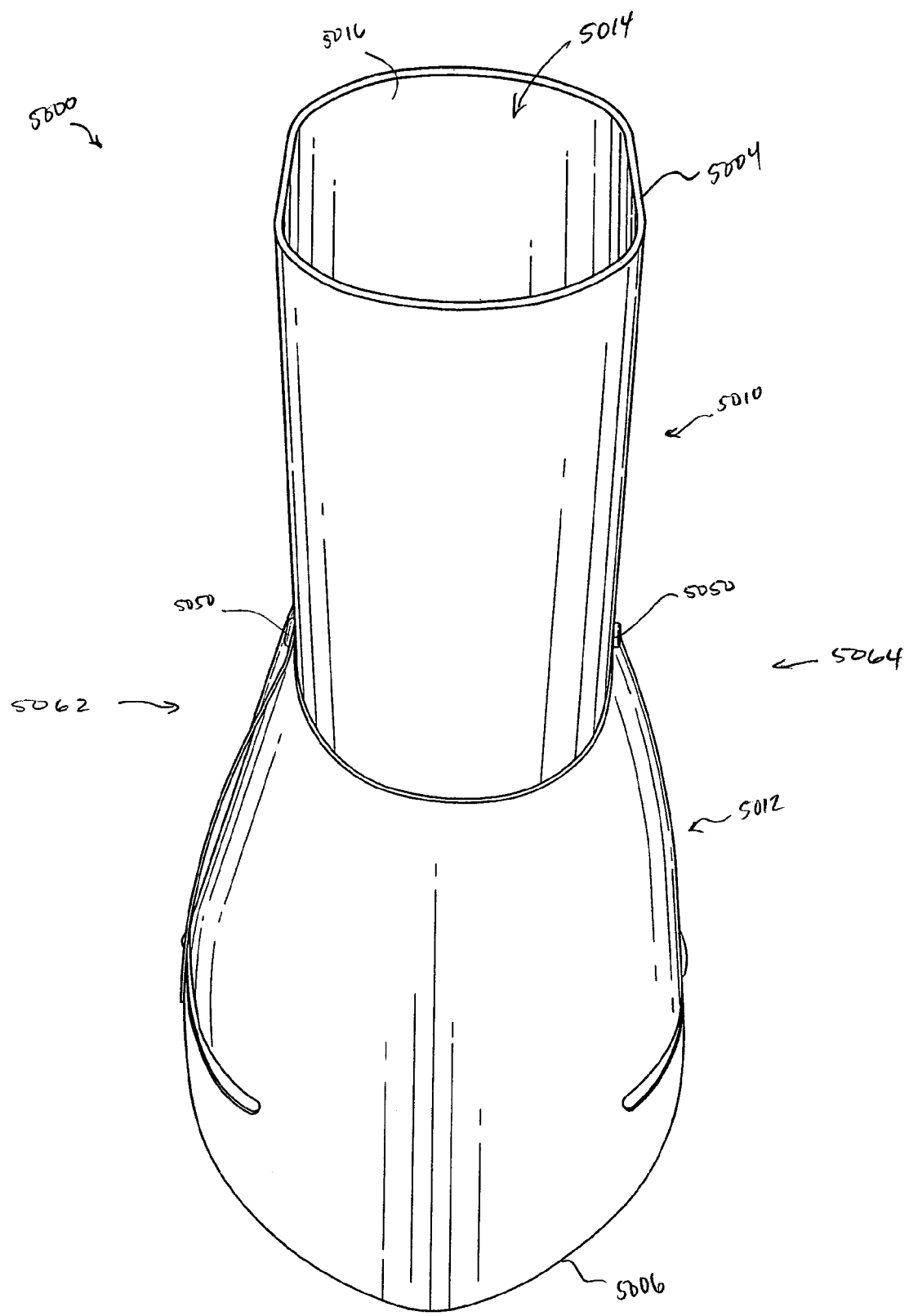
FIG. 98 is a side perspective view of the access device of FIG. 97.

FIGS. 97-103 illustrate various embodiments of another access device designated by reference number 5000. The term "access device" is used in its ordinary sense to mean a device that can provide access and is a broad term and it includes structures having an elongated dimension and defining a passage, e.g., a cannula or a conduit. With reference to FIGS. 97 and 98, the access device 5000 is configured to be inserted through the skin of the patient to provide access during a surgical procedure to a surgical location within a patient, e.g., a spinal location. The term "surgical location" is used in its ordinary sense (i.e. a location where a surgical procedure is performed) and is a broad term and it includes locations subject to or affected by a surgery. The term "spinal location" is used in its ordinary sense (i.e. a location at or near a spine) and is a broad term and it includes locations adjacent to or associated with a spine that may be sites for surgical spinal procedures. The access device 5000 also can retract tissue to provide greater access to the surgical location.

The access device 5000 has an elongate body 5002 that has a proximal end 5004 and a distal end 5006. With reference to FIGS. 97 and 98, the elongate body 5002 has a length 5008 between the proximal end 5004 and the distal end 5006. The length 5008 is selected such that when the access device 5000 is applied to a patient during a surgical procedure, the distal end 5006 can be positioned inside the patient adjacent the spinal location. When so applied, the proximal end 5004 is preferably outside the patient at a suitable height, as discussed more fully below.

In one embodiment, the elongate body 5002 comprises a proximal portion 5010 and a distal portion 5012. The proximal portion 5010 has an oblong or generally oval shaped cross section in one embodiment. The term "oblong" is used in its ordinary sense (i.e., having an elongated form) and is a broad term and it includes a structure having a dimension, especially one of two perpendicular dimensions, such as, for example, width or length, that is greater than another and includes shapes such as rectangles, ovals, elipses, triangle, diamonds, trapezoids, parabolas, and other elongated shapes having straight or curved sides. The term "oval" is used in its ordinary sense (i.e., egg like or eliptical) and is a broad term and includes oblong shapes having curved portions.

The distal portion 5012 is expandable in one embodiment. At least one passage 5014 extends through the elongate body 5002 between the proximal end 5004 and the distal end 5006, e.g., through the proximal and distal portions 5010, 5012. The passage 5014 preferably is defined by a smooth metal inner surface 5016 that extends substantially entirely around the perimeter of the passage 5014 between the proximal and distal ends 5004, 5006 in one embodiment. The inner surfaces 5016 can take other forms, e.g., employing other materials, different smoothness, and/or varying degrees of smoothness.

Figure 101:
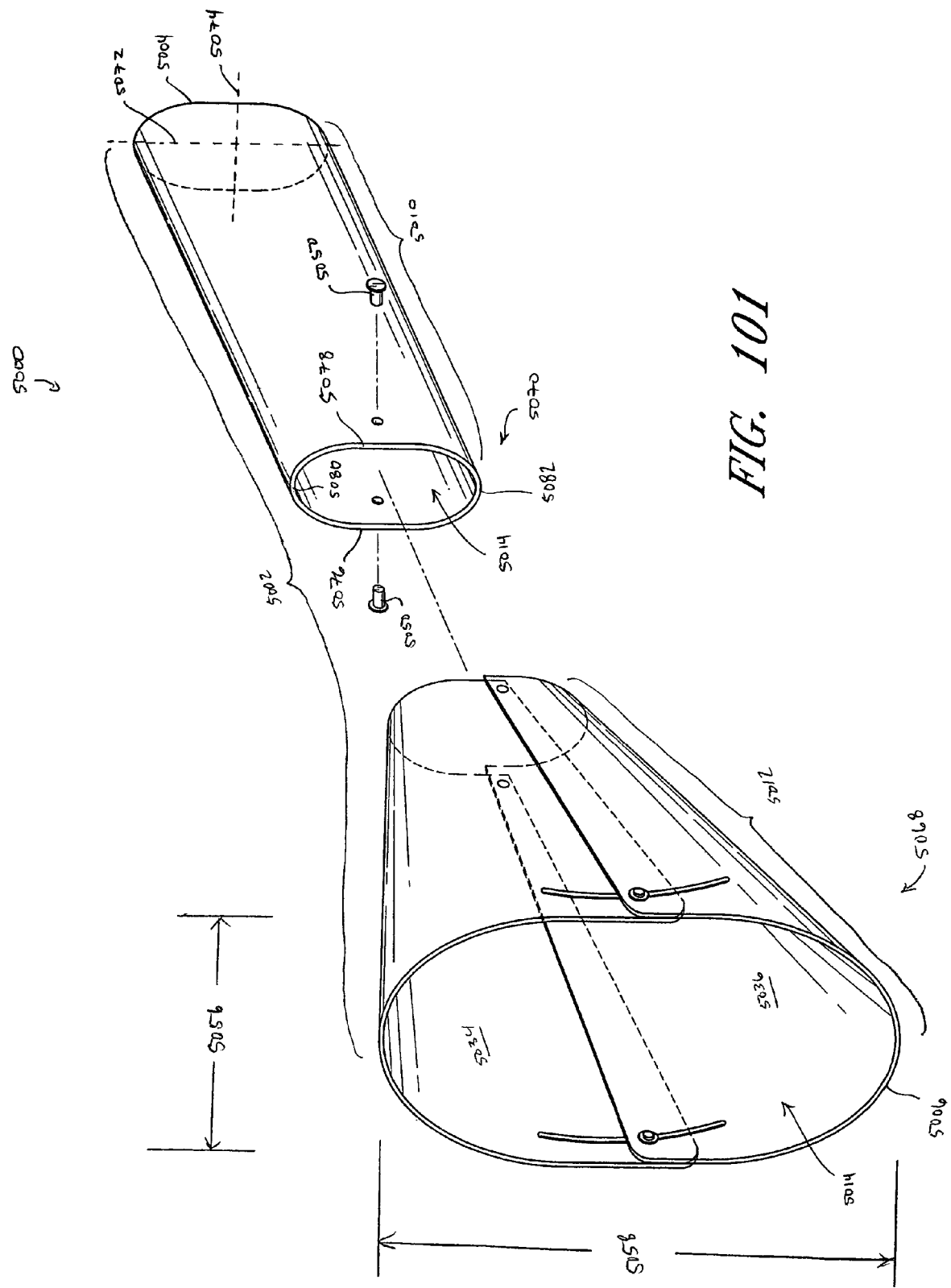
FIG. 101 is an exploded perspective view of the access device of FIG. 97 in an expanded configuration with some portions shown in hidden line.
Figure 102:
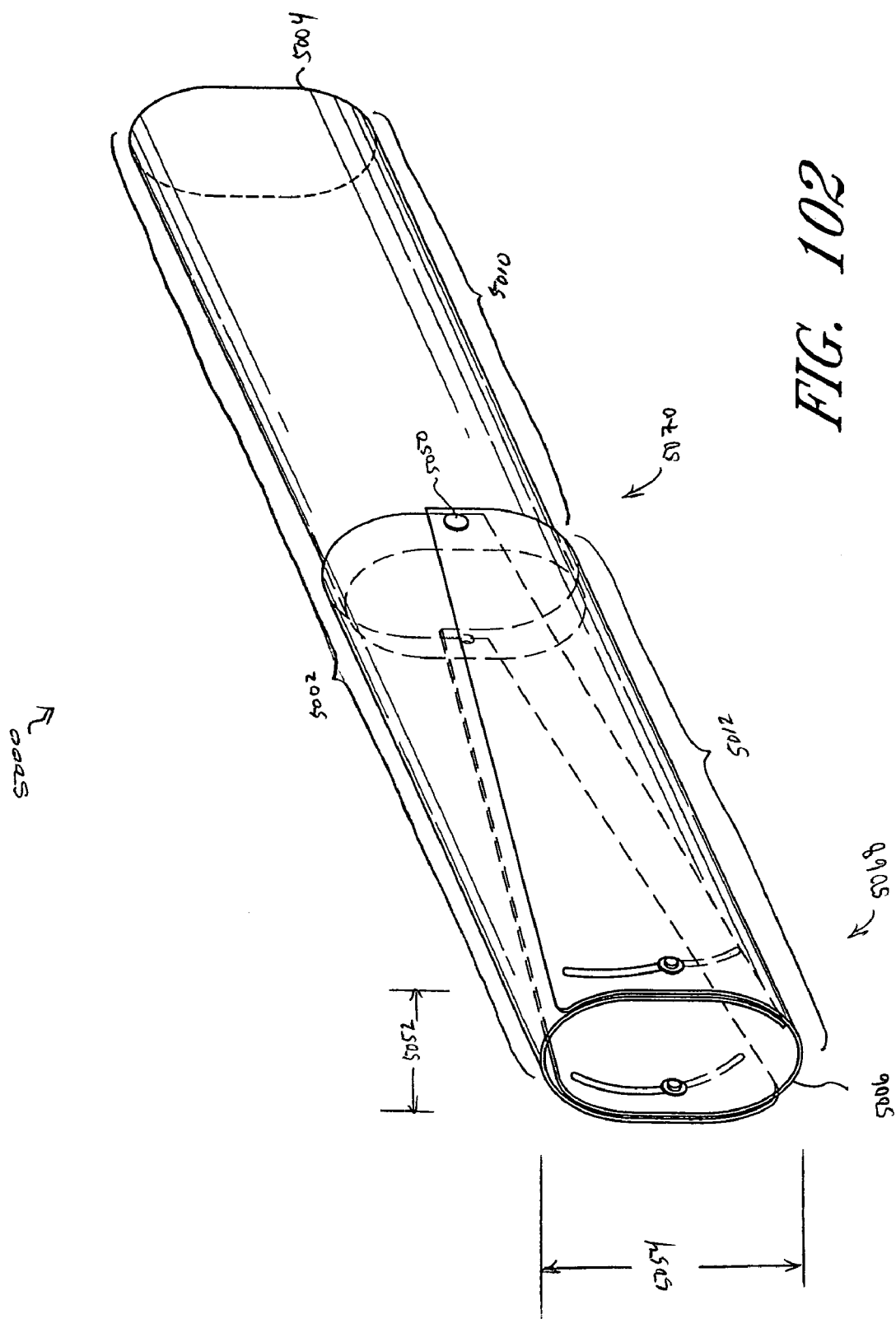
FIG. 102 is a perspective view of the access device of FIG. 97 in a contracted configuration with some portions shown in hidden line.

In one embodiment, the elongate body 5002 is expandable from a first configuration, shown in FIG. 102, to a second configuration, shown in FIG. 101. In one embodiment, the elongate body 5002 is movable from the first configuration to the second configuration when inserted within the patient, as discussed above. In the first configuration, the access device 5000 is configured, e.g., sized, for insertion into the patient. As discussed more fully below, in one embodiment, the first configuration of the access device 5000 provides that the passage 5014 has a relatively small transverse cross-sectional area at the distal end 5006, e.g., a cross-sectional area about equal to the cross-sectional area of the proximal end 5004, or less.

In the second configuration, the cross-sectional area of the passage 5014 at the distal end 5006 is greater than the cross-sectional area of the passage 5014 at the proximal end 5004 in one embodiment. The second configuration is particularly well suited for performing surgical procedures in the vicinity of a spinal location. Other configurations and arrangements of the access device 5000 are discussed herein below.

As shown in FIGS. 97 and 98, in one embodiment, the proximal portion 5010 and the distal portion 5012 are discrete, i.e., separate members. In other embodiments, the proximal and distal portions 5010, 5012 are a unitary member. In the illustrated embodiment, the proximal portion 5010 comprises an oblong, generally oval shaped cross section over the elongated portion. It will be apparent to those of skill in the art that the cross section can be of any suitable oblong shape. The proximal portion 5010 can be any desired size. The proximal portion 5010 can have a cross-sectional area that varies from one end of the proximal portion 5010 to another end. For example, the cross-sectional area of the proximal portion 5010 can increase or decrease along the length of the proximal portion 5010. Preferably, the proximal portion 5010 is sized to provide sufficient space for inserting multiple surgical instruments through the elongate body 5002 to the surgical location.

Figure 100:
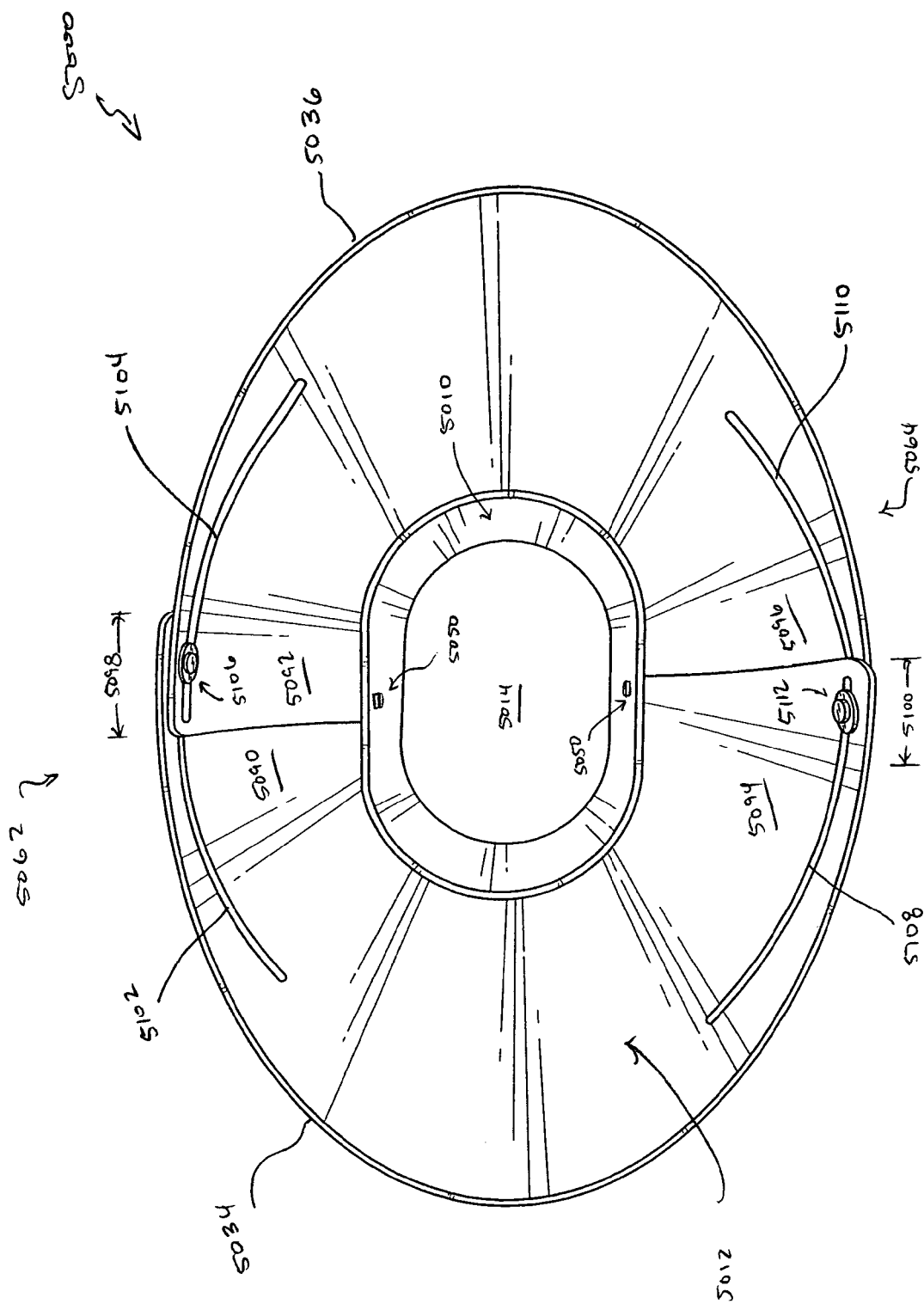
FIG. 100 is an end view of the access device of FIG. 97.

As shown in FIG. 97, the generally oval shaped cross section of the proximal portion 5010 in one embodiment has a first dimension 5026 of about 24 mm and a second dimension 5028 of about 35 mm. The first and second dimensions 5026, 5028 could range from at least about 10 mm up to about 70 mm or more. The proximal portion 5010 in one embodiment has a third dimension 5030 of about 50 mm, but the third dimension 5030 could range from about 10 mm up to about 180 mm or more. In one embodiment, the proximal portion 5010 extends distally at least partially into the distal portion 5012 of the device 5000, as shown in FIG. 100. In FIG. 97, the proximal portion 5010 extends a distance 5032 of about 10 mm into the distal portion 5012. The proximal portion 5010 can extend a distance 5032 of between about 5 mm and about 20 mm into the distal portion 5012 in some embodiments. The exposed portion of the proximal portion 5010 (i.e., the portion thereof that extends proximally of the distal portion 5012) can be of any suitable height. Additionally, the distance 5032 that the proximal portion 5010 extends into the distal portion 5012 can be increased or decreased, as desired.

As shown in FIGS. 97 and 98, the proximal portion 5010 is coupled with the distal portion 5012, e.g., with one or more couplers 5050. Preferably the proximal and distal portions 5010, 5012 are coupled on a first lateral side 5062 and on a second lateral side 5064 with the couplers 5050. When applied to a patient in a posterolateral procedure, either of the first or second lateral sides 5062, 5064 can be a medial side of the access device 5000, i.e., can be the side nearest to the patient's spine. Couplers 5050 can be any suitable coupling devices, such as, for example, rivet attachments. In one embodiment, the couplers 5050 are located on a central transverse plane of the access device 5000.

Figure 99:
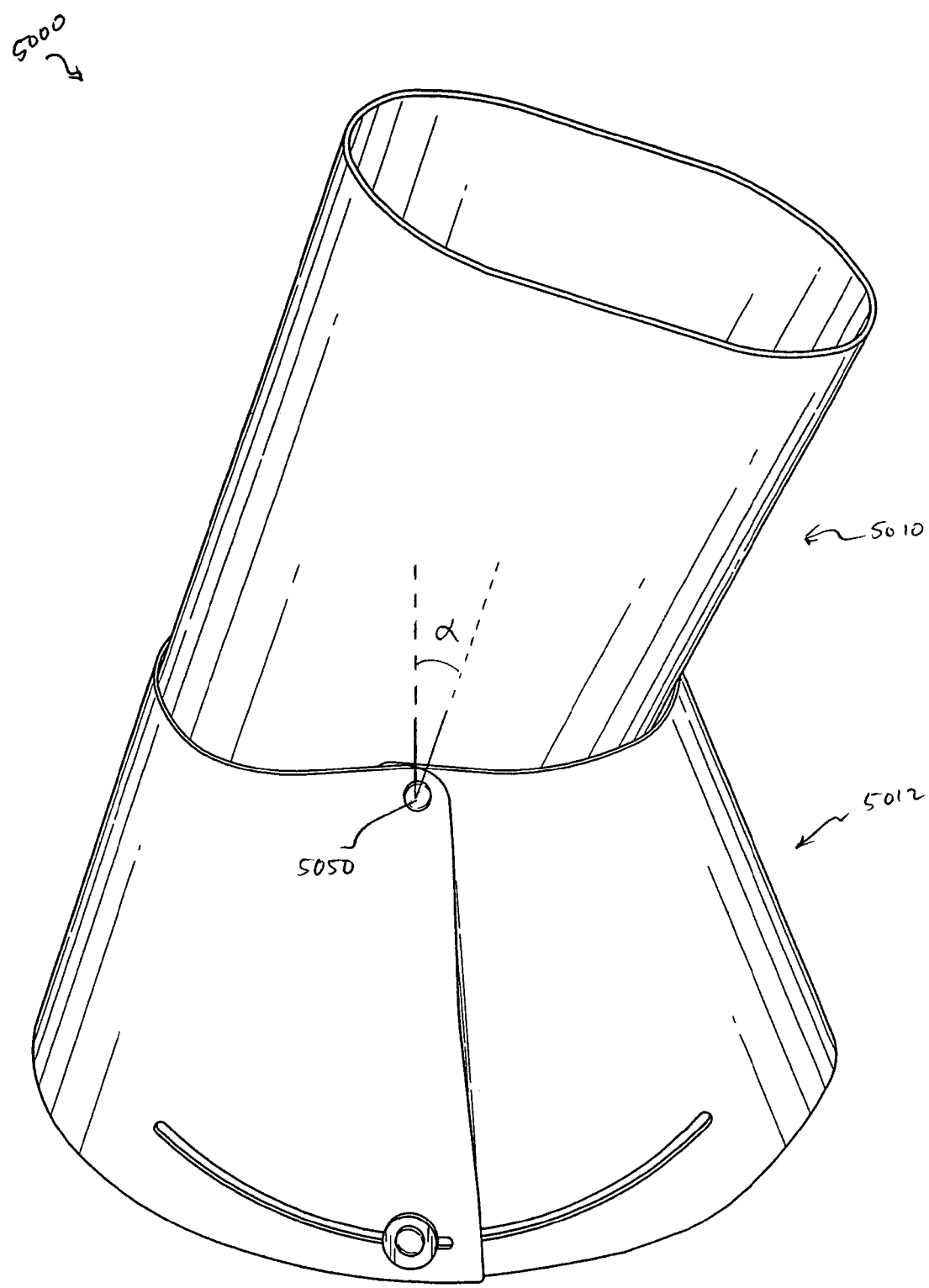
FIG. 99 is a perspective view of the access device of FIG. 97 in a pivoted configuration.

The couplers 5050 preferably allow for rotation and pivotal movement of the proximal portion 5010 relative the distal portion 5012. A portion of the range of rotation and pivotal movement of the proximal portion 5010 relative the distal portion 5012 can be seen by comparing the position of the proximal portion 5010 in FIG. 97 to the position thereof in FIG. 99. In FIG. 99, the proximal portion 5010 is seen at an angle $\alpha$ of about 20 degrees with respect to a transverse plane extending vertically through the couplers. One skilled in the art will appreciate that rotating or pivoting the proximal portion 5010 to the angle $\alpha$ permits enhanced visualization of and access to a different portion of the spinal location accessible through the access device 5000 than would be visualized and accessible at a different angle. Depending on the size of the distal portion 5012, the angle $\alpha$ can be greater than, or less than, 20 degrees. Preferably, the angle $\alpha$ is between about 10 and about 40 degrees.

The pivotable proximal portion 5010 allows for better access to the surgical location and increased control of surgical instruments. Additionally, the generally oval shape of the proximal portion 5010 has increased the cross-sectional area available for a variety of procedures, some of which may require or benefit from more proximal end exposure. Embodiments having a generally oval shape can also be employed advantageously in procedures such as the lateral or postero-lateral placement of artificial disks, as well as other developing procedures.

As discussed above, the distal portion 5012 is expandable in one embodiment. As shown in FIG. 100, the degree of expansion of the distal portion 5012 is determined by an amount of overlap between a first skirt member 5034 and a second skirt member 5036 in one embodiment. In particular, the first skirt member 5034 has a first overlapping portion 5090 on the first lateral side 5062 and the second skirt member 5036 has a second overlapping portion 5092 on the first lateral side 5062. The first skirt member 5034 has a third overlapping portion 5094 on the second lateral side 5064 and the second skirt member 5036 has a fourth overlapping portion 5096 on the second lateral side 5064. The first and second overlapping portions 5090, 5092 overlap to define a first overlap area 5098. The third and fourth overlapping portions 5094, 5096 overlap to define a second overlap area 5100. The extents of the first and second overlap areas 5098, 5100 preferably are reduced when the distal portion 5012 is in the second configuration. The extents of the first and second overlap areas 5098, 5100 preferably are increased when the distal portion 5012 is in the first configuration.

The distal portion 5012 preferably is manufactured from a rigid material, such as stainless steel. The distal portion 5012 of the access device 5000 can be manufactured from a sheet of stainless steel having a thickness of between about 0.003-0.010 inches. In some embodiments, the thickness is about 0.007 inches. Other materials, such as Nitinol, plastics, or other suitable materials can also be used.

In some embodiments, the distal portion 5012 can be manufactured so that it normally assumes an expanded configuration. Additionally, the distal portion 5012 can assume an intermediate configuration and corresponding cross-sectional area, which has greater dimensions than the first configuration, and smaller dimensions than the second configuration. Alternatively, an expander apparatus, similar to those previously discussed herein, can be used to expand the distal portion 5012 a suitable amount.

The skirt members 5034, 5036 preferably are slidably coupled together. In one embodiment, the first and second skirt members 5034, 5036 are slidably coupled to each other with at least one guide member disposed in at least one slot defined in each of the skirt members 5034, 5036. In particular, a first slot 5102 is formed in the first overlapping portion 5090 of the first skirt member 5034 and a second slot 5104 is formed in the second overlapping portion 5092 of the second skirt member 5036 on the first lateral side 5062 of the access device 5000. A guide member 5106 extends through the first and second slots 5102, 5104 and is translatable therein. Similarly, a third slot 5108 is formed in the third overlapping portion 5094 of the first skirt member 5034 and a fourth slot 5110 is formed in the fourth overlapping portion 5096 of the second skirt member 5036 on the second lateral side 5064 of the access device 5000. A guide member 5112 extends through the third and fourth slots 5108, 5110 and is translatable therein.

Any suitable mechanism for slidably coupling the skirt members 5034, 5036 can be used. In the illustrated embodiment, two floating rivets are used as guide members 5106, 5112. In another embodiment, one or more of the slots 5102, 5104, 5108, 5110 can include a locking or ratcheting mechanism (not shown). Locking mechanism is used in its ordinary sense (i.e. a mechanism to maintain relative positions of members) and is a broad term and it includes structures' having detent arrangements, notches, and grooves. Some additional examples of locking mechanisms are disclosed in U.S. patent application Ser. No. 10/361,887, filed Feb. 10, 2003, entitled "Structure for Receiving Surgical Instruments," published as application publication No. US2003/0153927 on Aug. 14, 2003, which is hereby incorporated by reference herein in its entirety.

With reference to FIGS. 97-102, as discussed above, the skirt members 5034, 5036 preferably pivot about couplers 5050 joining the proximal portion 5010 with the distal portion 5012. The distal portion 5012 preferably pivots on an axis perpendicular to the longitudinal axis of the access device 5000. This arrangement is particularly useful for providing surgical access to anatomical features generally located and oriented along the Cephalad-Caudal direction.

As discussed above, the access device 5000 can be expanded from the first configuration to the second configuration by way of the movement of the first skirt member 5034 relative to the second skirt member 5036. In the illustrated embodiment, the distal portion 5012 is generally oval shaped both in the first configuration, when the device 5000 is generally contracted, and in the second configuration, when the device 5000 is generally expanded. However, the distal portion 5012 may be configured to transition from a generally circular cross-section distal end (or other convenient shape) in the first configuration to a generally oval cross-section distal end in the second configuration.

As best seen in FIG. 102, the distal portion 5012 preferably has a first dimension 5052 in the first configuration of approximately 24 mm and a second dimension 5054 of approximately 35 mm. As best seen in FIG. 101, the distal portion 5012 preferably has a first dimension 5056 of approximately 45 mm and a second dimension 5058 of approximately 70 mm in the second configuration. Accordingly, in one embodiment in the expanded configuration the distal portion 5012 opens distally to approximately 45 mm by 70 mm. The distal portion 5012 can be arranged to open more or less, as needed or desired. For example, the distal portion 5012 can take on an oval shape wherein the second dimension 5058 is longer than 70 mm, e.g., about 85 mm or more. Alternatively, the distal portion 5012 can have a shape wherein the second dimension 5058 is shorter than 70 mm, e.g., about 45 mm or less. Similarly, in some embodiments the first dimension 5052 can be longer or shorter than 45 mm, e.g., about 35 mm or about 55 mm. As shown in FIG. 97, the distal portion 5012 has a height 5060 that is approximately 45 mm. However, one skilled in the art should recognize that the height 5060 of the distal portion 5012 can be any suitable height. The height 5060 preferably is within the range of about 20 mm to about 150 mm. Access devices having relatively shorter skirt heights 5060 may be advantageous for use with patients having relatively less muscle tissue near the surgical location and generally require smaller incisions. Access devices having relatively longer skirt height 5060 may be advantageous for use with patients having relatively more muscle tissue near the surgical loaction, and may provide greater access.

The distal portion 5012 preferably is sufficiently rigid that it is capable of displacing surrounding tissue as the distal portion 5012 expands. Depending upon the resistance exerted by the surrounding tissue, the distal portion 5012 is sufficiently rigid to provide some resistance against the tissue to remain in the second, expanded configuration. Moreover, the second configuration is at least partially supported by the body tissue of the patient. The displaced tissue tends to provide pressure distally on the distal portion 5012 to at least partially support the access device 5000 in the second configuration. The rigidity of the distal portion 5012 and the greater expansion at the distal end 5006 creates a stable configuration that is at least temporarily stationary in the patient, which at least temporarily frees the physician from the need to actively support the elongate body 5002.

Another advantageous aspect of the access device 5000 is illustrated with reference to FIGS. 101 and 102. In particular, the elongate body 5002 has a first location 5068 and a second location 5070. The first location 5068 is distal of the second location 5070. The elongate body 5002 is capable of having a configuration when inserted within the patient wherein the cross-sectional area of the passage 5014 at the first location 5068 is greater than the cross-sectional area of the passage 5014 at the second location 5070. The passage 5014 is capable of having an oblong shaped cross section between the second location 5070 and the proximal end 5004.

In some embodiments the passage 5014 preferably is capable of having a generally elliptical cross section between the second location 5070 and the proximal end 5004. Additionally, the passage 5014 preferably is capable of having a non-circular cross section between the second location 5070 and the proximal end 5004. Additionally, in some embodiments, the cross section of the passage 5014 can be symmetrical about a first axis 5072 and a second axis 5074, the first axis 5072 being generally normal to the second axis 5074.

As shown in FIG. 101, the configuration of the elongate body 5002 between the first location 5068 and the second location 5070 is generally conical, when the elongate body 5002 is expanded within the patient. The term "conical" is used in its ordinary sense (i.e. a surface formed by line segments joining every point of the boundary of a closed base to a common vertex) and is a broad term and it includes structures having a generally oblong, or oval, cross section, as well as structures having a surface that extends only partially toward a vertex. In some embodiments, the first location 5068 can be near a distal end 5006 of the elongate body 5002, and the second location 5070 can be near a proximal end 5004 of the elongate body 5002.

In the illustrated embodiment, the elongate body 5002 has an oblong shaped cross section near its proximal end 5004 at least when the elongate body 5002 is in the second configuration. In some embodiments, the elongate body 5002 has an oblong shaped cross section along substantially the entire length between the proximal end 5004 and the second location 5070.

Additionally, in some embodiments the passage 5014 can have a generally oval shaped cross section between the second location 5070 and the proximal end 5004. The elongate body preferably has a generally oval shaped cross section at its proximal end 5004 at least when the elongate body 5002 is in the second configuration. The elongate body 5002 can have a generally oval shaped cross section along substantially the entire length between the proximal end 5004 and the second location 5070. The passage 5014 can also have a cross section between the second location 5070 and the proximal end 5004 where the cross section is defined by first and second generally parallel opposing side portions 5076, 5078 and first and second generally arcuate opposing side portions 5080, 5082.

Figure 103:
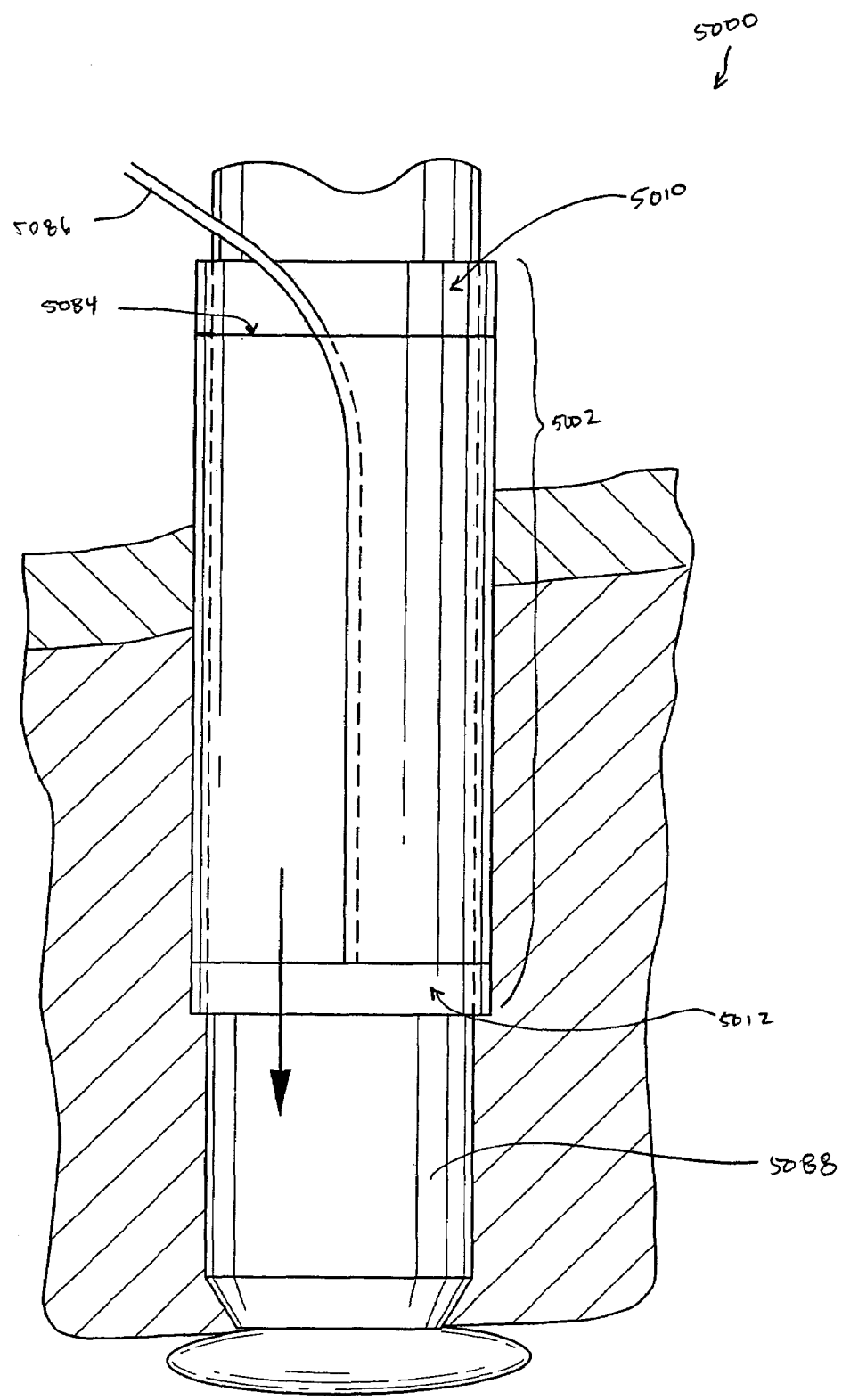
FIG. 103 is a partial sectional view of the access device of FIG. 97 in an early stage of a procedure.

In some embodiments, it is useful to provide a structure to maintain the access device 5000 in an un-expanded state until expansion of the device is desired. As shown in FIG. 103, in one embodiment an outer sleeve 5084, e.g., a plastic sleeve, is provided which surrounds the access device 5000 and maintains the distal portion 5012 in the first configuration. The outer sleeve 5084 can be produced to function as previously described herein with reference to other embodiments. For example, the outer sleeve 5084 can have a braided polyester suture 5086 embedded within it, aligned substantially along the longitudinal axis thereof, such that when the suture 5086 is withdrawn, the sleeve 5084 is torn, which allows the access device 5000 to expand, either resiliently or mechanically, from the first configuration to the second configuration.

In a method for accessing a surgical location within a patient an access device, such as the access device 5000, is provided. As stated above, the elongate body 5002 is capable of having a first configuration sized for insertion into the patient. The elongate body 5002 is capable of having a second configuration when expanded within the patient. In the second configuration, the cross-sectional area of the passage 5014 at a first location 5068 is greater than the cross-sectional area of the passage 5014 at a second location 5070. The first location 5068 is distal to the second location 5070. The passage 5014 is capable of having an oblong shaped cross section between the second location 5070 and the proximal end 5004. The method comprises inserting the access device 5000, in the first configuration, into the patient to the surgical location and expanding the device to the second configuration.

The access device 5000 is inserted to a spinal location in some methods. As shown in FIG. 103, an oblong shaped dilator 5088 preferably is inserted into the patient prior to insertion of the access device 5000. In some applications, the access device 5000 may be inserted laterally to the spinal location. In other applications, the device 5000 is inserted posterolaterally to the spinal location. In some applications, the device 5000 is inserted anteriorly to the spinal location. The device 5000 preferably can be expanded in a cephalad-caudal direction at a spinal location.

With reference to FIG. 103, an early stage in one method involves determining an access point in the skin of the patient to insert the access device 5000. An incision is made at the determined location. In some cases, the incision is approximately 1" to 2" long. A guide wire (not shown) is introduced under fluoroscopic guidance through the incision and past the skin, fascia, and muscle to the approximate surgical site. A series of oblong, or generally oval shaped, dilators is used to sequentially expand the incision to the desired widths, about 24 mm by 35 mm for the illustrated embodiment, without damaging the structure of surrounding tissue and muscles. A first oblong dilator is placed over the guide wire, which expands the opening. The guide wire is then subsequently removed. A second oblong dilator that is slightly larger than the first dilator is placed over the first dilator, which expands the opening further. Once the second dilator is in place, the first dilator is subsequently removed. This process of (1) introducing a next-larger-sized dilator coaxially over the previous dilator and (2) subsequently removing the previous dilator when the next-larger-sized dilator is in place continues until an opening of the desired size is created in the skin, muscle, and subcutaneous tissue. For the illustrated embodiment, these dimensions are about 24 mm by about 35 mm. (Other dimensions for the openings that are useful with some embodiments in connection with spinal surgery range from about 20 mm to about 50 mm, and still other dimensions are contemplated.) In some other embodiments, a series of dilators having circular cross sections are used to partially dilate the opening. Then, a final dilator having a circular inner diameter and an oblong or generally oval shaped outer perimeter can be used to further dilate the opening.

As illustrated in FIG. 103, following placement of the largest oblong, or generally oval shaped dilator 5088, the access device 5000, in the first configuration, is introduced and positioned in a surrounding relationship over the dilator 5088. The dilator 5088 is subsequently removed from the patient, and the access device 5000 is allowed to remain in position.

Once the access device 5000 is positioned in the patient, it can be enlarged to provide a passage 5014 for the insertion of various surgical instrumentation and an enlarged space for performing the procedures described herein. As described above, the elongate body 5002 can accommodate the enlargement in several ways. In the illustrated embodiment, the distal portion 5012 of the device 5000 can be enlarged, and the proximal portion 5010 can maintain an oblong shape. The relative lengths of the proximal portion 5010 and the distal portion 5012 can be adjusted to vary the overall expansion of the access device 5000. Alternatively, in some embodiments expansion can extend along the entire length of the elongate body 5002.

In the illustrated embodiment, the access device 5000 can be expanded by removing the suture 5086 and tearing the sleeve 5084 surrounding the access device 5000, and subsequently expanding the distal portion 5012 mechanically, or allowing the distal portion 5012 to resiliently expand towards the expanded configuration, to create an enlarged surgical space. In some embodiments, the enlarged surgical space extends from the L4 to the S1 vertebrae.

The access device 5000 can be enlarged at its distal portion 5012 using an expander apparatus to create a surgical access space. An expander apparatus useful for enlarging the elongate body 5002 has a reduced profile configuration, and an enlarged configuration. Additionally, the expander apparatus can have an oblong, or generally oval shape. The expander apparatus is inserted into the elongate body 5002 in the reduced profile configuration, and subsequently expanded to the enlarged configuration. The expansion of the expander apparatus also causes the elongate body 5002 to be expanded to the enlarged configuration. In some embodiments, the expander apparatus can increase the cross-sectional area of the elongate body 5002 along substantially its entire length. In other embodiments, the expander apparatus expands only a distal portion 5012 of the elongate body 5002, allowing a proximal portion 5010 to maintain a constant oblong, or generally oval shape. Other expander apparatus are disclosed in U.S. patent application Ser. No. 10/665,754, entitled "Surgical Tool for Use in Expanding a Cannula", filed on Sep. 19, 2003.

In addition to expanding the elongate member 5002, the expander apparatus can also be used to position the distal portion 5012 of the elongate member 5002 at the desired location for the surgical procedure in a manner similar to that described previously with reference to another embodiment.

Once the distal portion 5012 has expanded, the rigidity and resilient characteristics of the distal portion 5012 allow the elongate body 5002 to resist closing to the first configuration and to at least temporarily resist being expelled from the incision. These characteristics create a stable configuration for the elongate body 5002 to remain in position in the body, supported by the surrounding tissue.

The access device 5000, like the other access devices described herein, has a wide variety of applications wherein the passage 5014 provides access to one or more surgical instruments for performing a surgical procedure. In one application, the passage 5014 provides access to perform a two level posterolateral fixation of the spine involving the L4, L5 and S1 vertebrae. The access devices 5000 can be used to deliver a wide variety of fixation elements, including rigid, semi-rigid, or dynamic fixation elements. The access devices are not limited to the posterolateral approach nor to the L4, L5 and S1 vertebrae. The access devices may be applied in other anatomical approaches and with other vertebrae within the cervical, thoracic and lumbar spine. The access devices can be applied in procedures involving one or more vertebral levels and in anterior and lateral procedures.

Further procedures in which the access devices described herein can be applied include procedures involving orthobiologics, bone morphogenetic proteins, and blood concentrators. The access devices can also be used with procedures involving prosthetics, such as disc nucleus replacement, facet joint replacement, or total disc replacement. The access devices can also be applied in procedures involving vertebroplasty, where a crushed vertebrae is brought back to its normal height.

The access devices described herein also can be used in connection with interbody fusion, and fusion of the facets and transverse processes. Some of the fusion procedures that can be performed via the access devices described herein employ allograft struts, bone filling material (e.g., autograft, allograft or synthetic bone filling material), and cages and/or spacers. The cages and the spacers can be made of metal, a polymeric material, a composite material, or any other suitable material. The struts, cages, and spacers are used in the interbody space while the bone filling material can be used both interbody and posterolaterally. Any of the foregoing or other fusion procedures can be used in combination with the orthobiologics and can be performed via the access devices described herein.

Some examples of uses of the access devices described in other procedures and processes, as well as further modifications and assemblies, are disclosed in U.S. Provisional Patent Application No. 60/471,431, filed May 16, 2003, entitled "Access Device For Minimally Invasive Surgery," and in U.S. patent application Ser. No. 10/658,736, filed Sep. 9, 2003 which are hereby incorporated by reference herein in their entireties.

Figure 104:
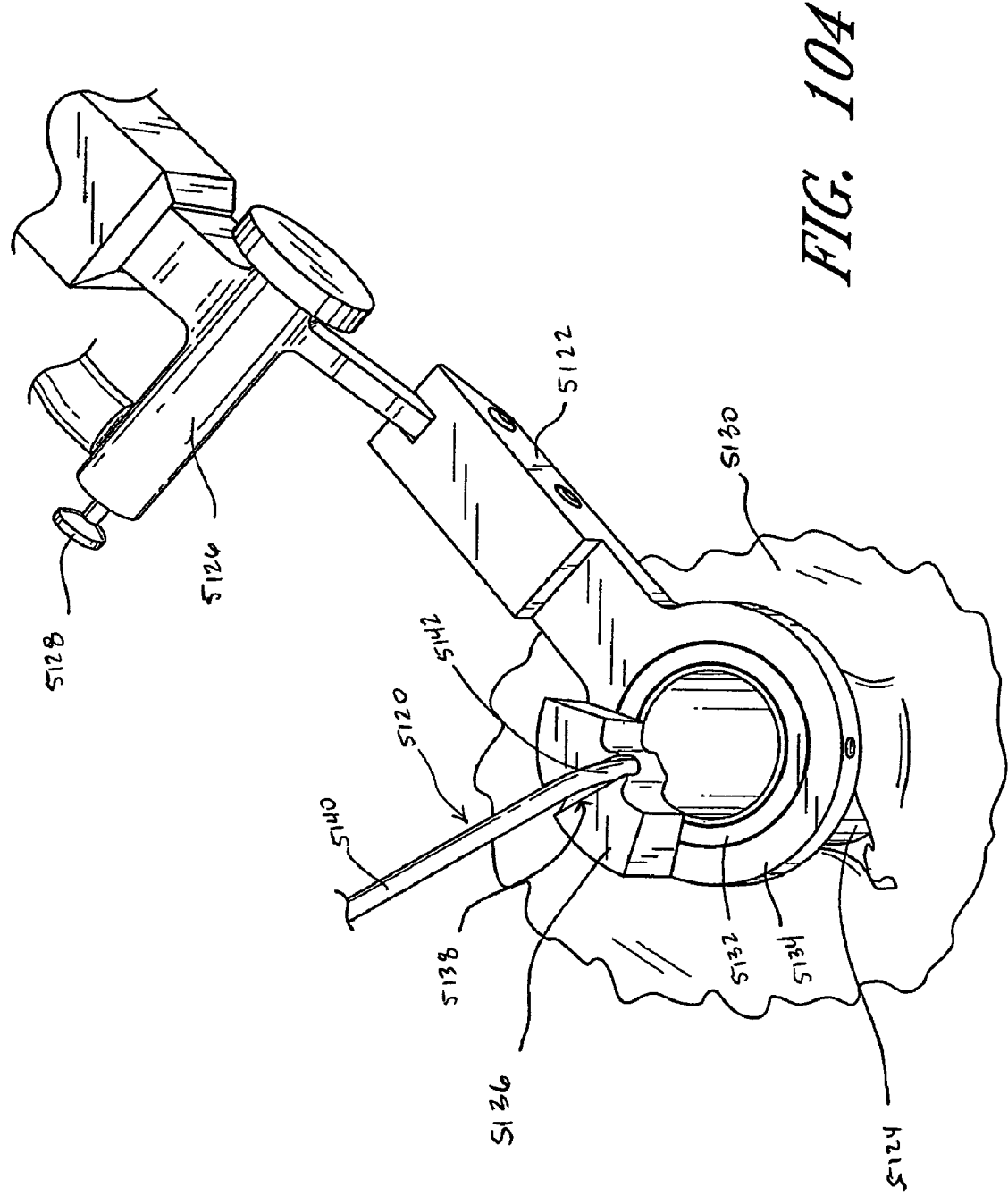
FIG. 104 is a perspective view of a portion of one embodiment of a surgical system that includes an access device, a support arm, and a lighting element shown applied to a patient.
Figure 105:
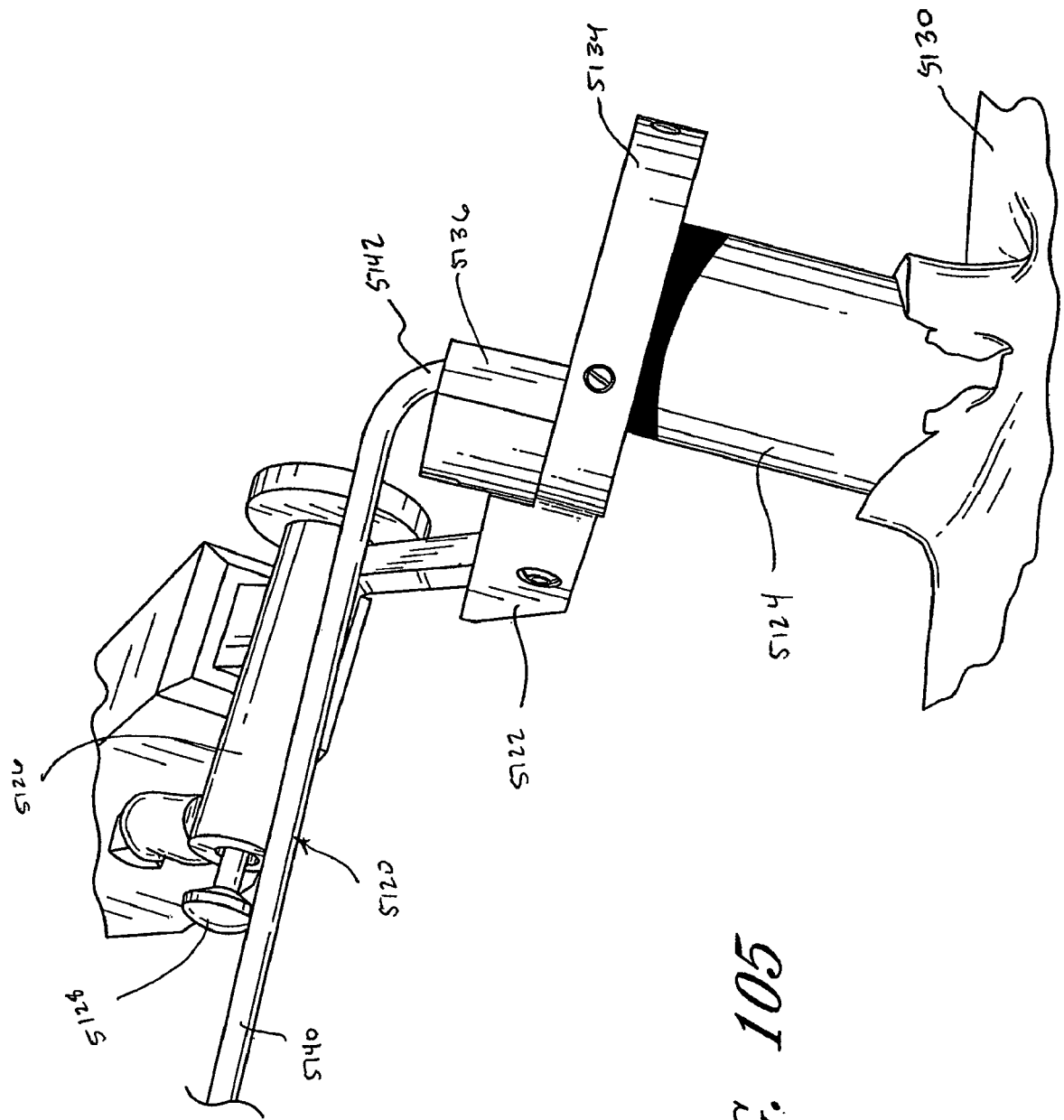
FIG. 105 is a perspective side view of the surgical system of FIG. 104 shown applied to a patient.
Figure 106:
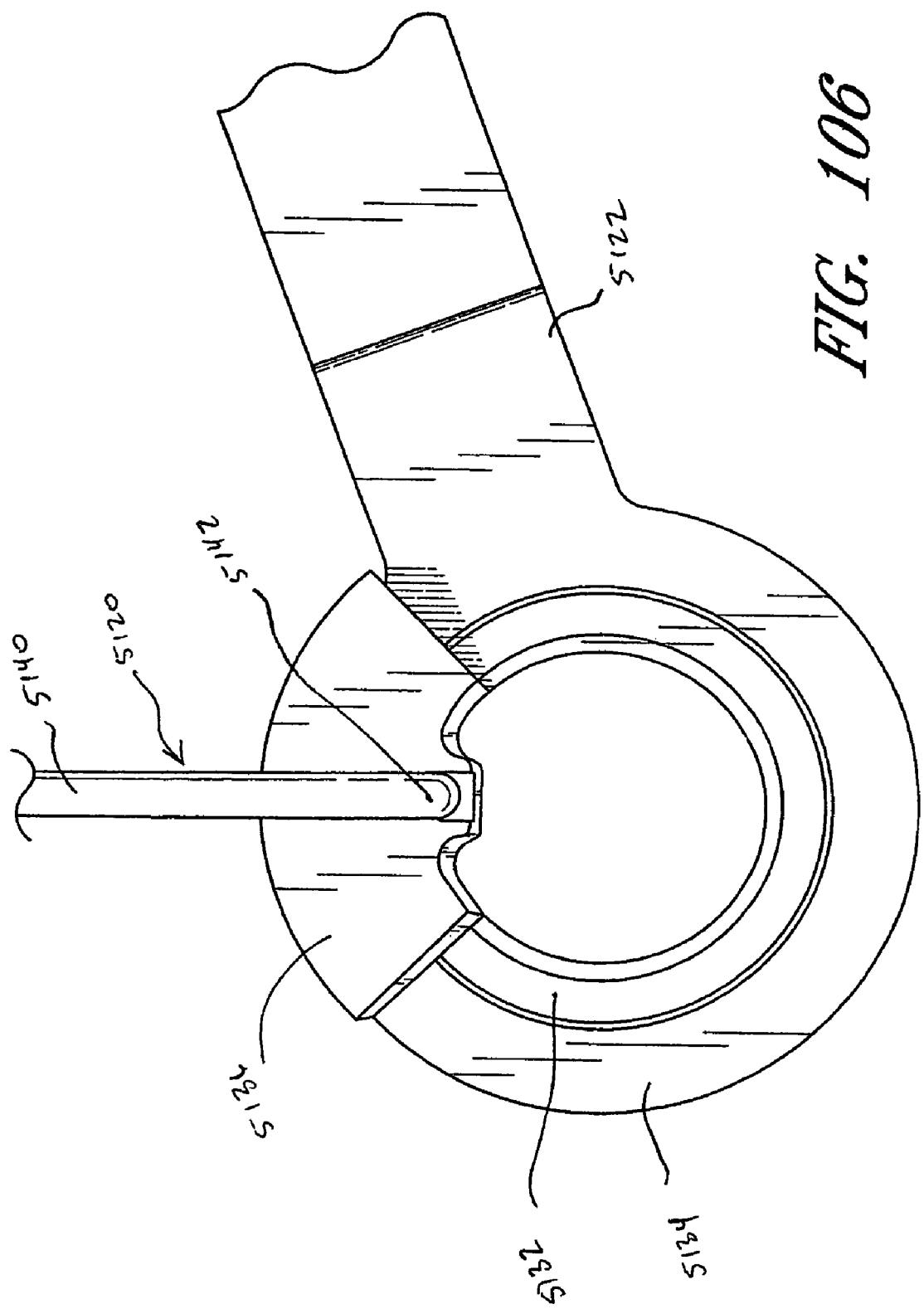
FIG. 106 is a top view of the surgical system of FIG. 104.

FIGS. 104-109 illustrate embodiments having lighting elements. FIGS. 104-106 illustrate one embodiment of a lighting element 5120 coupled with a support arm 5122 compatible with an access device 5124 having a proximal portion with a generally circular cross section. In other embodiments, support arms can be configured to be coupled with access devices having proximal portions with generally oblong or oval cross sections.

The support arm 5122 preferably is coupled with the access device 5124 to provide support for the access device 5124 during a procedure. As shown in FIGS. 104 and 105, the support arm 5122 comprises a pneumatic element 5126 for maintaining the support arm 5122 in a desired position. Depressing a button 5128 coupled with a valve of the pneumatic element 5126 releases pressure and allows the support arm 5122 and access device 5124 to be moved relative the patient 5130. Releasing the button 5128 of the pneumatic element 5126 increases pressure and maintains the access device 5124 and support arm 5122 in the desired position. The support arm 5122, as shown, is configured for use with a mechanical arm using a suction, or a vacuum to maintain the access device in a desired location. One of skill in the art will recognize that various other support arms and mechanical arms can be used. For example, commercially available mechanical arms having clamping mechanisms can be used as well as suction or pressure based arms.

As shown in FIGS. 104-106, the support arm 5122 can comprise an inner ring portion 5132 and an outer ring portion 5134 for surrounding the access device 5124 at its proximal end. In the illustrated embodiment, the inner and outer ring portions 5132, 5134 are fixed relative each other. In other embodiments the inner and outer ring portions 5132, 5134 can move relative each other. The support arm 5122 preferably comprises a lighting element support portion 5136. In the illustrated embodiment, the lighting element support portion 5136 extends above upper surfaces of the inner and outer ring portions 5132, 5134. The lighting element support portion 5136 can extend from the inner ring portion 5132, the outer ring portion 5134, or both. The lighting element support portion 5136 can have a notch or groove 5138 for receiving and supporting the lighting element 5120. Additionally, the lighting element support portion 5136 can have one or more prongs extending at least partially over the lighting element 5120 to hold it in place.

In the illustrated embodiment, the lighting element 5120 has an elongated proximal portion 5140 and a curved distal portion 5142. The proximal portion 5140 of the lighting element 5120 preferably is coupled with a light source (not shown). The curved distal portion of the lighting element 5120 in one embodiment extends only a short distance into the access device and is configured to direct light from the light source down into the access device 5124. In another embodiment, the lighting element 5120 can be provided such that it does not extend into the access device. In such an embodiment, the right portions 5132 and 5134 only partially surround the proximal end of the access device 5124. Providing a lighting element 5120 for use with the access device 5124 preferably allows a user to see down into the access device 5124 to view a surgical location. Accordingly, use of a lighting element 5120 can, in some cases, enable the user to perform a procedure, in whole or in part, without the use of an endoscope. In one embodiment, the lighting element 5120 enables a surgeon to perform the procedure with the use of microscopes or loupes.

Figure 107:
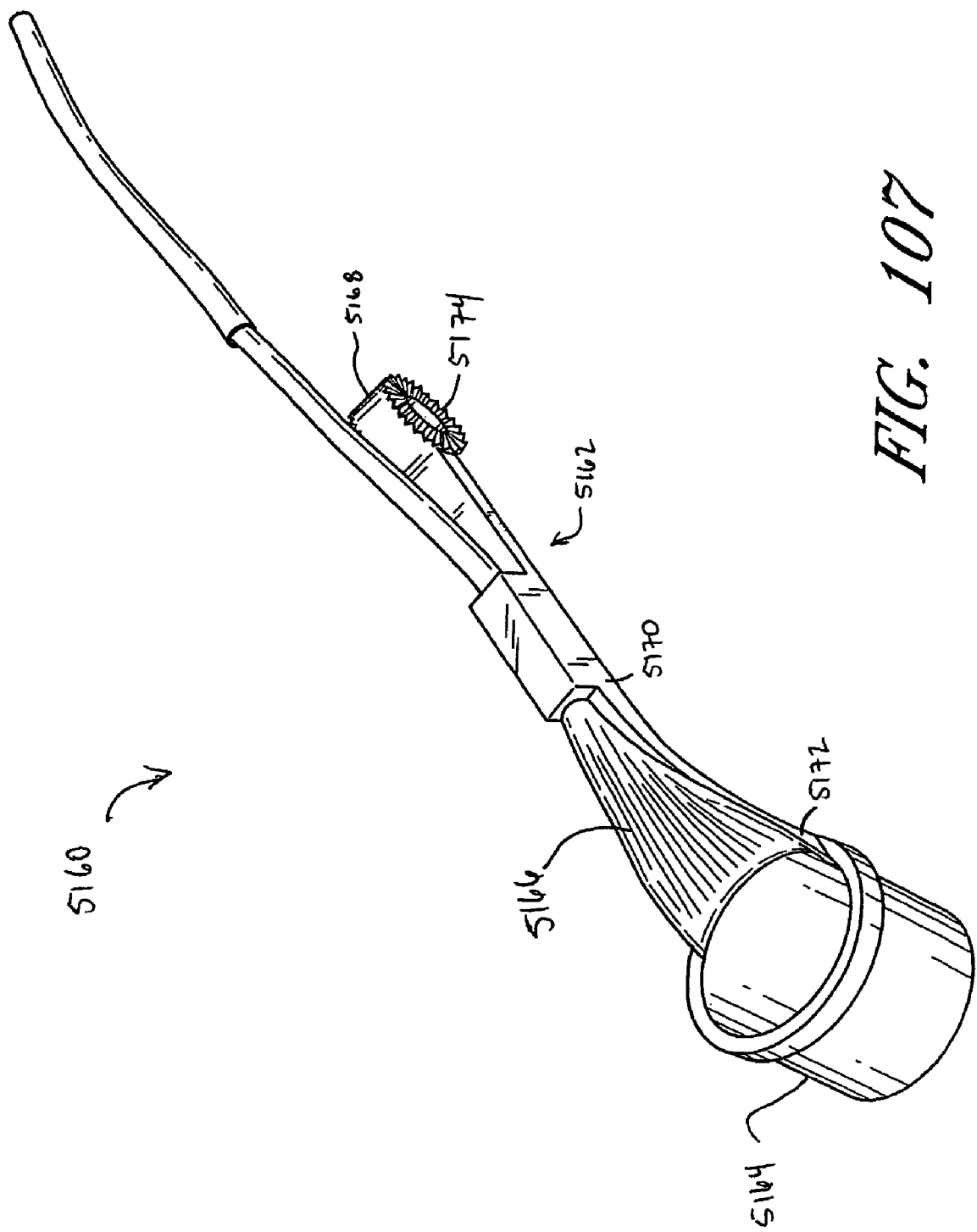
FIG. 107 is a perspective view of one embodiment of a lighting element.

FIGS. 107-109 illustrate other embodiments of lighting elements. As shown in FIG. 107, a lighting element 5160 comprises a support member 5162, an access device insert 5164, and fiber optic elements 5166. The support member 5162 has a proximal end 5168, a central portion 5170, and a distal end 5172. The proximal end 5168 preferably has a coupling portion 5174 for coupling the support member 5162 to a support arm or other support system (not shown). The central portion 5170 preferably is coupled with the fiber optic elements 5166 to provide support there to. The distal end 5172 preferably is coupled with the access device insert 5164.

In the illustrated embodiment, the access device insert 5164 is configured to be inserted in an access device having a proximal portion with a generally circular cross section. The access device insert 5164 is coupled with the fiber optic elements 5166. The fiber optic elements 5166 extend down into the access device insert 5164 so that the ends of the fiber optic elements 5166 can direct light down inside an access device along side portions there of.

FIGS. 108 and 109 illustrate other embodiments of lighting elements similar to the embodiment described with reference to FIG. 107. Components of the lighting elements shown in FIGS. 108 and 109 that were described with reference to FIG. 107 are given the same reference numerals that were used in FIG. 107, except that a ' is added in FIG. 108 and a " is added in FIG. 109. As shown in FIGS. 108 and 109, access device inserts 5164', 5164" are configured to be inserted into access devices having proximal portions with generally oblong, or oval, cross sections. As shown in FIG. 108, the access device insert 5164' has a generally oblong or oval shaped cross section. The access device insert 5164' is coupled with the fiber optic elements 5166' along a longer side surface of the access device insert 5164'. As shown in FIG. 109, the access device insert 5164" has a generally oblong or oval shaped cross section. The access device insert 5164" is coupled with the fiber optic elements 5166" along a shorter side surface of the access device insert 5164". Use of an illumination element with an expandable access device having an oblong shaped proximal section, in some cases, allows a doctor to perform procedures that would be difficult to perform using an endoscope. Increased visualization of the surgical location through the access device can simplify some procedures. For example, decompression of the contra-lateral side can be achieved more easily in some cases without the use of an endoscope.

The various devices, methods and techniques described above provide a number of ways to carry out the invention. Of course, it is to be understood that not necessarily all objectives or advantages described may be achieved in accordance with any particular embodiment described herein. Also, although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein.

What is claimed is:

1. A device for retracting tissue to provide access to a spinal location within a patient, said device comprising:
    an elongate body having a proximal end and a distal end and defining a length between the proximal and distal ends such that the distal end can be positioned inside the patient adjacent the spinal location, said elongate body comprising a generally oval shaped proximal portion and an expandable distal portion; and
    a passage extending through the elongate body between the proximal and distal ends;
    wherein said elongate body is expandable between a first configuration sized for insertion into the patient and a second configuration wherein the cross-sectional area of said passage at the distal end is greater than the cross-sectional area of said passage at the proximal end, wherein the passage is substantially enclosed by the elongate body between the proximal and distal ends in both the first configuration and the second configuration.

2. The device of claim 1, wherein said distal portion is generally oval shaped in the first configuration.

3. The device of claim 1, wherein said proximal portion and said distal portion comprise discrete members.

4. The. device of claim 1, wherein said distal portion comprises a first member and a second member.

5. The device of claim 1, wherein said distal portion comprises a first overlapping portion and a second overlapping portion, the first and second overlapping portions defining an overlap area, wherein the extent of overlap area is reduced when said distal portion is in the second configuration.

6. The device of claim 1, wherein said proximal portion is pivotable relative to said distal portion.

7. The device of claim 1, wherein said distal portion comprises a first dimension of about 24 mm and a second dimension of about 35 mm when said elongate body is in said first configuration.

8. The device of claim 1, wherein said distal portion comprises a first dimension of about 45 mm and a second dimension of about 70 mm when said elongate body is in said second configuration.

9. The device of claim 8, wherein said distal portion comprises a first dimension of about 24 mm and a second dimension of about 35 mm when said elongate body is in said first configuration.

10. The device of claim 1, wherein said proximal portion has a cross section having a first dimension of about 24 mm and a second dimension of about 35 mm.

11. The device of claim 1, wherein said passage is defined by a metallic inner surface extending substantially entirely around a perimeter of said passage between the proximal and distal ends in both the first configuration and the second configuration.

12. The device of claim 1, wherein said elongate body comprises multiple discrete pieces defining said passage.

13. The device of claim 1, wherein said elongate body comprising a generally oval shaped proximal portion in the first configuration.

14. The device of claim 1, wherein said elongate body comprising a generally oval shaped proximal portion in the second configuration.

15. The device of claim 1, wherein said elongate body comprising the same generally oval shaped proximal portion in both the first and the second configurations.

16. A device for providing access to a surgical location within a patient, said device comprising:
an elongate body having a proximal end, a distal end, and an inner surface, said inner surface defining a passage extending through the elongate body and through which surgical instruments can be inserted to the surgical location, said elongate body capable of having a configuration when located within the patient wherein the cross-sectional area of said passage at a first location is greater than the cross-sectional area of said passage at a second location, wherein the first location is distal to the second location, said passage being substantially enclosed at least when the elongate body is in an insertion configuration, said proximal end capable of having a generally oblong shaped cross section.

17. The device of claim 16, wherein said proximal end is capable of having a generally elliptical cross section.

18. The device of claim 16, wherein said proximal end is capable of having a non-circular cross section.

19. The device of claim 16, wherein the cross section is symmetrical about a first axis and a second axis, wherein the first axis is generally normal to the second axis.

20. The device of claim 16, wherein the configuration of the elongate body between the first location and the second location is generally conical when the elongate body is located within the patient.

21. The device of claim 16, wherein the first location is at a distal end of the elongate body, and the second location is at a proximal end of the elongate body.

22. The device of claim 16, wherein the elongate body is configured to be inserted through the skin of the patient and is sized to provide access to a spinal location.

23. The device of claim 16, wherein the elongate body is movable from a first configuration to a second configuration when located within the patient, the second configuration providing the cross-sectional area of said passage at a first location greater than the cross-sectional area of said passage at a second location, wherein the first location is distal to the second location.

24. The device of claim 23, wherein the elongate body is expandable from the first configuration to the second configuration.

25. The device of claim 23, wherein the elongate body has an oblong shaped cross section at its proximal end at least when the elongate body is in the second configuration.

26. The device of claim 25, wherein the elongate body has an oblong shaped cross section along substantially the entire length between the proximal end and the second location.

27. The device of claim 26, wherein said elongate body between the proximal end and the second location has a cross section having a first dimension of about 24 mm and a second dimension of about 35 mm.

28. The device of claim 25, wherein the elongate body has an oblong shaped cross section at its proximal end when the elongate body is in the first configuration.

29. The device of claim 16, wherein said passage is substantially enclosed by said inner surface.

30. The device of claim 16, wherein said passage is sized to receive multiple surgical instruments simultaneously.

31. A device for providing access to a surgical location within a patient, said device comprising:
an elongate body having a proximal end, a distal end, and an inner surface, said inner surface defining a passage extending through the elongate body and through which surgical instruments can be inserted to the surgical location, said elongate body comprising a first arcuate side portion and a second arcuate side portion, said elongate body being expandable from a first configuration to a second configuration when located within the patient such that in the second configuration the cross-sectional area of said passage at a first location is greater than the cross-sectional area of said passage at a second location, wherein the first location is distal to the second location, said first arcuate side portion and said second arcuate side portion being discrete members configured to substantially enclose said passage at least in the first configuration.

32. The device of claim 31, wherein the cross sectional area of the passage is symmetrical about a first axis and a second axis, wherein the first axis is generally normal to the second axis.

33. The device of claim 31, wherein the configuration of the elongate body between the first location and the second location is generally conical when the elongate body is expanded within the patient.

34. The device of claim 31, wherein the first location is at a distal end of the elongate body, and the second location is at a proximal end of the elongate body.

35. The device of claim 31, wherein the elongate body is configured to be inserted through the skin of the patient and is sized to provide access to a spinal location.

36. The device of claim 31, wherein the elongate body has a generally oval shaped cross section at its proximal end at least when the elongate body is in the second configuration.

37. The device of claim 36, wherein the elongate body has a generally oval shaped cross section along substantially the entire length between the proximal end and the second location.

38. The device of claim 37, wherein said elongate body between the proximal end and the second location has a cross section having a first dimension of about 24 mm and a second dimension of about 35 mm.

39. The device of claim 31, wherein said passage is sized to receive multiple surgical instruments simultaneously.

40. The device of claim 31, wherein said passage is substantially closed from said proximal end to said distal end at least in the first configuration.

41. The device of claim 31, wherein said passage is capable of having a generally oval shaped cross section between the first location and the proximal end at least in the first configuration.

42. The device of claim 31, wherein said first arcuate side portion and said second arcuate side portion are discrete members configured to substantially enclose said passage in the second configuration.

43. A device for providing access to a surgical location within a patient, said device comprising:

an elongate body having a proximal end, a distal end, and an inner surface, said inner surface defining a passage extending through the elongate body, said passage sized to receive multiple surgical instruments that can be inserted simultaneously to the surgical location, said elongate body being actuatable from a closed configuration to an expanded configuration wherein the cross-sectional area of said passage in said expanded configuration at a first location is greater than the cross-sectional area of said passage at a second location, wherein the first location is distal to the second location, said proximal end of said elongate body defining an oblong shaped cross section at least in the expanded configuration, said passage being substantially enclosed in at least said closed configuration by a first generally arcuate side portion and a second generally arcuate side portion, said first and second generally arcuate side portions being discrete members capable of moving away from each other as said elongate body is actuated from said closed configuration to said expanded configuration.

44. The device of claim 43, wherein the cross section is symmetrical about a first axis and a second axis, wherein the first axis is generally normal to the second axis.

45. The device of claim 43, wherein said elongate body between the proximal end and the second location has a cross section having a first dimension of about 24 mm and a second dimension of aboLlt 35 mm.

46. The device of claim 43, wherein the configuration of the elongate body between the first location and the second location is generally conical when the elongate body is located within the patient.

47. The device of claim 43, wherein the first location is at a distal end of the elongate body, and the second location is at a proximal end of the elongate body.

48. The device of claim 43, wherein the elongate body is configured to be inserted through the skin of the patient and is sized to provide access to a spinal location.

49. The device of claim 43, wherein the elongate body defines an oblong-shaped cross-section in the closed configuration.

50. The device of claim 43, wherein the passage is substantially enclosed by the first and second generally arcuate sides portions in the expanded configuration.

51. The device of claim 43, wherein the first and second generally arcuate side portions have at least one slot with a locking mechanism.

* * * * *